(12) United States Patent
Mao et al.

(10) Patent No.: US 9,682,970 B2
(45) Date of Patent: Jun. 20, 2017

(54) FLUORESCENT COMPOUNDS AND USES THEREOF

(71) Applicant: BIOTIUM, INC., Hayward, CA (US)

(72) Inventors: Fei Mao, Fremont, CA (US); Chingying Cheung, San Ramon, CA (US); Wai-Yee Leung, San Ramon, CA (US); Sarah Lynn Windler, Oakland, CA (US); Lori M. Roberts, Belmont, CA (US)

(73) Assignee: Biotium, Inc., Hayward, CA (US)

( * ) Notice: Subject to any disclaimer, the term of this patent is extended or adjusted under 35 U.S.C. 154(b) by 0 days.

(21) Appl. No.: 14/409,325

(22) PCT Filed: Jun. 28, 2013

(86) PCT No.: PCT/US2013/048784
§ 371 (c)(1),
(2) Date: Dec. 18, 2014

(87) PCT Pub. No.: WO2014/005125
PCT Pub. Date: Jan. 3, 2014

(65) Prior Publication Data
US 2016/0024067 A1 Jan. 28, 2016

Related U.S. Application Data

(60) Provisional application No. 61/666,698, filed on Jun. 29, 2012.

(51) Int. Cl.
| | | |
|---|---|---|
| C07D 417/06 | (2006.01) |
| C07D 413/06 | (2006.01) |
| C07D 417/14 | (2006.01) |
| C07D 413/14 | (2006.01) |
| C07D 215/38 | (2006.01) |
| C07D 487/04 | (2006.01) |
| C07D 209/14 | (2006.01) |
| C07D 277/64 | (2006.01) |
| C07D 513/06 | (2006.01) |
| C07C 53/18 | (2006.01) |
| C07D 209/20 | (2006.01) |
| C07D 519/00 | (2006.01) |

(52) U.S. Cl.
CPC ............ *C07D 417/06* (2013.01); *C07C 53/18* (2013.01); *C07D 209/14* (2013.01); *C07D 209/20* (2013.01); *C07D 215/38* (2013.01); *C07D 277/64* (2013.01); *C07D 413/06* (2013.01); *C07D 413/14* (2013.01); *C07D 417/14* (2013.01); *C07D 487/04* (2013.01); *C07D 513/06* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 3,854,956 A * | 12/1974 | Lincoln | G03C 1/12 430/570 |
| 4,582,789 A | 4/1986 | Sheldon, III et al. | |
| 4,883,867 A | 11/1989 | Lee et al. | |
| 5,321,130 A | 6/1994 | Yue et al. | |
| 5,410,030 A | 4/1995 | Yue et al. | |
| 5,436,134 A | 7/1995 | Haugland et al. | |
| 5,545,535 A | 8/1996 | Roth et al. | |
| 5,582,977 A | 12/1996 | Yue et al. | |
| 5,656,449 A | 8/1997 | Yue | |
| 5,658,751 A | 8/1997 | Yue et al. | |
| 5,661,035 A | 8/1997 | Tsien et al. | |
| 5,863,753 A | 1/1999 | Haugland et al. | |
| 5,994,056 A | 11/1999 | Higuchi | |
| 6,891,044 B2 | 5/2005 | Kania et al. | |
| 7,387,887 B2 | 6/2008 | Wittwer et al. | |
| 7,456,281 B2 | 11/2008 | Wittwer et al. | |
| 7,582,429 B2 | 9/2009 | Wittwer et al. | |
| 7,776,529 B2 | 8/2010 | Dallwig et al. | |
| 7,776,567 B2 | 8/2010 | Mao et al. | |
| 8,058,431 B2 | 11/2011 | Josel et al. | |
| 9,193,746 B2 | 11/2015 | Mao et al. | |
| 2004/0180889 A1 | 9/2004 | Suto et al. | |
| 2010/0233710 A1 | 9/2010 | McDougall et al. | |

FOREIGN PATENT DOCUMENTS

| | | | |
|---|---|---|---|
| JP | 2004075793 A | * | 3/2004 |
| WO | WO-2008052742 A1 | | 5/2008 |

OTHER PUBLICATIONS

Currell. Analytical Instrumentation: Performance Characteristics and Quality. John, Wiley & Sons. 2000.
Dragan, et al. Metal-enhanced PicoGreen fluorescence: application for double-stranded DNA quantification. Anal Biochem. Jan. 1, 2010;396(1):8-12. doi: 10.1016/j.ab.2009.09.010. Epub Sep. 11, 2009.
International search report and written opinion dated Mar. 27, 2014 for PCT/US2013/048784.
Johnston, et al. Characterization of the photoreaction between DNA and aminomethyl-trimethylpsoralen using absorption and fluorescence spectroscopy. Photochem Photobiol. Jun. 1981;33(6):785-91.
Kulinich, et al. Merocyanine dyes: synthesis, structure, properties and applications. Russ. Chem. Rev. 2009; 78(2):141-164.
Liew, et al. Genotyping of single-nucleotide polymorphisms by high-resolution melting of small amplicons. Clin Chem. Jul. 2004;50(7):1156-64.
Mao, et al. Characterization of EvaGreen and the implication of its physicochemical properties for qPCR applications. BMC Biotechnol. Nov. 9, 2007;7:76.
Moreda, et al. Novel heterocyclic dyes as DNA markers, Part I. synthesis and characterization. Tetrahedron. 1997; 53(37):12595-12604.
Reed, et al. Sensitivity and specificity of single-nucleotide polymorphism scanning by high-resolution melting analysis. Clin Chem. Oct. 2004;50(10):1748-54. Epub Aug. 12, 2004.
Schofield. PicoGmeter, a custom-made fluorometer for the quantification of dsDNA by PicoGreen fluorescence. Biotechniques. Nov. 2004;37(5):778-80, 782.

(Continued)

*Primary Examiner* — Golam M M Shameem
*Assistant Examiner* — Laura Daniel
(74) *Attorney, Agent, or Firm* — Wilson, Sonsini, Goodrich & Rosati

(57) ABSTRACT

The invention provides compounds, including fluorescent nucleic acid dyes, and methods for use including nucleic acid detection, nucleic acid amplification reactions, and high-resolution melt curve analysis. Further provided are kits, instruments and systems comprising compounds of the invention or adapted for use with compounds of the invention or other nucleic acid dyes.

1 Claim, 16 Drawing Sheets

(56) References Cited

OTHER PUBLICATIONS

Searle, et al. Sequence-specific interaction of Hoechst 33258 with the minor groove of an adenine-tract DNA duplex studied in solution by 1H NMR spectroscopy. Nucleic Acids Res. Jul. 11, 1990;18(13):3753-62.

Singer, et al. Characterization of PicoGreen reagent and development of a fluorescence-based solution assay for double-stranded DNA quantitation. Anal Biochem. Jul. 1, 1997;249(2):228-38.

Skoog, et al. Principles of Instrumental Analysis. 5th Ed. Harcourt Brace College Publishers. 1998.

Zhou, et al. Closed-tube genotyping with unlabeled oligonucleotide probes and a saturating DNA dye. Clin Chem. Aug. 2004;50(8):1328-35. Epub May 27, 2004.

Zhou, et al. High-resolution DNA melting curve analysis to establish HLA genotypic identity. Tissue Antigens. Aug. 2004;64(2):156-64.

Zipper, et al. Investigations on DNA Intercalation and Surface Binding by SYBR Green 1, Its Structure Determination and Methodological Implications. Nucleic Acid Research, vol. 32, No. 12, 2004, pp. 1-10.

\* cited by examiner

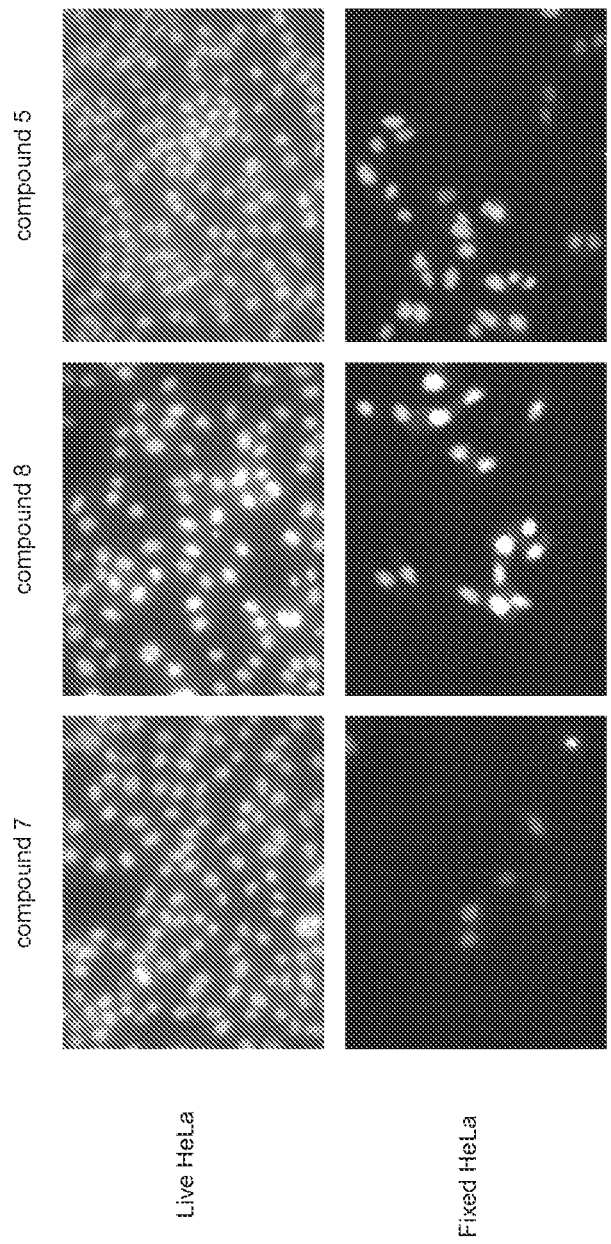

Staining of fixed cells with compound 36

FLUORESCENT COMPOUNDS AND USES THEREOF

CROSS-REFERENCE SECTION

This application claims benefit under 35 U.S.C. §119(e) to U.S. Provisional Application No. 61/666,698 filed Jun. 29, 2012, which is herein incorporated by reference in its entirety.

BACKGROUND OF THE INVENTION

Fluorescent dyes or stains can be used in the detection of nucleic acids, such as DNA and RNA present in biological samples. Nucleic acid is the genetic information transmitted from one generation to the next and involved in the routine functioning of a living organism. Nucleic acids are thus of great interest for research and development of diagnostics, therapeutics, forensic tools, and many other applications. Fluorescent dyes that specifically bind to nucleic acids and form highly fluorescent complexes are useful tools for studying nucleic acids. These dyes can be used to detect and quantify DNA and RNA in a variety of environments, including solutions, cell extracts, electrophoretic gels, micro-array chips, live or fixed cells, dead cells, and environmental samples. DNA binding dyes have also been used in quantitative real-time polymerase chain reaction or qPCR, a highly sensitive and specific gene detection technique widely used in both research and diagnostics. More recently, DNA binding dyes have also been used in high-resolution melt curve analysis, a post-PCR DNA analysis technique useful for gene mutation detection.

Despite the research progress and the commercial availability of a wide range products in the area, there remains a need for improvement in various aspects of nucleic acid binding dyes including but not limited to detection limit, dynamic range of detection and compatibility with different detection formats and instruments. It is the intention of the present invention to address some of these needs.

SUMMARY OF THE INVENTION

In one aspect, the invention provides compounds of Formula 1A or 1B:

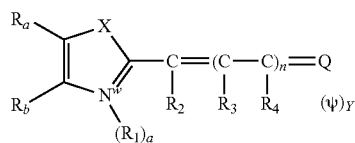

Formula 1A

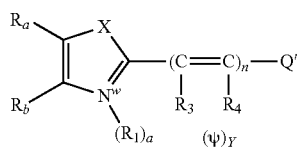

Formula 1B $R_1$ is $C_1$-$C_8$ alkyl, optionally substituted with —$NR_{31}R_{32}$ or —$N^+R_{31}R_{32}R_{33}$; or $R_1$ is $L_1$-$G_1$ or $L_2$-$G_2$;

$L_1$ is a linker moiety comprising 1-20 nonhydrogen atoms;

$G_1$ is substituted or unsubstituted guanidino, substituted or unsubstituted amidino, substituted or unsubstituted hydrazinoalkyl, substituted or unsubstituted aminooxy, or substituted or unsubstituted hydroxylamino;

$G_2$ is a reactive group, —$NR_{41}R_{42}$, —$N^+R_{41}R_{42}R_{43}$, a nucleic acid binding dye, protected or unprotected nucleoside, nucleotide or oligonucleotide;

each of $R_{31}$, $R_{32}$, $R_{33}$, $R_{41}$, $R_{42}$, and $R_{43}$ is independently selected from the group consisting of H, $C_1$-$C_8$ alkyl, aryl, heteroaryl, and heteroalkyl;

$L_2$ is a linker moiety comprising 2-10 nonhydrogen atoms;

each of $R_2$, $R_3$, and $R_4$ is independently H, $C_1$-$C_6$ alkyl, aryl, or heteroaryl;

each of $R_a$ and $R_b$ is independently H, $C_1$-$C_6$ alkyl, $C_2$-$C_6$ alkenyl, halo, azido, nitro, cyano, —$OR_{51}$, —$SR_{52}$, —$NR_{53}R_{54}$, —$NR_{55}$(C=O)$R_{56}$, —$NR_{55}S$(=O)$_2R_{56}$, or —C(=O)$NR_{55}R_{56}$, wherein each of $R_{51}$-$R_{56}$ is independently selected from H, $C_1$-$C_6$ alkyl, aryl, or heteroaryl; and wherein $R_{53}$ and $R_{54}$, or $R_{55}$ and $R_{56}$ taken together with the nitrogen to which they are attached optionally form a 5-8 membered ring;

or $R_a$ and $R_b$ taken together with the double bond they are attached to form a 5 or 6 membered aromatic or heteroaromatic ring substituted with at least one of $R_5$, $R_6$, $R_7$, and $R_8$, wherein each of $R_5$, $R_6$, $R_7$, and $R_8$ is independently hydrogen, halogen, azido, nitro, cyano, sultanate (SO$_3^-$), phosphonate (PO$_3^{2-}$), aryl, heteroaryl, —$NR_{61}R_{62}$, $L_3$-$G_1$ $C_1$-$C_8$ alkyl optionally substituted with —$NR_{63}R_{64}$ or —$OR_{65}$, or $L_3$-$G_2$; or $R_5$ and $R_6$, $R_6$ and $R_7$, $R_7$ and $R_8$, or $R_1$ and $R_8$ taken together form a 5-8 membered ring;

$L_3$ is a single bond or a linker moiety comprising 1-10 nonhydrogen atoms;

each of $R_{61}$-$R_{65}$ is independently H, $C_1$-$C_8$ alkyl, aryl, or heteroaryl; and $R_{61}$ and $R_{62}$ or $R_{63}$ and $R_{64}$ taken together with the nitrogen to which they are attached optionally form a 5-8 membered ring;

X is

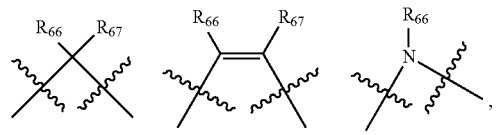

O, S or Se;

wherein each of $R_{66}$ and $R_{67}$ is independently $C_1$-$C_8$ alkyl, aryl, or heteroaryl; or $R_{66}$ and $R_{67}$ taken together with the carbons to which they are attached, form a 5 or 6 membered, monocyclic or bicyclic ring;

a is 0 or 1;

W represents charge and is +1 when a is 1, or is 0 when a is 0;

n is 0, 1, or 2;

ψ is a counterion;

Y is 1, 2, or 3;

Q is monocyclic, bicyclic, heterocyclyl, aryl or heteroaryl group, optionally substituted with $L_3$-$G_1$ or V; and Q is optionally further substituted with $R_9$, $R_{10}$, $R_{11}$, $R_{12}$, $R_{13}$, $R_{14}$ or $R_{15}$, Q' is monocyclic, bicyclic, heterocyclyl, aryl or heteroaryl group, optionally substituted with $L_3$-$G_1$ or V; and Q' is optionally further substituted with $R_9$, $R_{10}$, $R_{11}$, $R_{12}$, $R_{13}$, $R_{14}$ or $R_{15}$;

$R_9$ is $C_1$-$C_8$ alkyl, optionally substituted with —$NR_{34}R_{35}$ or —$N^+R_{34}R_{35}R_{36}$; aryl; heteroaryl; $L_1$-$G_1$; or $L_2$-$G_2$;

each of $R_{10}$, $R_{11}$, $R_{12}$, $R_{13}$, $R_{14}$ and $R_{15}$ is independently selected from the group consisting of hydrogen, halogen, azido, nitro, cyano, sulfonate ($SO_3^-$), phosphonate ($PO_3^{2-}$), aryl, heteroaryl, —$NR_{37}R_{38}$, $C_1$-$C_8$ alkyl optionally substituted with —$NR_{44}R_{45}$, —$OR_{44}$ or —$SR_{45}$, $C_1$-$C_8$ alkoxy, and $L_3$-$G_1$;

each of $R_{34}$, $R_{35}$, $R_{36}$, $R_{37}$, $R_{38}$, $R_{44}$ and $R_{45}$ is independently selected from $C_1$-$C_8$ alkyl, aryl and heteroaryl;

V has the formula:

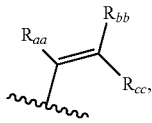

wherein each of $R_{aa}$, $R_{bb}$ and $R_{cc}$ is independently H, $C_1$-$C_8$ alkyl, halogen, cyano, —$NR_{71}R_{72}$, —$SR_{73}$, —$OR_{74}$, alkenyl, aryl, heteroaryl, or $L_3$-$G_1$; or $R_{aa}$ and $R_{bb}$ or $R_{bb}$ and $R_{cc}$ taken together optionally form a 5 or 6 membered monocyclic or bicyclic ring;

each of $R_{71}$-$R_{74}$ is independently H, $C_1$-$C_5$ alkyl, aryl, or heteroaryl; and at least one of said $R_1$, $R_5$, $R_6$, $R_7$, $R_8$, or Q comprises $G_1$.

In some embodiments, $R_1$ is $C_1$-$C_8$ alkyl, optionally substituted with —$NR_{31}R_{32}$ or —$N.^+R_{31}R_{32}R_{33}$; or $R_1$ is $L_1$-$G_1$. In other embodiments, one of $L_1$, $L_2$, or $L_3$ is a $C_1$-$C_{12}$ alkyl group. In some embodiments, $L_1$, $L_2$ or $L_3$ is a $C_1$-$C_{12}$ alkyl group wherein at least one methylene is replaced with —O—, —S—, or —$NR_{75}$—, where $R_{75}$ is H, $C_1$-$C_8$ alkyl, heteroalkyl, aryl, or heteroaryl. For example, at least two adjacent methylene units are replaced with

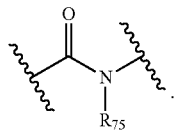

In some embodiments, W is +1, a is 1, and $R_1$ and $R_2$ in combination form a 5-9 membered ring. In other embodiments, W is +1, a is 1, and $R_1$ and $R_8$ in combination form a 5-9 membered ring.

In some embodiments of the compound of Formula 1A, the compound has the formula:

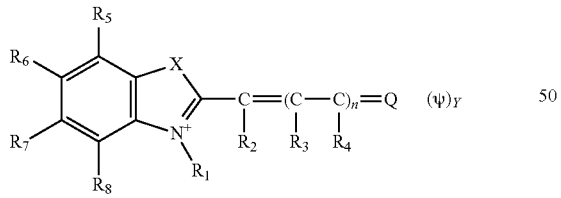

In some embodiments, the compound has the formula:

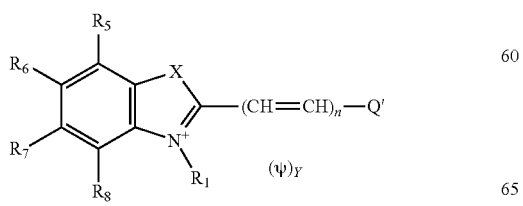

In some embodiments, $R_1$ and $R_8$ in combination form a 5-9 membered ring.

In some embodiments, n is 0, and $R_2$ is H.

In some embodiments, $R_5$, $R_6$ and $R_7$ are H.

In some embodiments, $G_1$ is substituted or unsubstituted guanidino, or substituted or unsubstituted amidino. For example, $G_1$ has the following structure:

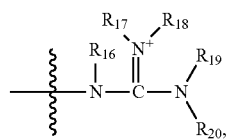

wherein each of $R_{16}$, $R_{17}$, $R_{18}$, $R_{19}$ and $R_{20}$ is independently selected from the group consisting of H, alkyl, aryl, heteroaryl, and $L_1$-$G_2$; and optionally any pair of $R_{16}$, $R_{17}$, $R_{18}$, $R_{19}$ and $R_{20}$ in combination with the nitrogen atom(s) to which they are attached form a ring.

In some embodiments, Q is a heteroaryl group having one of the following structures:

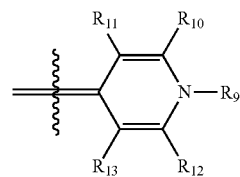

Q1

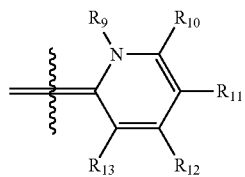

Q2

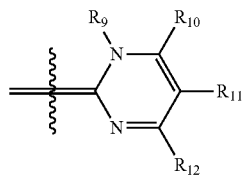

Q3

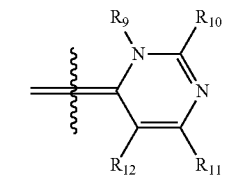

Q4

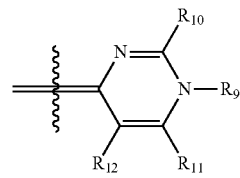

Q5

Q6 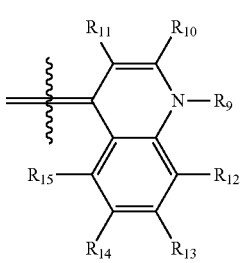

Q7 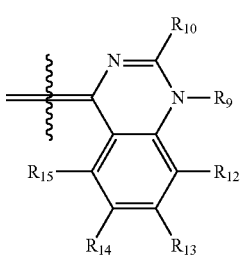

Q8 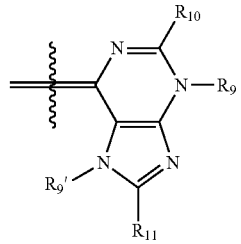

Q9 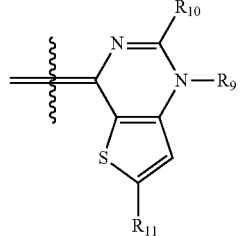

Q10 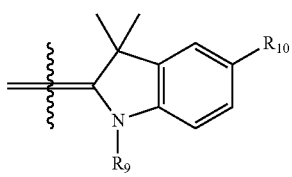

Q11 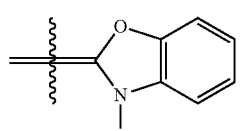

Q12 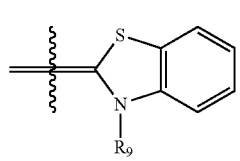

In some embodiments, Q is Q1, Q5, Q6, or Q7.

In some embodiments, Q' is:

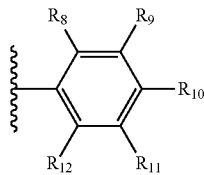

In some embodiments of Q or Q', $R_9$ is $L_2$-$G_2$. In some embodiments of Q or Q', $R_{10}$ is $L_3$-$G_1$. In other embodiments of Q or Q', $R_{10}$ is V.

In some embodiments, each of $R_5$-$R_8$ are H or alkyl.

Provided are also compositions comprising a compound selected from Table 1 or Table 2.

Further provided is a method of performing a nucleic acid amplification reaction comprising: a) conducting a nucleic acid amplification reaction in the presence of at least a first nucleic acid binding dye and a second nucleic acid binding dye, which reaction results in a first detectable optical signal produced by the first nucleic acid binding dye during the nucleic acid amplification reaction; b) detecting the first optical signal, wherein the first optical signal is indicative of the presence of amplified nucleic acids in the reaction; and wherein the intensity of the first optical signal is proportional to an increase in the amount of amplified nucleic acids resulting from said reaction, and further wherein one or more of the following conditions is satisfied: i) the first nucleic acid binding dye has a higher nucleic acid binding affinity than the second nucleic acid binding dye; ii) one of the first and second nucleic acid binding dyes has a higher binding affinity for G-C base pairs relative to A-T base pairs, and the other of the first and second nucleic acid binding dyes has a lower binding affinity for G-C base pairs relative to A-T base pairs; or iii) the molar ratio of the second nucleic acid binding dye to the first nucleic acid binding dye is at least 2:1.

In some embodiments, the method further comprises calculating a Ct value, wherein the Ct value represents the cycle number at which the first optical signal exceeds a threshold value. For example, the calculated Ct value is lower by at least one, two, three, four or more cycles when compared to a Ct value calculated by conducting a nucleic acid amplification reaction in the presence of only the second nucleic acid binding dye. In some embodiments, the nucleic acid amplification reaction is performed using a linearized GAPDH plasmid DNA template.

In some embodiments, the method further comprises (c) denaturing said amplified nucleic acids while measuring a second optical signal produced by the second nucleic acid binding dye, which second optical signal is indicative of the melting temperature of said amplified nucleic acids; and (d) detecting said second optical signal.

In some embodiments, the molar ratio of the second nucleic acid binding dye to the first nucleic acid binding dye is at least 2:1. In other embodiments, the molar ratio of the second nucleic acid binding dye to the first nucleic acid binding dye is at least 5:1, 10:1, 20:1, 50:1, 75:1, or 100:1. In some embodiments, the first nucleic acid binding dye has a higher nucleic acid binding affinity than the second nucleic acid binding dye. In some embodiments, one of the first and second nucleic acid binding dyes has a higher binding affinity for G-C base pairs relative to A-T base pairs, and the other of the first and second nucleic acid binding dyes has a lower binding affinity for G-C base pairs relative to A-T base pairs.

In some embodiments, the nucleic acid amplification reaction is a real-time polymerase chain reaction (qPCR).

In some embodiments, the first nucleic acid binding dye is EvaGreen, SYBR Green I, BRYT Green, or any compound of Table 1 or 2. In some embodiments, the second nucleic acid binding dye is EvaGreen, LCGreen, LCGreen Plus, ResoLight or any compound of Table 1 or 2.

Also provided is a method of performing a nucleic acid amplification reaction comprising: (a) conducting a nucleic acid amplification reaction in the presence of at least a first nucleic acid binding dye and a second nucleic acid binding dye, which reaction results in a first detectable optical signal produced by the first nucleic acid binding dye during the nucleic acid amplification reaction; (b) detecting the first optical signal, wherein the first optical signal is indicative of the presence of amplified nucleic acids in the reaction, and wherein the intensity of the first optical signal is proportional to an increase in the amount of amplified nucleic acids resulting from said reaction; (c) denaturing said amplified nucleic acids while measuring a second optical signal produced by the second nucleic acid binding dye, which second optical signal is indicative of the melting temperature of said amplified nucleic acids; and wherein the intensity of the second optical signal is inversely proportional to the amount of amplified nucleic acid in denatured form; detecting said second optical signal; and calculating a Ct value, wherein the Ct value represents the cycle number at which the first optical signal exceeds a threshold value, and wherein the calculated Ct value is lower by at least one cycle when compared to a Ct value calculated by conducting a nucleic acid.

For example, the nucleic acid amplification reaction is performed using a linearized GAPDH plasmid DNA template.

Also provided is an instrument for use in monitoring a nucleic acid amplification reaction as described herein, comprising: (a) an automated thermal cycler capable of alternately heating and cooling, and adapted to receive, at least one reaction vessel containing an amplification reaction mixture comprising a target nucleic acid, reagents for nucleic acid amplification; and the first and second nucleic acid dyes; and (b) a detector operable to detect the first optical signal during the amplification reaction.

Further provided is a kit comprising: a) one or more reagents reagents for performing a nucleic acid amplification reaction; b) a first nucleic acid binding dye and a second nucleic acid binding dye as described herein; and c) directions instructing a user to perform a nucleic acid amplification reaction as described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 shows that compounds 5, 7 and 8 can specifically stain the nuclei of live (upper panel) and fixed cells (lower panel). See Example 4 for experimental details.

DETAILED DESCRIPTION OF THE INVENTION

Definitions

Figure 1:
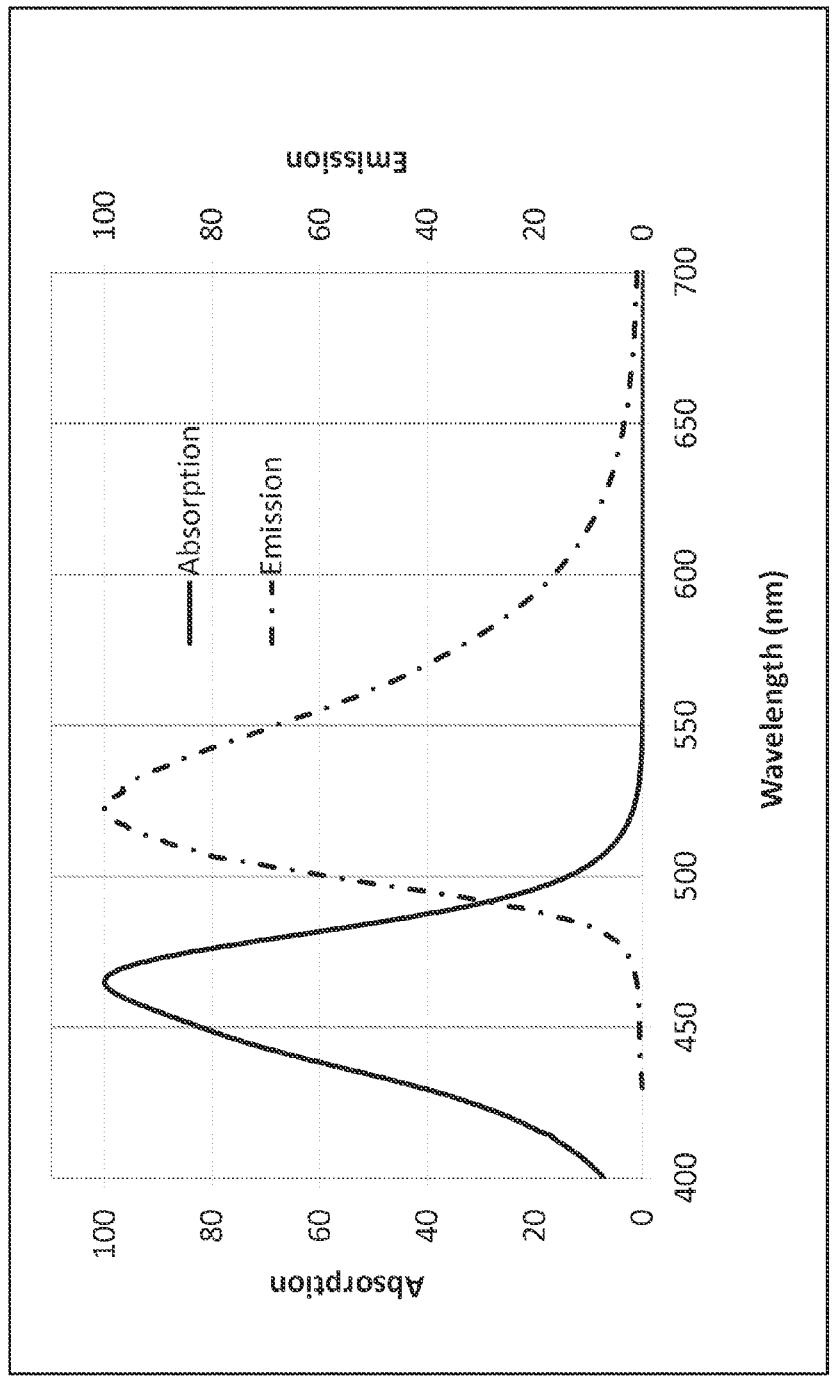
FIG. 1 shows normalized absorption and emission spectra of compound 5 (1 mM) in the presence of dsDNA (30 mg/mL) in 10 mM pH 7.4 Tris buffer. See Example 1 for experimental details.
Figure 2:
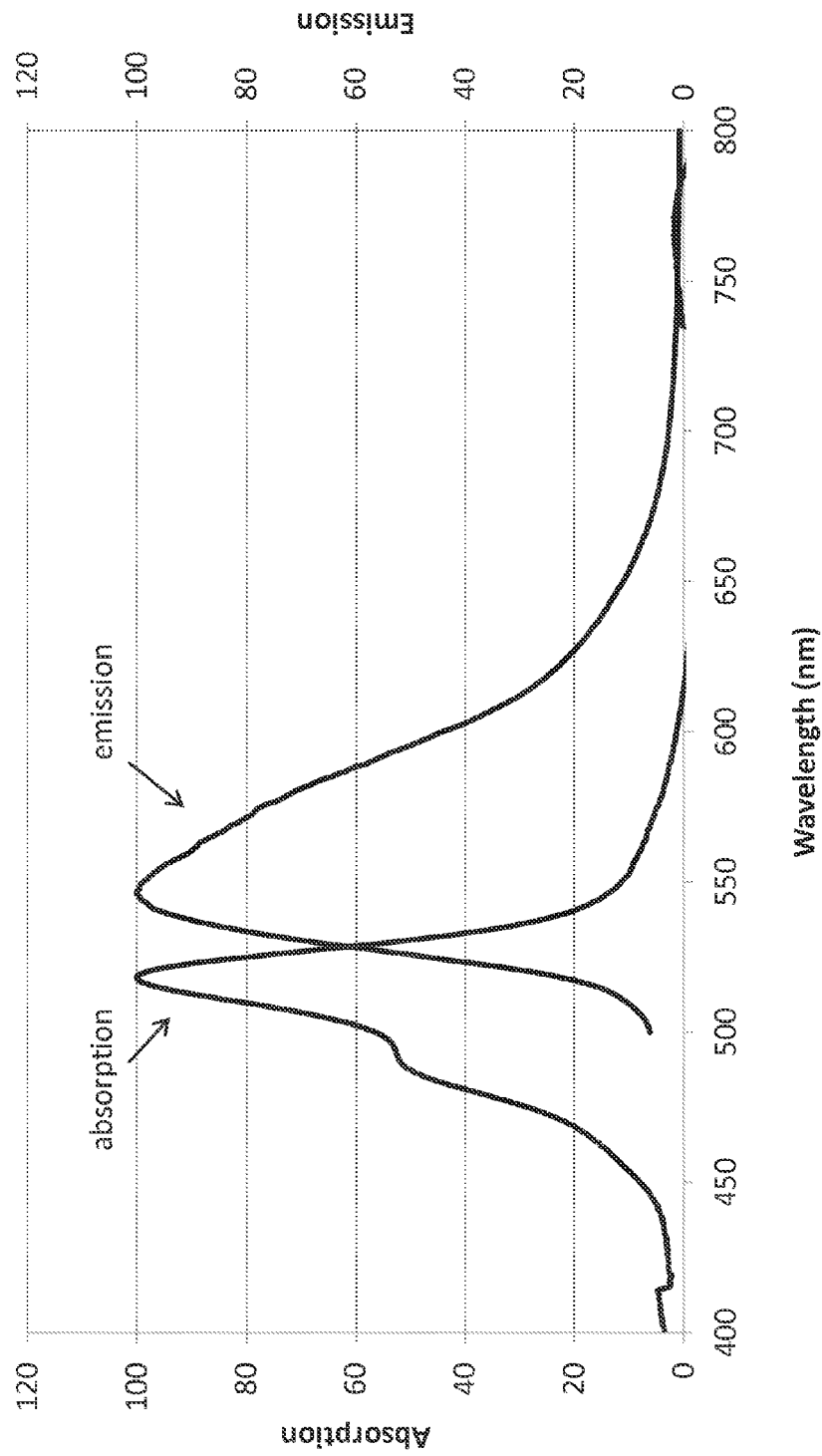
FIG. 2 shows the normalized absorption and emission spectra of compound 32 (1 mM) in the presence of dsDNA (30 mg/mL) in 10 mM pH 7.4 Tris buffer. See Example 1 for experimental details.

As used herein, "alkyl" includes branched, straight-chain, and cyclic saturated aliphatic hydrocarbon groups. Alkyl groups specifically include methyl, ethyl, propyl, butyl, pentyl, hexyl, heptyl, octyl, nonyl, decyl, and so on, as well as cycloalkyls such as cyclopropyl, cyclobutyl, cyclopentyl, cyclohexyl, tetrahydronaphthalene, methylenecylohexyl, and so on. "Alkoxy" represents an alkyl group attached through an oxygen bridge. $C_2$ alkyl refers to an alkyl group with two total carbons. Similarly, $C_8$ alkyl refers to an alkyl group with eight total carbons.

The term "alkenyl" refers to a non-aromatic hydrocarbon group, straight, branched or cyclic, containing at least one carbon to carbon double bond. Alkenyl groups include, but are not limited to, ethenyl, propenyl, butenyl and cyclohexenyl. The straight, branched or cyclic portion of the alkenyl group may contain double bonds and may be substituted if a substituted alkenyl group is indicated. The attachment of an alkenyl group is generally via a $sp^2$ hybridized carbon.

As used herein, "aryl" refers to any stable monocyclic or polycyclic carbon ring of up to 7 atoms in each ring, wherein at least one ring is aromatic. Examples of aryl groups include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, tetrahydroquinoline, xanthenyl, and coumarinyl. In cases where the heteroaryl substituent is bicyclic and one ring is non-aromatic or contains no heteroatoms, it is understood that attachment is via the aromatic ring or via the heteroatom containing ring, respectively.

Alkyl, alkenyl, aryl or heteroaryl groups may optionally be substituted with at least one substituent selected from alkyl, alkenyl, halogen, —CN, —$NO_2$, —$NR_{81}R_{82}$, —$OR_{81}$, —$NR_{81}S(=O)_2R_{82}$, —$C(=O)R_{81}$, or —$C(=O)NR_{81}R_{82}$, wherein each of $R_{81}$ and $R_{82}$ is independently selected from H, alkyl, aryl or heteroaryl and when both $R_{81}$ and $R_{82}$ are present, they may in combination form a monocyclic or polycyclic, aromatic or heteroaromatic ring.

The terms "halo" or "halogen" are intended to include chloro, fluoro, bromo and iodo groups.

The term "aromatic" is used in its usual sense, including unsaturation that is essentially delocalized across multiple bonds, such as around a ring.

The term "substituent" refers to an atom, radical or chemical group which replaces a hydrogen in a substituted chemical group, radical, molecule, moiety or compound.

Unless otherwise stated, the term "radical", as applied to any molecule or compound, is used to refer to a part, fragment or group of the molecule or compound rather than to a "free radical". A radical may be linked to another moiety through a covalent bond.

The terms "polynucleotides", "nucleic acids", and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. "Polynucleotide" may also be used to refer to peptide nucleic acids (PNA), locked nucleic acids (LNA), threofuranosyl nucleic acids (TNA) and other unnatural nucleic acids or nucleic acid mimics. Other base and backbone modifications known in the art are encompassed in this definition. See, e.g. De Mesmaeker et al (1997) Pure & Appl. Chem., 69, 3, pp 437-440.

The compound of the invention has the general structure of Formula 1A or Formula 1B below:

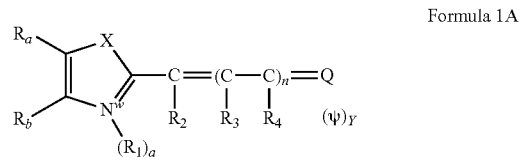

Formula 1A

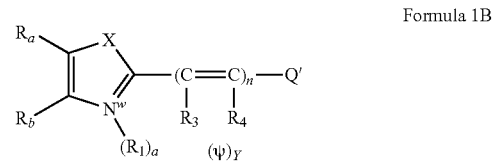

Formula 1B $R_1$ is $C_1$-$C_8$ alkyl, optionally substituted with —$NR_{31}R_{32}$ or —$N^1R_{31}R_{32}R_{33}$; or $R_1$ is $L_1$-$G_1$ or $L_2$-$G_2$;

$L_1$ is a linker moiety comprising 1-20 nonhydrogen atoms;

$G_1$ is substituted or unsubstituted guanidino, substituted or unsubstituted amidino, substituted or unsubstituted hydrazinoalkyl, substituted or unsubstituted aminooxy, or substituted or unsubstituted hydroxylamino;

$G_2$ is a reactive group, —$NR_{41}R_{42}$, —$N^+R_{41}R_{42}R_{43}$, a nucleic acid binding dye, protected or unprotected nucleoside, nucleotide or oligonucleotide;

each of $R_{31}$, $R_{32}$, $R_{33}$, $R_{41}$, $R_{42}$, and $R_{43}$ is independently selected from the group consisting of H, $C_1$-$C_8$ alkyl, aryl, heteroaryl, and heteroalkyl;

$L_2$ is a linker moiety comprising 2-10 nonhydrogen atoms;

each of $R_2$, $R_3$, and $R_4$ is independently H, $C_1$-$C_6$ alkyl, aryl, or heteroaryl;

each of $R_a$ and $R_b$ is independently H, $C_1$-$C_6$ alkyl, $C_2$-$C_6$ alkenyl, halo, azido, nitro, cyano, —$OR_{51}$, $SR_{52}$, —$NR_{53}R_{54}$, —$NR_{55}(C=O)R_{56}$, —$NR_{55}S(=O)_2R_{56}$, or —$C(=O)NR_{55}R_{56}$, wherein each of $R_{51}$-$R_{56}$ is H, $C_1$-$C_6$ alkyl, aryl, or heteroaryl; and wherein $R_{53}$ and $R_{54}$, or $R_{55}$ and $R_{56}$ taken together with the nitrogen to which they are attached optionally form a 5-8 membered ring;

or $R_a$ and $R_b$ taken together with the double bond they are attached to form a 5 or 6 membered aromatic or heteroaromatic ring substituted with at least one of $R_5$, $R_6$, $R_7$, and $R_8$, wherein each of $R_5$, $R_6$, $R_7$, and $R_8$ is independently hydrogen, halogen, azido, nitro, cyano, sulfonate ($SO_3^-$), phosphonate ($PO_3^{2-}$), aryl, heteroaryl, —$NR_{61}R_{62}$, $C_1$-$C_8$ alkyl optionally substituted with —$NR_{63}R_{64}$ or —$OR_{65}$, or $L_3$-$G_2$; or $R_5$ and $R_6$, $R_6$ and $R_7$, $R_7$ and $R_8$, or $R_1$ and $R_8$ taken together form a 5-8 membered ring;

$L_3$ is a single bond or a linker moiety comprising 1-10 nonhydrogen atoms;

each of $R_{61}$-$R_{65}$ is independently H, $C_1$-$C_8$ alkyl, aryl, or heteroaryl; and $R_{61}$ and $R_{62}$ or $R_{63}$ and $R_{65}$ taken together with the nitrogen to which they are attached optionally form a 5-8 membered ring;

X is

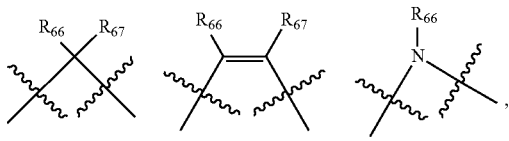

O, S or Se;

wherein each of $R_{66}$ and $R_{67}$ is independently H, $C_1$-$C_8$ alkyl, aryl, or heteroaryl; and when both $R_{66}$ and $R_{67}$ are present, taken together with the carbons to which they are attached, form a 5 or 6 membered, monocyclic or bicyclic ring;

a is 0 or 1;

W represents charge and is +1 when a is 1, or is 0 when a is 0;

n is 0, 1, or 2;

ψ is a counterion;

Y is 1, 2, or 3;

Q is a monocyclic or bicyclic, aryl or heteroaryl group, optionally substituted with $L_3$-$G_1$ or V; and Q is optionally further substituted with $R_9$, $R_{10}$, $R_{11}$, $R_{12}$, $R_{13}$, $R_{14}$ or $R_{15}$;

Q' is a monocyclic or bicyclic, aryl or heteroaryl group, optionally substituted with $L_3$-$G_1$ or V; and Q' is optionally further substituted with $R_9$, $R_{10}$, $R_{11}$, $R_{12}$, $R_{13}$, $R_{14}$ or $R_{15}$;

$R_9$ is $C_1$-$C_8$ alkyl, optionally substituted with —$NR_{34}R_{35}$ or —$N^+R_{34}R_{35}R_{36}$; aryl; heteroaryl; $L_1$-$G_1$; or $L_2$-$G_2$;

each of $R_{10}$, $R_{11}$, $R_{12}$, $R_{13}$, $R_{14}$ and $R_{15}$ is independently selected from the group consisting of hydrogen, halogen, azido, nitro, cyano, sulfonate ($SO_3^-$), phosphonate ($PO_3^{2-}$), aryl, heteroaryl, —$NR_{37}R_{38}$, $C_1$-$C_8$ alkyl optionally substituted with —$NR_{44}R_{45}$, —$OR_{44}$ or —$SR_{45}$, $C_1$-$C_8$ alkoxy, and $L_3$-$G_1$;

each of $R_{34}$, $R_{35}$, $R_{36}$, $R_{37}$, $R_{38}$, $R_{44}$ and $R_{45}$ is independently selected from H, $C_1$-$C_8$ alkyl, aryl and heteroaryl;

V has the formula:

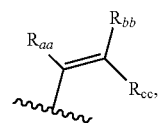

wherein each of $R_{aa}$, $R_{bb}$ and $R_{cc}$ is independently H, $C_1$-$C_8$ alkyl, halogen, cyano, —$NR_{71}R_{72}$, —$SR_{73}$, —$OR_{74}$, alkenyl, aryl, heteroaryl, or $L_3$-$G_1$; or $R_{aa}$ and $R_{bb}$ or $R_{bb}$ and $R_{cc}$ taken together optionally form a 5 or 6 membered monocyclic or bicyclic ring;

each of $R_{71}$-$R_{74}$ is independently H, $C_1$-$C_8$ alkyl, aryl, or heteroaryl; and at least one of said $R_1$, $R_{21}$, $R_{22}$ or Q comprises $G_1$.

In some embodiments, the compound has formula of Formula 2A below:

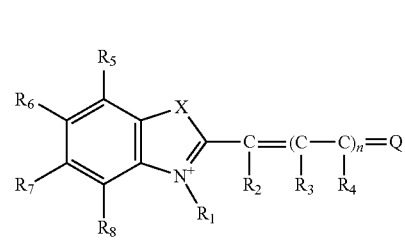

Formula 2A

In some embodiments, $R_2$ and $R_1$ in combination together with the atoms they are attached to form a 5- or 6-membered ring. In other embodiments, $R_8$ and $R_1$ in combination together with the atoms they are attached to form a 5- or 6-membered ring, for example a 6-membered unsubstituted saturated ring.

Formula 2A comprises at least one substituent selected from $L_3$-$G_2$, $L_2$-$G_2$ and V.

In some embodiments, Q is selected from heteroaryls having the following structures:

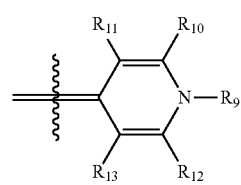

Q1

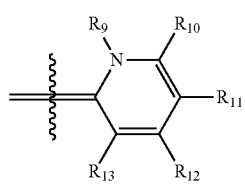

Q2

-continued

Q3 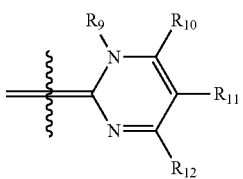

Q4 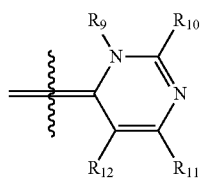

Q5 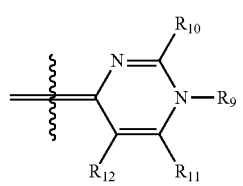

Q6 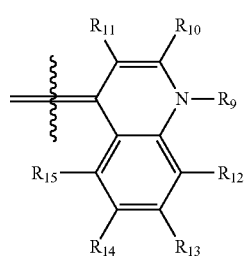

Q7 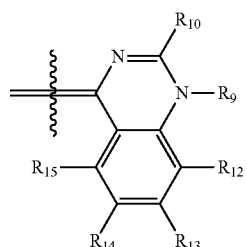

Q8 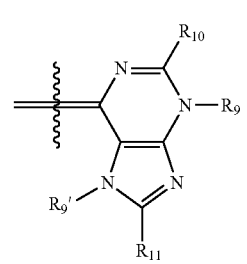

Q9 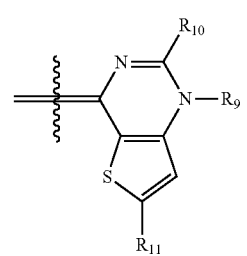

Q10 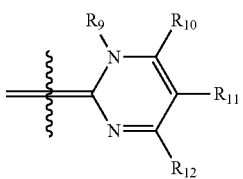

Q11 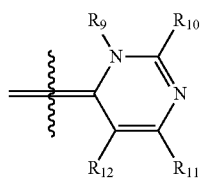

Q12 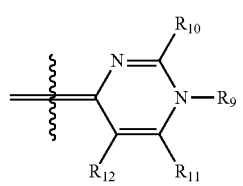

In some embodiments, one of $R_9$, $R_{10}$, $R_{11}$, $R_{12}$, $R_{13}$, $R_{14}$ or $R_{15}$ is $L_1$-$G_1$.

In some embodiments, Q is Q1, Q5, Q6 or Q7.

In some embodiments, the $R_9$ of Q1, Q5, Q6 and Q7 is -$L_3$-$G_1$.

In another preferred embodiment, the $R_{10}$ of Q1, Q5, Q6 and Q7 is -$L_1$-$G_1$ or V.

Preferably, $G_1$ is a substituted or unsubstituted guanidino group, or a substituted or unsubstituted amidino group. According to some embodiments, the guanidino group may have the following general structure:

Formula 3

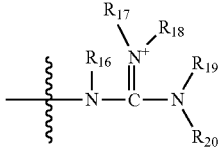

Where $R_{16}$, $R_{17}$, $R_{18}$, $R_{19}$ and $R_{20}$ are each independently H, alkyl, aryl, heteroaryl or a -$L_2$-$G_2$; or any pair of R16, R17, R18, R19 and R20 in combination together with the nitrogen atom(s) they are attached to form a ring. Non-limiting examples of guanidino include:

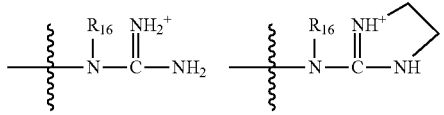

where $R_{16}$ is H or $C_1$-$C_6$ alkyl.

Compounds of present invention may comprise a linker moiety, such as $L_1$, $L_2$ or $L_3$. $L_1$, $L_2$ and $L_3$ may be independently selected from a polymethylene group (—$(CH_2)_n$—), a polypropylene group (—$(CH_3CH)_n$—), a methylene, a single bond or a mixture of polymethylene and polypropylene. $L_1$, $L_2$ and $L_3$ may comprise a heterocycle, an aryl or a heteroaryl. In addition, $L_1$, $L_2$ and $L_3$ may be an oligomer of ethylene oxide (—$(CH_2CH_2O)_n$—) or propylene oxide (—$(CH_3CHCH_2O)_n$—). It is understood that the choice of n is within the definition for $L_1$, $L_2$ and $L_3$. In some embodiments, at least one of the methylene unit in polymethylene is replaced with a O, S, or $NR_{77}$ group, wherein $R_{77}$ is selected from H, $C_1$-$C_8$ alkyl, heteroalkyl, aryl, or heteroaryl. In some embodiments, at least two of the methylene units are replaced with

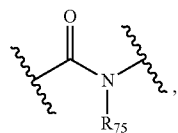

wherein $R_{75}$ is selected from H, $C_1$-$C_8$ alkyl, heteroalkyl, aryl, or heteroaryl.

Non-limiting examples of $L_1$, $L_2$, and $L_3$ groups include the following:

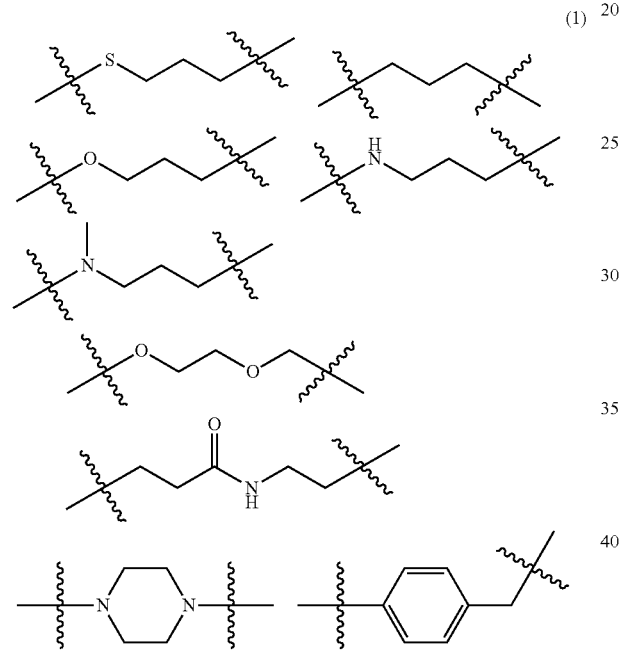

(1)

Nonlimiting examples of -$L_1$-$G_1$ and -$L_3$-$G_1$ include the following:

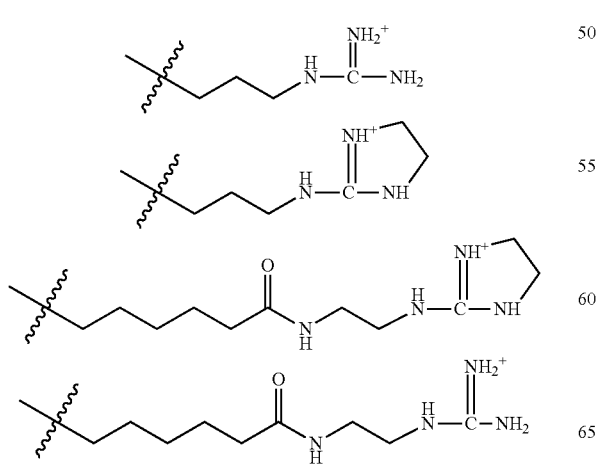

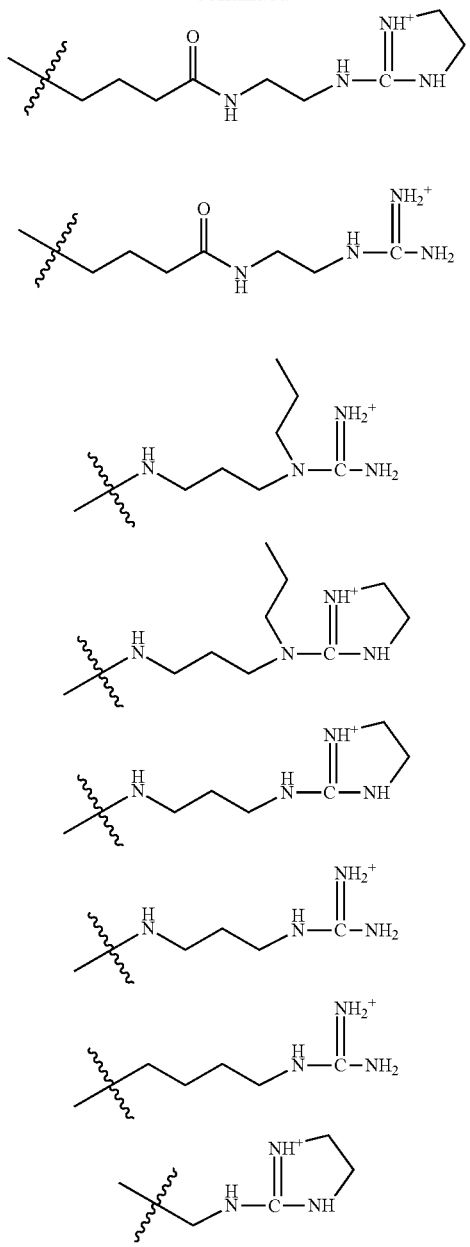

According to some embodiment of the invention, $G_1$ is a substituted or unsubstituted amidino group. Said amidino may be connected to the linker moiety $L_1$ or $L_3$ either via the carbon atom or one of the nitrogen atoms of the amidino as shown below:

Formula 4A

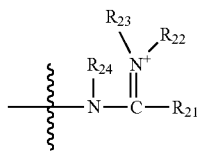

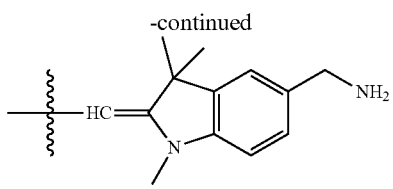

Formula 4B

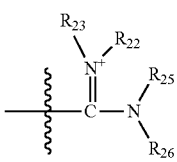

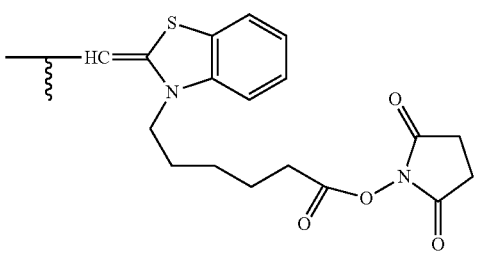

wherein each of $R_{21}$, $R_{22}$, $R_{23}$, $R_{24}$, $R_{25}$ and $R_{26}$ is independently selected from the group consisting of H, alkyl, aryl, heteroaryl and -$L_2$-$G_2$; or any pair of $R_{21}$, $R_{22}$, $R_{23}$, $R_{24}$, $R_{25}$ and $R_{26}$ taken in combination together with the atom or atoms they are attached to form a ring. In some embodiments, the amidino has the formula of Formula 4A, where $R_{21}$ is methyl or a -$L_2$-$G_2$, $R_{22}$ and $R_{23}$ are H and $R_{24}$ is H or $C_1$-$C_6$ alkyl.

In some embodiments, Q has the structure of Q1, Q5, Q6, Q7 and Q8, and $R_{10}$ is a V as defined previously herein. According to some embodiments, V is a vinyl substituted by a heterocycle which is further substituted by -$L_1$-$G_1$, $L_2$-$G_2$ or -$L_3$-$G_1$. Suitable V also include substituted or unsubstituted styryls. Examples of some substituted Vs are shown below:

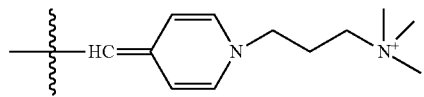

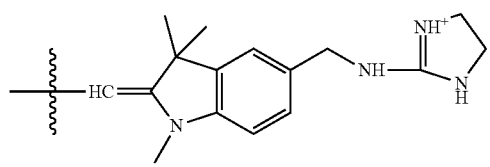

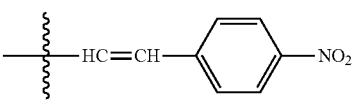

Where a compound shown herein is a charged moiety, the compound may be associated with one or more counterions which balance the charge of the compound. When the compound is positively charged, a suitable counterion can be an anion, for instance a biologically compatible anion. Biologically compatible anions include, but are not limited to, halides (such as chloride, fluoride, iodide or bromide), sulfate, phosphate, acetate, trifluoroacetate, lactate, citrate, gluconate, or hydroxyethansulfate. When depicting a formula of a compound of the invention, the counterion may or may not be explicitly described for simplicity, even though it can be present as understood by a person skilled in the art.

Some examples of dyes according to Formula 1A or Formula 2A are listed in Table 1 below.

TABLE 1

Compounds of Formulas 1A and 2A

| Cmpd. No. | Structure* | Description of $G_1$ or V moiety |
|---|---|---|
| 1 | 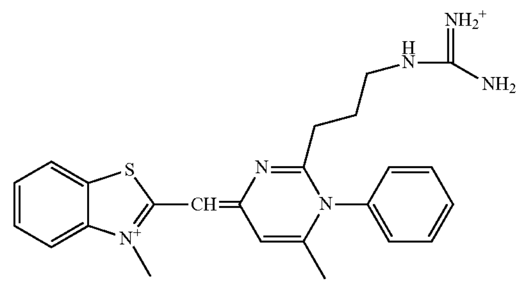 [SMILES: CC1=CC(=Cc2sc3ccccc3[n+]2C)N=C(CCCNC(N)=[NH2+])N1c1ccccc1] | guanidino |
| 2 | 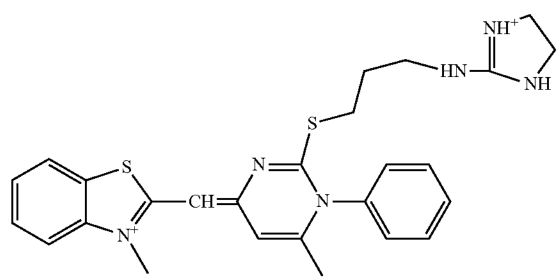 [SMILES: CC1=CC(=Cc2sc3ccccc3[n+]2C)N=C(SCCCNC2=[NH+]CCN2)N1c1ccccc1] | Cyclic guanidino |
| 3 | 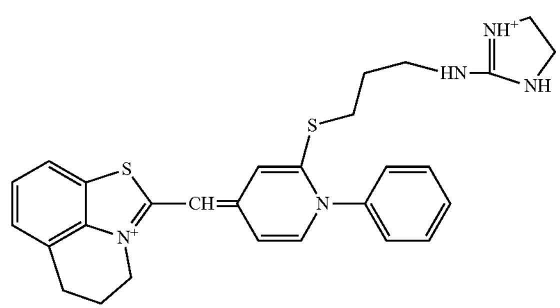 [SMILES: C1=CN(c2ccccc2)C(SCCCNC2=[NH+]CCN2)=CC1=Cc1sc2cccc3c2[n+]1CCC3] | Cyclic guanidino |

TABLE 1-continued
Compounds of Formulas 1A and 2A
| Cmpd. No. | Structure* | Description of $G_1$ or V moiety |
|---|---|---|
| 4 | 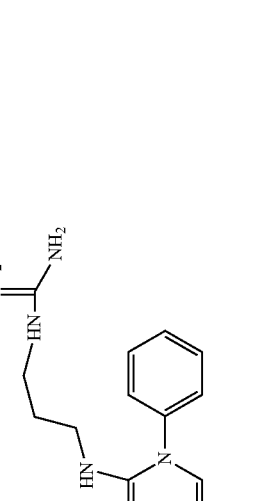 | guanidino |
| 5 | 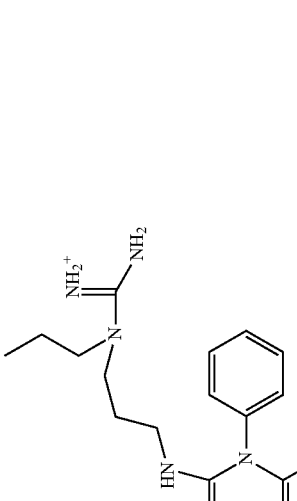 | guanidino |
| 6 | 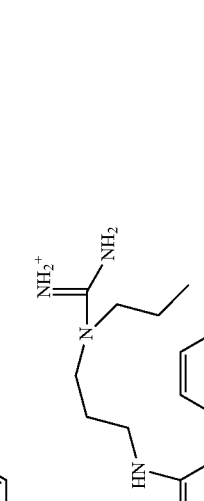 | Substituted guanidino |

TABLE 1-continued

Compounds of Formulas 1A and 2A

| Cmpd. No. | Structure* | Description of $G_1$ or V moiety |
|---|---|---|
| 7 | 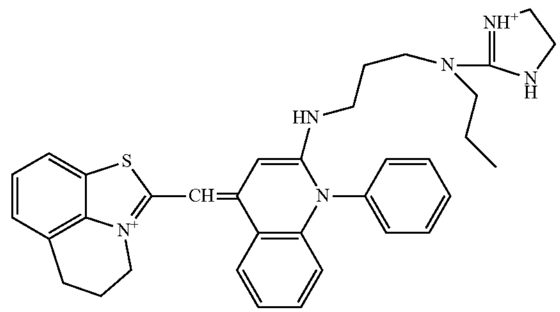 [SMILES: CCCN(CCCNC1=CC(=Cc2sc3cccc4c3[n+]2CCC4)c2ccccc2N1c1ccccc1)C1=[NH+]CCN1] | Substituted cyclic guanidino |
| 8 | 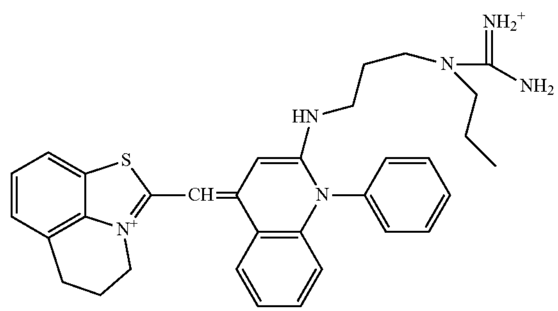 [SMILES: CCCN(CCCNC1=CC(=Cc2sc3cccc4c3[n+]2CCC4)c2ccccc2N1c1ccccc1)C(N)=[NH2+]] | Substituted amidino |
| 9 | 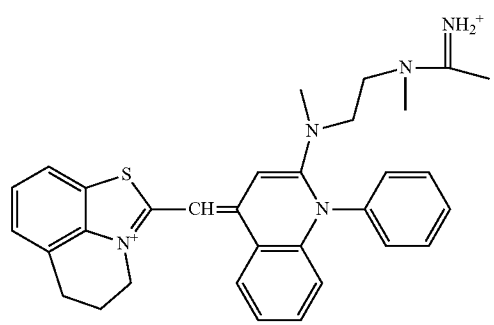 [SMILES: CC(=[NH2+])N(C)CCN(C)C1=CC(=Cc2sc3cccc4c3[n+]2CCC4)c2ccccc2N1c1ccccc1] | Substituted amidino |

TABLE 1-continued
Compounds of Formulas 1A and 2A
| Cmpd. No. | Structure* | Description of $G_1$ or V moiety |
|---|---|---|
| 10 | 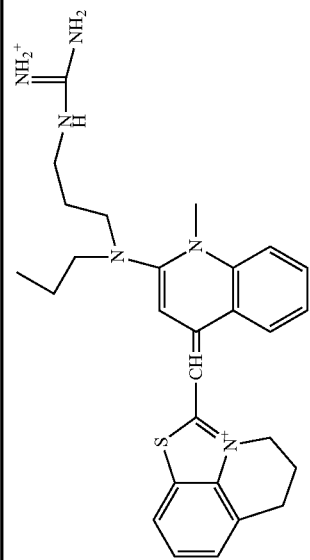 | guanidino |
| 11 | 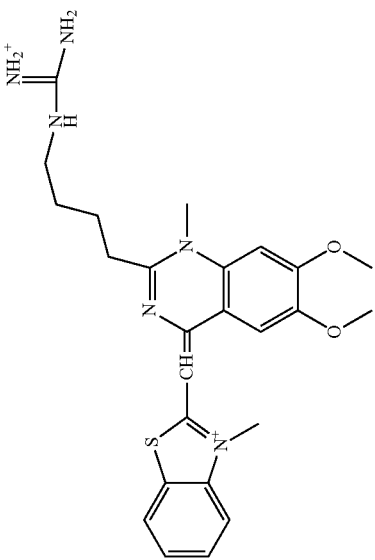 | guanidino |

TABLE 1-continued
Compounds of Formulas 1A and 2A
| Cmpd. No. | Structure* | Description of $G_1$ or V moiety |
|---|---|---|
| 12 | 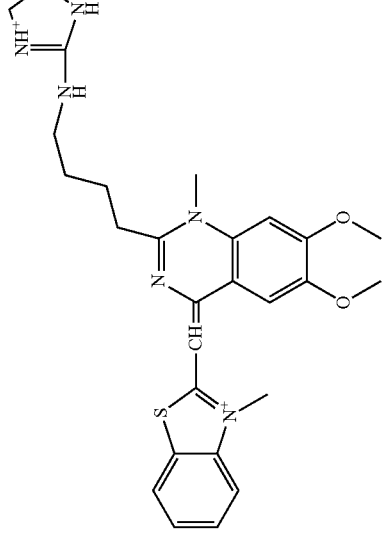 | Cyclic guanidino |
| 13 | 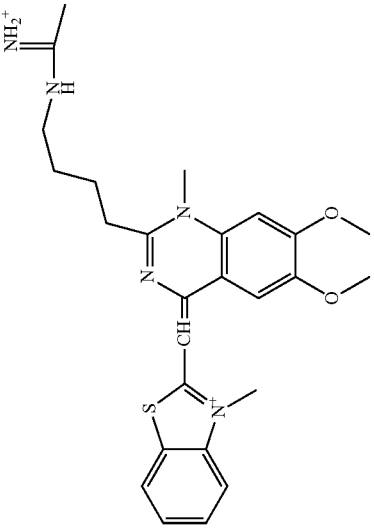 | amidino |
| 14 | 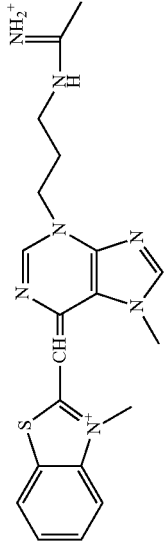 | amidino |

TABLE 1-continued

Compounds of Formulas 1A and 2A

| Cmpd. No. | Structure* | Description of $G_1$ or V moiety |
|---|---|---|
| 15 | 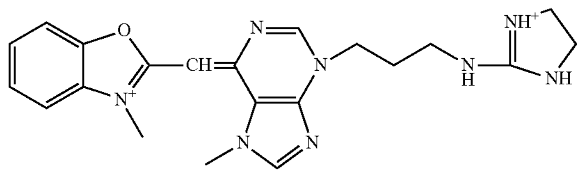 [SMILES: Cn1cnc2c1C(=Cc1oc3ccccc3[n+]1C)N=CN2CCCNC1=[NH+]CCN1] | Cyclic guanidino |
| 16 | 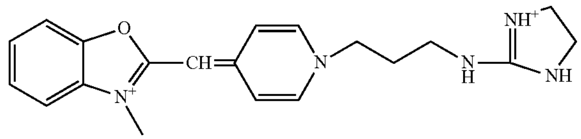 [SMILES: C[n+]1c(C=C2C=CN(CCCNC3=[NH+]CCN3)C=C2)oc2ccccc21] | Cyclic guanidino |
| 17 | 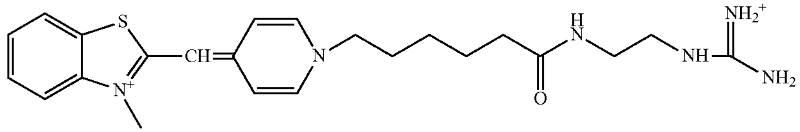 [SMILES: C[n+]1c(C=C2C=CN(CCCCCC(=O)NCCNC(N)=[NH2+])C=C2)sc2ccccc21] | guanidino |
| 18 | 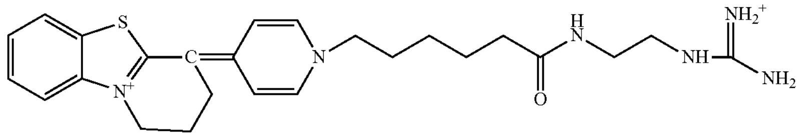 [SMILES: NC(=[NH2+])NCCNC(=O)CCCCCN1C=CC(=C2CCC[n+]3c2sc2ccccc23)C=C1] | guanidino |
| 19 | 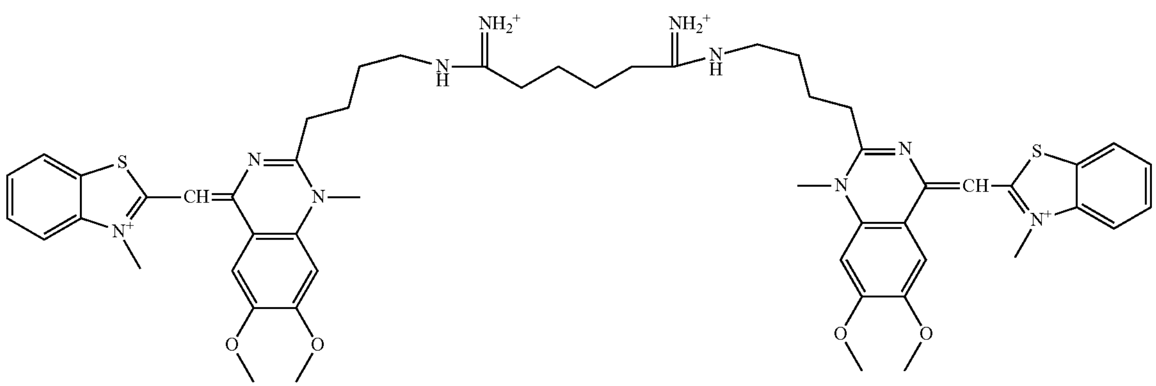 [SMILES: COc1cc2c(cc1OC)N(C)C(CCCCNC(=[NH2+])CCCCC(=[NH2+])NCCCCC1=NC(=Cc3sc4ccccc4[n+]3C)c3cc(OC)c(OC)cc3N1C)=NC2=Cc1sc2ccccc2[n+]1C] | Substituted amidino (and -$L_2$-$G_2$) |

TABLE 1-continued

Compounds of Formulas 1A and 2A

| Cmpd. No. | Structure* | Description of $G_1$ or V moiety |
|---|---|---|
| 20 | 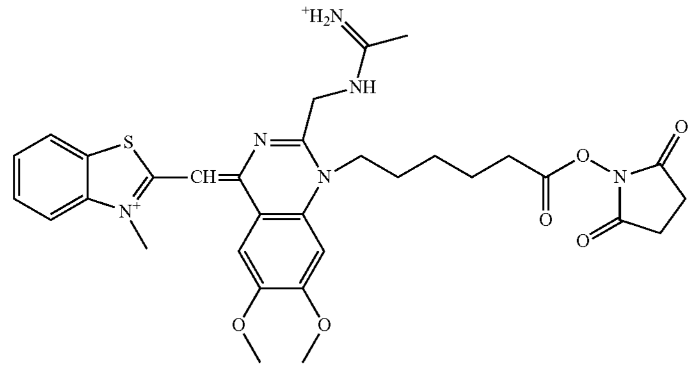 [SMILES: COc1cc2c(cc1OC)N(CCCCCC(=O)ON1C(=O)CCC1=O)C(CNC(C)=[NH2+])=NC2=Cc1sc2ccccc2[n+]1C] | Amidino (and -$L_2$-reactive group) |
| 21 | 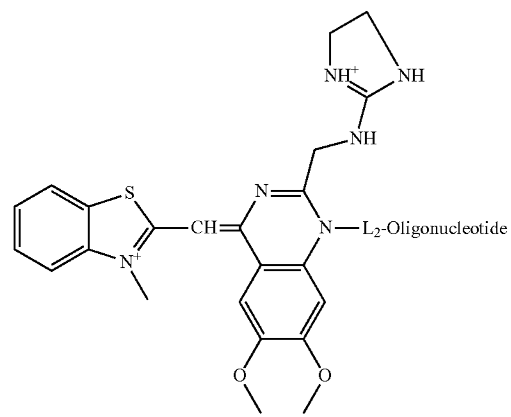 | Cyclic guanidine (and -$L_2$-oligo conjugate) |
| 22 | 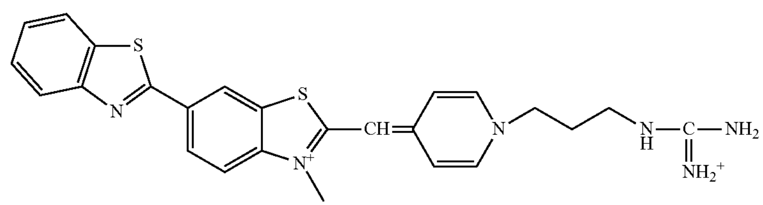 [SMILES: C[n+]1c(C=C2C=CN(CCCNC(N)=[NH2+])C=C2)sc2cc(-c3nc4ccccc4s3)ccc21] | guanidino |

TABLE 1-continued
Compounds of Formulas 1A and 2A
| Cmpd. No. | Structure* | Description of $G_1$ or V moiety |
|---|---|---|
| 23 | 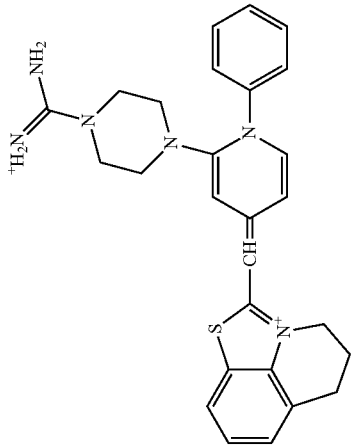 | Substituted guanidino |
| 24 | 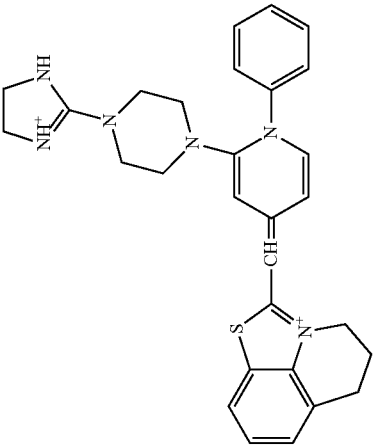 | Substituted cyclic guanidino |

TABLE 1-continued
Compounds of Formulas 1A and 2A
| Cmpd. No. | Structure* | Description of $G_1$ or V moiety |
|---|---|---|
| 25 | 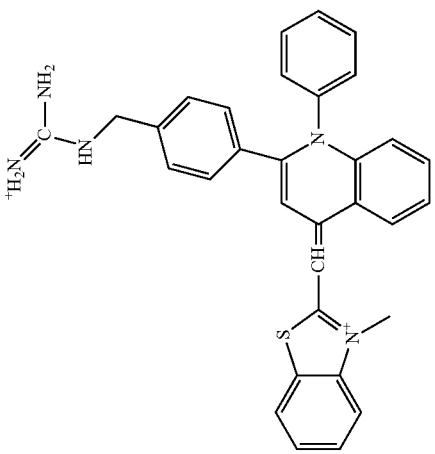 | guanidino |
| 26 | 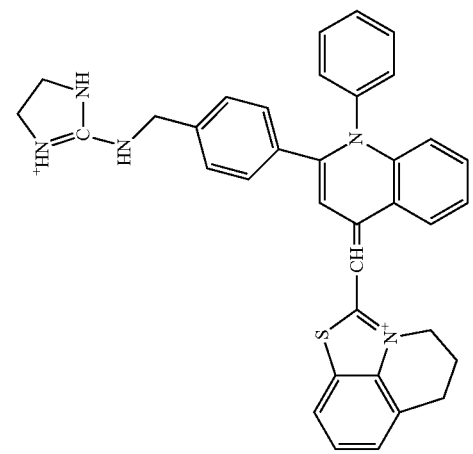 | guanidino |

TABLE 1-continued
Compounds of Formulas 1A and 2A
| Cmpd. No. | Structure* | Description of $G_1$ or V moiety |
|---|---|---|
| 27 | 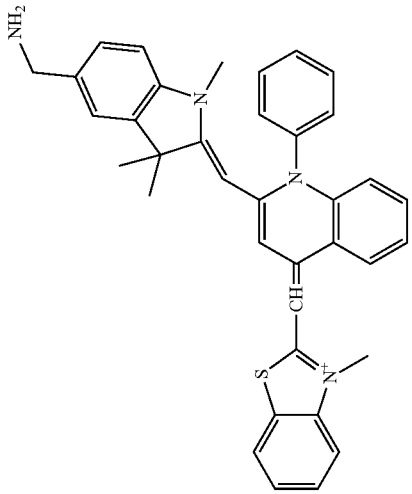 | Substituted vinyl |
| 28 | 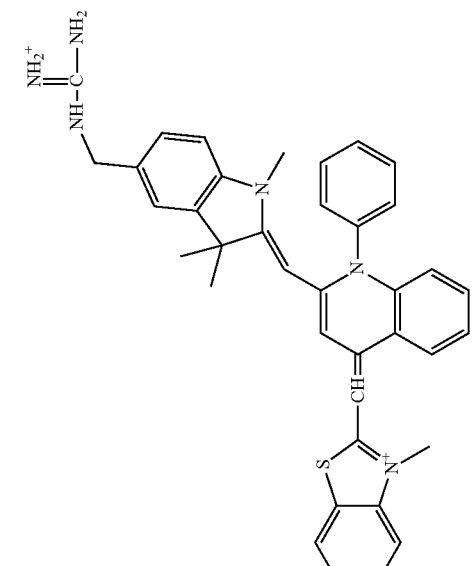 | Guanidino and substituted vinyl |

TABLE 1-continued

Compounds of Formulas 1A and 2A

| Cmpd. No. | Structure* | Description of $G_1$ or V moiety |
|---|---|---|
| 29 | 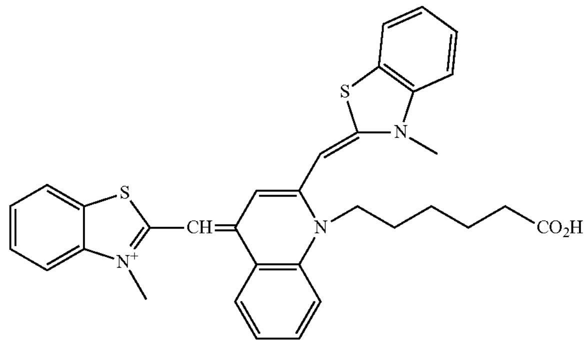 [SMILES: CN1/C(=C\C2=CC(=Cc3sc4ccccc4[n+]3C)c3ccccc3N2CCCCCC(=O)O)Sc2ccccc21] | Substituted vinyl (and -L$_2$- reactive group) |
| 30 | 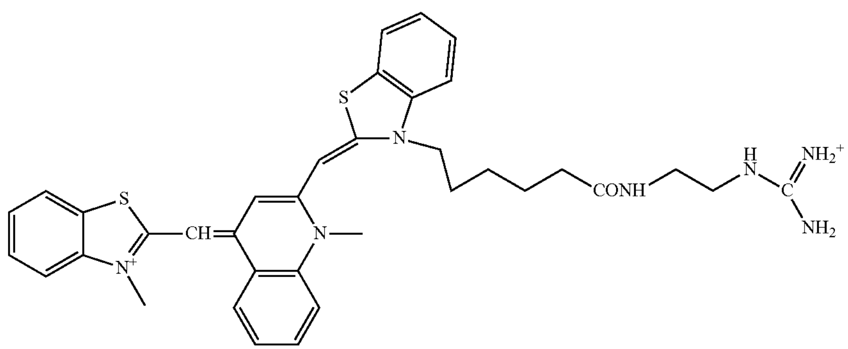 | Substituted vinyl and guanidino |

TABLE 1-continued

Compounds of Formulas 1A and 2A

| Cmpd. No. | Structure* | Description of $G_1$ or V moiety |
|---|---|---|
| 31 | 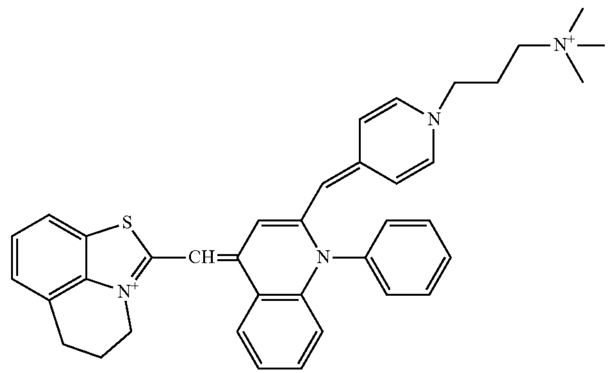 [SMILES: C[N+](C)(C)CCCN1C=CC(=CC2=CC(=Cc3sc4cccc5c4[n+]3CCC5)c3ccccc3N2c2ccccc2)C=C1] | Substituted vinyl |
| 32 | 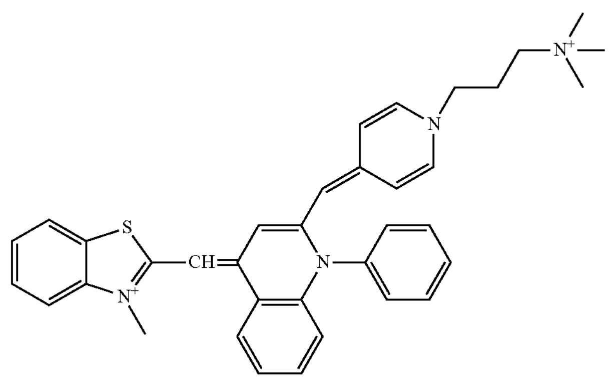 [SMILES: C[n+]1c(C=C2C=C(C=C3C=CN(CCC[N+](C)(C)C)C=C3)N(c3ccccc3)c3ccccc32)sc2ccccc21] | Substituted vinyl |

TABLE 1-continued

Compounds of Formulas 1A and 2A

| Cmpd. No. | Structure* | Description of $G_1$ or V moiety |
|---|---|---|
| 33 | 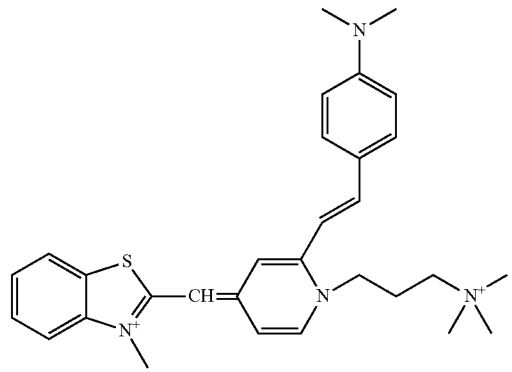 [SMILES: CN(C)c1ccc(/C=C/C2=CC(=Cc3sc4ccccc4[n+]3C)C=CN2CCC[N+](C)(C)C)cc1] | Substituted vinyl |
| 34 | 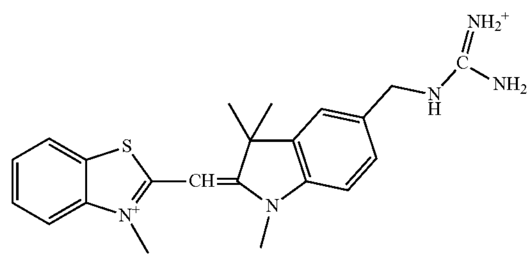 [SMILES: CN1C(=Cc2sc3ccccc3[n+]2C)C(C)(C)c2cc(CNC(N)=[NH2+])ccc21] | guanidino |
| 35 | 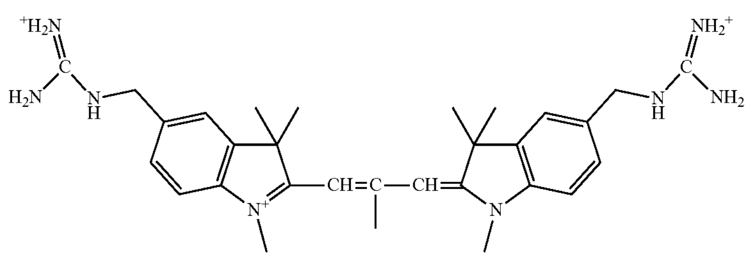 [SMILES: CC(=CC1=[N+](C)c2ccc(CNC(N)=[NH2+])cc2C1(C)C)C=C1N(C)c2ccc(CNC(N)=[NH2+])cc2C1(C)C] | guanidino |

TABLE 1-continued

Compounds of Formulas 1A and 2A

| Cmpd. No. | Structure* | Description of $G_1$ or V moiety |
|---|---|---|
| 36 | 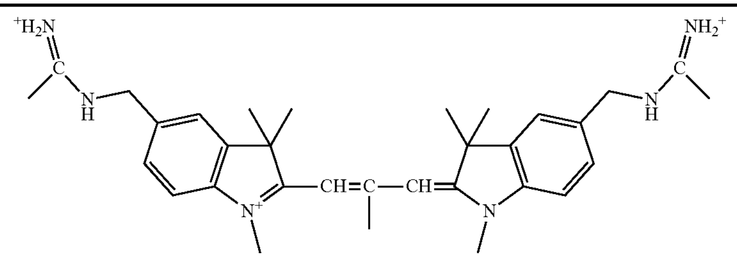 | amidino |
| 37 | 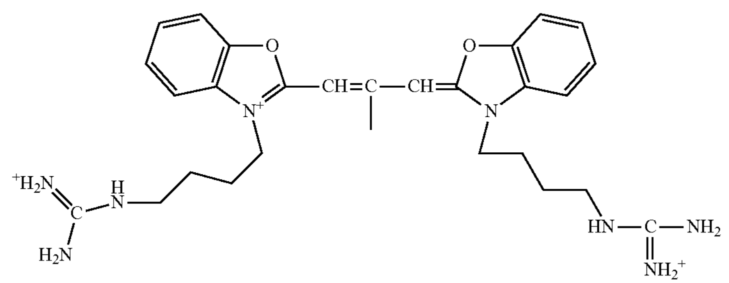 [SMILES: CC(=Cc1oc2ccccc2[n+]1CCCCNC(N)=[NH2+])C=C1Oc2ccccc2N1CCCCNC(N)=[NH2+]] | guanidino |
| 38 | 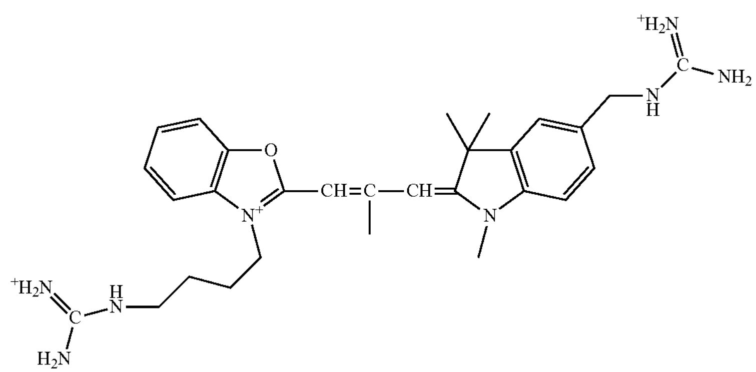 [SMILES: CC(=Cc1oc2ccccc2[n+]1CCCCNC(N)=[NH2+])C=C1N(C)c2ccc(CNC(N)=[NH2+])cc2C1(C)C] | guanidino |

TABLE 1-continued

Compounds of Formulas 1A and 2A

| Cmpd. No. | Structure* | Description of $G_1$ or V moiety |
|---|---|---|
| 39 | 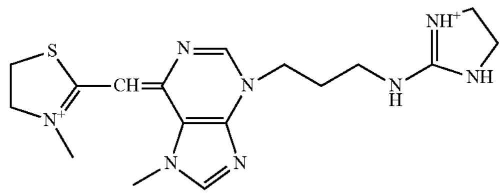 [SMILES: Cn1cnc2c1C(=CC1=[N+](C)CCS1)N=CN2CCCNC1=[NH+]CCN1] | Cyclic guanidino |
| 40 | 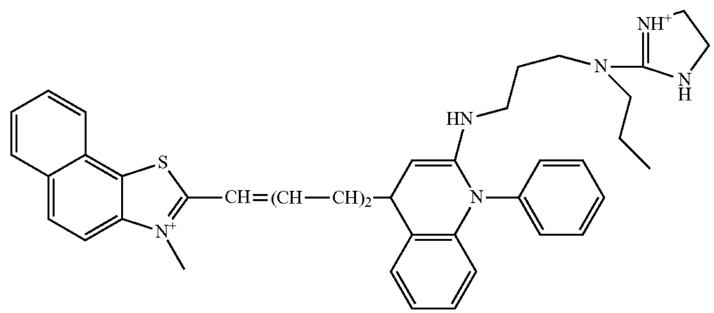 | Substituted cyclic guanidino |
| 41 | 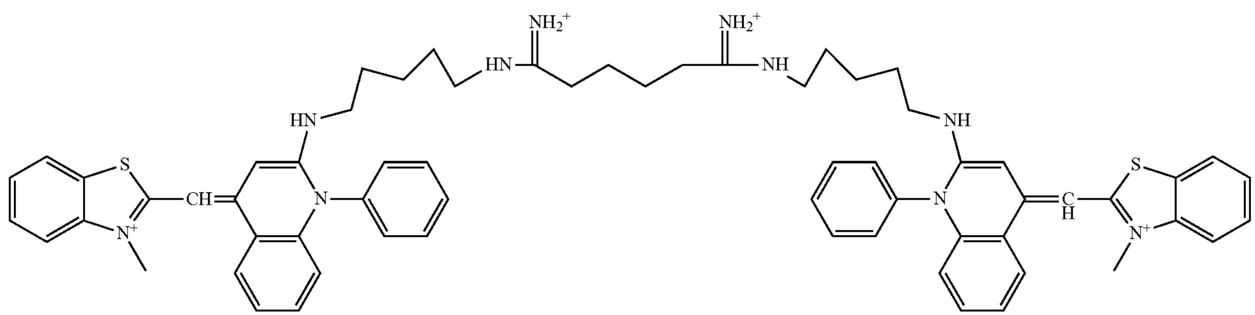 [SMILES: C[n+]1c(C=C2C=C(NCCCCCNC(=[NH2+])CCCCC(=[NH2+])NCCCCCNC3=CC(=Cc4sc5ccccc5[n+]4C)c4ccccc4N3c3ccccc3)N(c3ccccc3)c3ccccc32)sc2ccccc21] | Substituted amidino ($-L_2-G_2$) |

*For simplicity, any counter ion necessary for balancing the charge of the dye is not shown. In general, any biologically compatible counter ion is suitable.

In some preferred embodiments, Formula 1B may be reduce to the more specific structures of Formula 2B below:

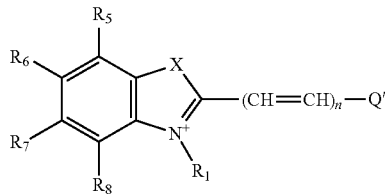

Formula 2B

Examples of dyes according to Formula 1B and Formula 2B are listen in Table 2 below:

red-shifted (i.e., shifted to longer wavelengths) by using one or more of the following structure elements: a) $R_a$ and $R_b$ form a bicyclic fused ring (compound 40 of Table 1); b) X as a vinylene (compound 45 of Table 2) or dialkyl-substituted methylene (compounds 35 and 36 of Table 1 and compounds 44 and 46 of Table 2); c) n as 2 (compound 40 of Table 1 and compound 45 of Table 2); and d) Q as a fused bicyclic ring comprising only one nitrogen atom (compounds 5, 6, 7, 8, 9, 10, 26, 27, 28, 29, 30, 31, 32, and 40). Likewise, the spectra of dyes of the invention may be blue-shifted (i.e., shifted to shorter wavelengths) by selecting one or more of the following structure elements: a) W as a single bond (compound 39 of Table 1); b) X as O (compounds 15, 16, 37 and 38 of Table 1); n as 0 for dyes of Formula 1A (compounds 1-34, 39 and 40 of Table 1); and

TABLE 2

Compounds of Formula 1B and Formula 2B

| Cmpd. No. | Structure* | Description of $G_1$ moiety |
|---|---|---|
| 42 | 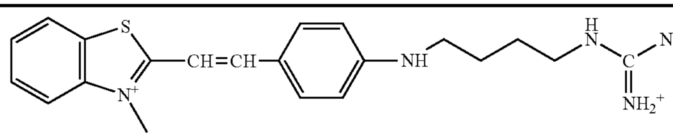 | guanidino |
| 43 | 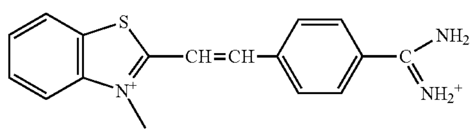 [SMILES: C[n+]1c(C=Cc2ccc(C(N)=[NH2+])cc2)sc2ccccc21] | amidino |
| 44 | 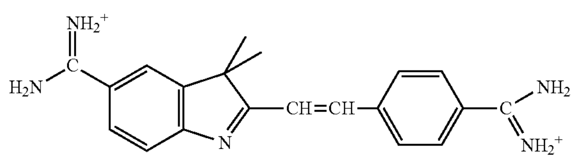 [SMILES: CC1(C)C(C=Cc2ccc(C(N)=[NH2+])cc2)=Nc2ccc(C(N)=[NH2+])cc21] | amidino |
| 45 | 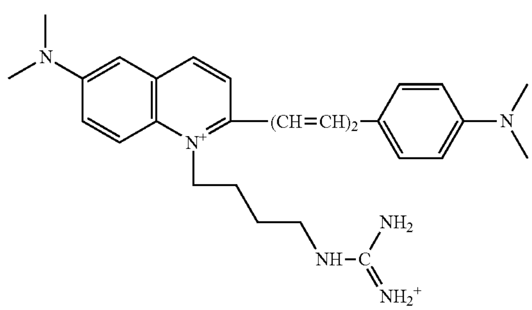 | guanidino |
| 46 | 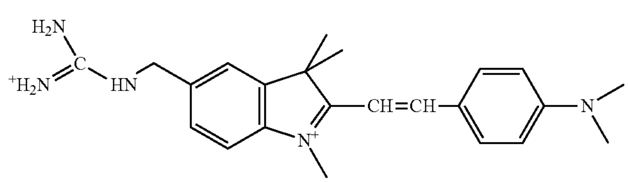 [SMILES: CN(C)c1ccc(C=CC2=[N+](C)c3ccc(CNC(N)=[NH2+])cc3C2(C)C)cc1] | guanidino |

*For simplicity, any counter ion necessary for balancing the charge of the dye is not shown. In general, any biologically compatible counter ion is suitable.

The chemical structure elements X, a, n, $L_1$, $L_2$, $L_3$, Q, Q' and the various substituents in formulas 1A, 1B, 2A and 2B impart various desirable physical, chemical and biological properties to the dyes. In general, the nature of X, n, Q and Q' and various R groups can significantly affect the absorption and emission wavelengths (i.e., the color) of the compounds. For example, the spectra of a compound can be Q as a mono-heterocycle comprising at least two nitrogen atoms (compounds 1 and 2 of Table 1). One skilled in the art can readily appreciate that by selecting various combination of aforementioned structure elements compounds of different wavelengths may be prepared. In particular, one may prepare a compound of the invention having absorption and emission wavelengths to best match with the optical detection system of an instrument on which the compound is to be used. By way of example, a compound of the invention may have an absorption maximum centered at around 470 nm and emission maximum at around 520 nm (e.g. compound 5). Traditionally, green fluorescent dyes, such as FITC, EvaGreen, SYBR Green, CF488A, and Alexa Fluor 488, are excited by a 488 nm argon laser line, and detected in an optical window typically set from about 510 nm to about 530 nm on many bioanalytical instruments. Although the argon laser can efficiently excite these green dyes, it is expensive and has a relatively short lifetime. As a result, the optical excitation sources on many modern fluorescence analytical instruments are now based on light emitting devices or LEDs. For example, blue LEDs have been used to replace the 488 nm argon laser on many of the bioanalytical instruments. Compared to the traditional lasers, LEDs have many advantages, including low cost, long lifetime, high energy efficiency, fast-switching (i.e., near zero warm-up time), and small sizes. However, the most common blue LED to replace the 488 nm argon laser has a peak wavelength centered at around 470 nm, which is nearly 20-30 nm off from the absorption maxima of the widely used green fluorescent dyes, resulting in inefficient excitation and thus relatively weak fluorescence. Some of the compounds of the invention have an absorption maximum at around 470 nm and emission maximum at around 520 nm, making the compounds ideal for the blue LED-equipped analytical instruments.

Various substituents are disclosed for Formulas 1A, 1B, 2A and 2B. In some embodiments, such substituents may affect the nucleic acid binding mode of the compounds. For example, substitution of $R_6$ or $R_7$ in Formula 2A by a heteroaryl, such as a benzothiazolyl, may render the compound to be a DNA minor groove binder as described in U.S. Pat. No. 7,378,240. Direct substitution of Q by a nitro may make the compound a fluorescence quencher, which may be useful in analyte detection via fluorescence resonance energy transfer (FRET) as described in U.S. Pat. No. 6,541,618.

In some cases, a substituent of Formula 1A or 1B may comprise a reactive group. Herein, the term "reactive group" generally refers to a chemical moiety capable of undergoing chemical reaction under relatively mild condition, such as within a temperature range from about 0° C. to about 50° C., more typically from about 4° C. to about 37° C. with or without a catalyst or a coupling agent or activation by light. In general, the chemical reaction herein is a chemical conjugation reaction resulting in the covalent attachment of the compound to another substrate molecule having a suitable functional group for reacting with the reactive group of the compound. The conjugation reaction may take place in an organic solvent or in a biological buffer. Reactive groups suitable for the invention include, but not limited to, those described in U.S. Pat. No. 5,863,753. Additional reactive groups are described below in the section titled "Reactive groups". Examples of substrate molecules that can be labeled include but are not limited to protected or unprotected nucleosides, nucleotides, oligonucleotides, particles, microsphere beads, peptides and proteins. Labeled protected nucleosides may be useful for preparing oligonucleotides on oligo synthesizers. Labeled oligonucleotides can be enzymatically incorporated into oligonucleotides. Labeled oligonucleotides, such as labeled primers or probes, may be used in nucleic acid amplification reactions, such as real-time PCR. Labeled oligonucleotides may also be useful as hybridization probes in detecting a target nucleic acid.

Some compounds of Formulas 1A and 1B may comprise a vinyl substituent V as defined previously herein. In some embodiments, a substituent V has the effect of red-shifting the wavelengths of the compound, for example by at least 5, 10, 15, 20, 25 or 30 nm or more.

Some of the substituents of Formulas 1A, 1B, 2A and 2B may comprise a positively charged moiety, which has the effect of enhancing the nucleic acid binding affinity of the compound via electrostatic interaction between the negatively charged phosphate backbone of nucleic acid and the positive charge of the moiety. The positively charged moiety may be a protonated amine (i.e., a primary, secondary or tertiary amine), a trialkylammonium, or a $G_1$ moiety. An amine is generally considered to be a weak base, only a fraction of which is protonated under physiological condition to result in a positive charge. The extend of amine protonation is a function of the relative basicity of the amine and the exact physiological pH. A tertiary amine is generally a stronger base than a secondary amine, which is a stronger base than a primary amine. Thus, the extend of protonation is in the order of: tertiary amine>secondary amine>primary amine. On the other hand, a trialkylammonium group is a fully and permanently positively charged moiety independent of physiological pH. As a result, trialkylammonium moieties have frequently been incorporated into nucleic acid binding dyes to enhance nucleic acid binding via electrostatic interaction (U.S. Pat. Nos. 5,321,130; 5,436,134; 5,545,535 and 7,456,281; and WO2008052742). While nucleic acid dyes comprising a trialkylammonium possess high binding affinity, which is important for some applications, they may not be suitable for detecting nucleic acids in live cells because the highly charged trialkylamonium prevents or reduces the dyes' cell membrane permeability. As another example, a DNA dye having too high an affinity may preclude the dye's use in real-time PCR because the dye's tight DNA binding may inhibit PCR. Furthermore, a DNA dye of too high an affinity may not be suitable for so-called high resolution melt curve (HRM) analysis, which typically requires a relatively high concentration of the dye in PCR (U.S. Pat. No. 7,387,887). A protonated amine, however, is not permanently positively charged due to the rapid chemical equilibrium between the protonated and unprotonated forms of the amine. For this reason, nucleic acid dyes suitable for detecting nucleic acids in live cells generally comprise a protonatable amine side chain both for sufficient affinity and cell membrane permeability. In some cases, a protonatable amine side chain may be sufficient (but not necessarily optimal) for a compound to have an acceptable DNA binding affinity for a particular application. For example, SYBR Green I, an asymmetric cyanine dye with a tertiary amine side chain, is a widely used dye in real-time PCR (Zipper, Brunner et al. 2004).

Some compounds of the present invention comprise a substituent comprising a $G_2$ moiety selected from the group consisting of substituted or unsubstituted guanidino, substituted or unsubstituted amidino, substituted or unsubstituted hydrazinoalkyl, substituted or unsubstituted aminooxy and substituted or unsubstituted hydroxylamino. Like an amine side chain, a $G_1$ typically exists as a mixture of two forms in a physiological buffer: protonated and unprotonated forms, where the two forms are in fast equilibrium. However, the unprotonated form of a $G_1$ is significantly more basic than a typical unprotonated amine. Because of the high basicity, in common biological buffers a $G_1$ of the invention is primarily in the protonated form as depicted below for guanidino and amidino group:

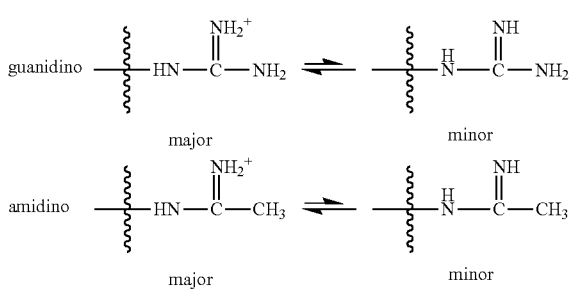

Chemical structures of guanidino and amidino groups are generally drawn as the protonated form throughout this invention disclosure. The higher degree of protonation of guanidino and amidino than an amine side chain also makes guanidino and amidino more effective than the latter in enhancing the nucleic acid binding of compounds in the present invention via electrostatic interaction. Furthermore, amidino and guanidino, in particular, comprise multiple nitrogen atoms and acidic protons, which make amidino and guanidino good hydrogen bond acceptors and donors. Thus, in addition to electrostatic interaction, hydrogen bonding between the guanidino or amidino and the nucleic acid backbone may also play a role in enhancing the nucleic acid binding affinity of the compounds. These collective properties of guanidino and amidino make them superior alternative to an amine side chain in the context of nucleic acid dyes.

Despite having a high degree of protonation, dyes of the invention comprising a $G_1$ can still freely cross cell membranes to stain the nuclei of live cells, unlike asymmetric cyanine dyes having a quaternized side chain (U.S. Pat. No. 5,321,130), which have enhanced nucleic acid binding affinity but cannot stain live cells. This unique property may make compounds of the invention useful for highly sensitive cell number quantification via intracellular nucleic acid detection without the need of lysing the cells.

For some nucleic acid detection applications, the nucleic acid binding affinity of the dye may have to be within a particular range. For example, for qPCR or real-time PCR application, a relatively moderate DNA binding affinity is desirable as too low an affinity may not provide sufficient fluorescence brightness while too high an affinity can cause PCR inhibition. In general, a proper DNA binding affinity can be achieved by modifying the dye core structure with a suitable substituent. Substituents comprising a $G_2$ moiety of the invention add to the collection of substituents useful for modulating the nucleic acid binding affinity of compounds, increasing the chance for one to obtain improved physiochemical properties. It is a discovery of the invention that compounds comprising a $G_2$ moiety according to the invention are highly sensitive nucleic acid stains suitable for a variety of applications including but not limited to routine nucleic acid quantitation in solution, cell number determination, gel staining, qPCR and post PCR DNA melt curve analysis.

Nucleic Acid Binding Dyes

Nucleic acid binding dyes are generally capable of binding to DNA, RNA, or to a hybrid thereof. For example, a nucleic acid binding dye can be an intercalating dye or a minor groove binding dye. The nucleic acid binding dye can be a fluorescent dye. The fluorescent dye may display different fluorescence spectra depending on whether it is bound or not bound to a double-stranded nucleic acid molecule. For example, the nucleic acid binding dye may be substantially non-fluorescent when uncomplexed with a double-stranded nucleic acid molecule and becomes substantially fluorescent when complexed with a double-stranded nucleic acid molecule. Suitable nucleic acid dyes include many commercially available dyes and those known in the art.

As used herein, an intercalating dye can be capable of non-covalent insertion between stacked base pairs in the nucleic acid double helix. Intercalating agents, such as ethidium bromide, fluoresce more intensely when intercalated into double-stranded DNA than when bound to single-stranded DNA, RNA, or in solution. Other intercalating agents exhibit a change in the fluorescence spectra when bound to double-stranded DNA. For example, actinomycin D fluoresces red when bound to single-stranded nucleic acids, and green when bound to a double-stranded template. Whether the detectable signal increases, decreases or is shifted, as is the case with actinomycin D, any intercalating agent that provides a detectable signal that is distinguishable when the agent is bound to double-stranded DNA or unbound is suitable for practicing the disclosed invention. For example, the interaction between DNA and another photoreactive psoralen, 4-aminomethyle-4-5'8-trimethylpsoralen (AMT) has been described (see Johnson et al. 1981, Photochem. & Photobiol., 33:785-791, which is incorporated herein by reference). According to the reference, both the absorption at long wavelengths and fluorescence, decline upon intercalation of AMT into the DNA helix. U.S. Pat. Nos. 4,582,789 and 5,994,056 describe several intercalating moieties including psoralens, which are both incorporated herein by reference.

Non-intercalating DNA binding agents are also suitable. For example, Hoechst 33258 (Searle & Embrey, 1990, Nuc. Acids Res. 18(13):3753-3762) exhibits altered fluorescence with increasing amount of target. Hoechst 33258 is a member of a class of nucleic acid-binding compounds commonly referred to as "groove binders" that bind to the groove region of a helical nucleic acid molecule. This group includes drugs like distamycin, netropsin and others. These compounds typically recognize and bind to the minor groove of a helical nucleic acid molecule such as a double-stranded DNA.

The nucleic acid binding dyes may not be complexed with other moieties, such as polynucleotides, polypeptides, and/or dye modifiers. The dye can be a free dye that is not complexed to a binding moiety, such as a binding moiety that exhibits binding to the target analyte. These binding moieties can include antibodies or DNA probes that may or may not exhibit binding to the target analyte.

Suitable nucleic acid binding dyes include dsDNA-selective and RNA-selective dyes. More specific examples of suitable nucleic acid dyes include, but are not limited to, EvaGreen dye, GelRed, GelGreen, SYBR Green I (U.S. Pat. Nos. 5,436,134 and 5,658,751), SYBR GreenEr, SYBR Gold, LC Green, LC Green Plus, BOXTO, BEBO, SYBR DX, SYTO9, SYTOX Blue, SYTOX Green, SYTOX Orange, SYTO dyes, POPO-1, POPO-3, BOBO-3, YOYO-1, YOYO-3, TOTO-1, TOTO-3, PO-PRO-1, BO-PRO-1, YO-PRO-1, TO-PRO-1, JO-PRO-1, PO-PRO-3, LO-PRO-1, BO-PRO-3, YO-PRO-3, TO-PRO-3, TO-PRO-5, Ethidium Homodimer-1, Ethidium Homodimer-2, Ethidium Homodimer-3, propidium iodide, ethidium bromide, various Hoechst dyes, DAPI, ResoLight, Chromofy, and acridine homodimer. Merely by way of example, fluorescent RNA- or ssDNA-binding dyes include SYBR Green II, OliGreen, and RiboGreen. Other nucleic acid dyes include those disclosed in U.S. Pat. No. 4,883,867 to Lee (1989), U.S. Pat.

No. 5,582,977 to Yue et al. (1996), U.S. Pat. No. 5,321,130 to Yue et al. (1994), and U.S. Pat. No. 5,410,030 to Yue et al. (1995), and U.S. Pat. No. 5,863,753 and U.S. patent application Ser. Nos. 11/377,253, 11/952,867. Many of the above mentioned dyes are commercially available from Invitrogen, Sigma, Biotium and numerous other companies.

Reactive Groups

Compounds of the invention may comprise a reactive group. A reactive group is a chemical moiety capable of reacting with a reaction partner on a substrate or substrate molecule to form a covalent bond. A compound of the invention can be used to label a wide variety of molecules or substrates that contain a suitable reaction partner or are derivatized to contain a suitable reaction partner. "Reactive group" and "reaction partner" may refer to groups on a compound of the present invention, or to groups on a molecule to be labeled. Here, by way of convenience, but not limitation, a bond-forming group on a compound will generally be referred to as a reactive group and a bond-forming group on the substrate molecule will generally be referred to as a reaction partner. "Reaction substrate", "substrate" and "reaction partner" are used interchangeably throughout this document.

The reactive group and its reaction partner may be an electrophile and a nucleophile, respectively, that can form a covalent bond with or without a coupling agent or catalyst. According to one embodiment, the reactive group is a photoactivatable group capable of reacting with a hydrocarbon molecule upon ultraviolet photoactivation or photolysis. According to another embodiment, the reactive group is a dienophile capable of reacting with a conjugated diene via a Diels-Alder reaction. According to yet another embodiment, the reactive group is a 1,3-diene capable of reacting with a dienophile. According to still another embodiment, the reactive group is an alkyne capable of reacting with an azido functional group to form a 1,2,3-triazole linkage. According to still another embodiment, the reactive group is a 2-(diphenylphosphino)benzoic acid methyl ester capable of reacting with an azido functional group to form an amide linkage via so-called Staudinger reaction. Merely by way of example, examples of useful reactive groups, functional groups, and corresponding linkages according to the present invention are listed below in Table 3.

TABLE 3

Examples of Reactive Groups, Functional Groups, and Covalent Linkages

| Reactive Group | Reaction Part/Substrate | Resulting Covalent Linkage |
| --- | --- | --- |
| activated esters * | amines/anilines | Carboxamides |
| acrylamides | Thiols | Thioethers |
| acyl azides** | amines/anilines | Carboxamides |
| acyl halides | amines/anilines | Carboxamides |
| acyl halides | Alcohols/phenols | Esters |
| acyl nitriles | Alcohols/phenols | Esters |
| acyl nitriles | amines/anilines | Carboxamides |
| aldehydes | amines/anitines | Imines |
| aldehydes or ketones | Hydrazines | Hydrazones |
| aldehydes or ketones | Hydroxylamines | Oximes |
| alkyl halides | amines/anilines | alkyl amines |
| alkyl halides | Thiols | Thioethers |
| alkyl halides | alcohols/phenols | Esters |
| alkyl sulfonates | Thiols | Thioethers |
| alkyl sulfonates | carboxylic acids | Esters |
| alkyl sulfonates | alcohols/phenols | Esters |
| anhydrides | alcohols/phenols | Esters |

TABLE 3-continued

Examples of Reactive Groups, Functional Groups, and Covalent Linkages

| Reactive Group | Reaction Part/Substrate | Resulting Covalent Linkage |
| --- | --- | --- |
| anhydrides | amines/anilines | Carboxamides |
| aryl halides | Thiols | Thiophenols |
| aryl halides | Amines | aryl amines |
| aziridines | Thiols | Thioethers |
| boronates | Glycols | boronate esters |
| epoxides | Thiols | Thioethers |
| haloacetamides | Thiols | Thioethers |
| halotriazines | amines/anilines | Aminotrizaines |
| halotriazines | alcohols/phenols | triazinyl ethers |
| imido esters | amines/anilines | Amidines |
| isocyanates | amines/anilines | Ureas |
| isocyanates | alcohols/phenols | Urethanes |
| isothiocyanates | amines/anilines | Thioureas |
| maleimides | Thiols | Thioethers |
| phosphoramidites | Alcohols | phosphite esters |
| silyl halides | Alcohols | silyl ethers |
| sulfonate esters | amines/anilines | alkyl amines |
| sulfonate esters | Thiols | Thioethers |
| sulfonate esters | Alcohols | Ethers |
| sulfonyl halides | amines/anilines | Sulfonamides |
| sulfonyl halides | phenols/alcohols | sulfonate esters |
| azide | alkyne | 1,2,3-triazole |
| Cis-platinum | guanosine | Platinum-guanosine complex |

* Activated esters, as understood in the art, generally have the formula COΩ, where Ω is a good leaving group, stich as succinimidyloxy (–OC$_4$H$_4$O$_2$)), sulfosuccinimidyloxy (–OC$_4$H$_3$O$_2$–SO$_3$H), or 1-oxybenzotriazolyl (–OC$_6$H$_4$N$_3$), the example; or an aryloxy group or aryloxy substituted one or more times by electron-withdrawing substituent(s), such as nitro, fluoro, chloro, cyano, trifluoromethyl, or combinations thereof for example, used to form activated aryl esters; or a carboxylic acid activated by a carbodiimide to form an anhydride or mixed anhydride –OCOR$^a$ or –OCNR$^a$NHR$^b$, where R$^a$ and R$^b$, which may be the same or different, are independently C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl.
**Acyl azides can also rearrange to isocyanates.

The reactive group may be one that will react with an amine, a thiol, a hydroxyl or an aldehyde. The reactive group may be an amine-reactive group, such as a succinimidyl ester (SE), for example, or a thiol-reactive group, such as a maleimide, a haloacetamide, or a methanethiosulfonate (MTS), for example, or an aldehyde-reactive group, such as an amine, an aminooxy, or a hydrazide, for example.

Compound Synthesis

The chemical structure of a compound of the invention may be viewed to comprise two parts: the compound core structure and the various substituents attached to the core structure. The core structure, as defined for example by Formula 1A or, more specifically, by Formula 2A is generally referred to as the core structure of cyanine dyes or asymmetric cyanine dyes. Similarly, the core structure defined by Formula 1B or, more specifically, by Formula 2B is generally referred to as the core structure of merocyanine dyes. Compounds sharing the same core structure generally can be prepared by following similar synthesis procedures and using starting materials with appropriate substituents. Thus, compounds of Formula 1A or 2A may be prepared using procedures previously developed for compounds of similar core structures, such as the procedures described in U.S. Pat. Nos. 5,582,977; 5,656,449; 5,658,751; and 7,456, 281 and the procedures described by Moreda and Forrester (Moreda 1997) for preparing compounds wherein Q comprises multiple nitrogen atoms in the aromatic ring system.

A key step in assembling the compound core structures is the reaction of a first quaternized heterocycle bearing an acidic methyl group at the 2- or 4-position (relative to the quaternary nitrogen) with a second quaternized heterocycle bearing a leaving group at the 2- or 4-position (relative to the quaternary nitrogen) as illustrated by the example below (Scheme 1):

Scheme 1

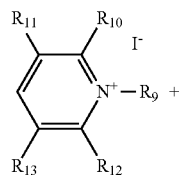

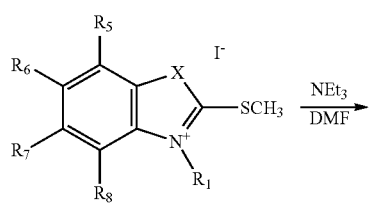

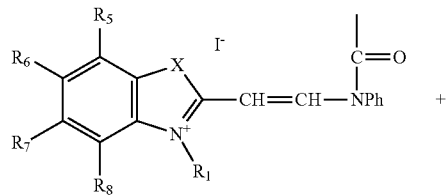

For the preparation of long wavelength dyes, the leaving group is typically on a vinyl or polyvinyl substituent at the 2- or 4-position of the second quaternized heterocyle as shown by the example below (Scheme 2):

Scheme 2

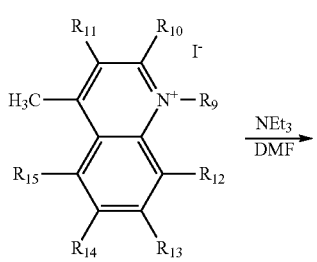

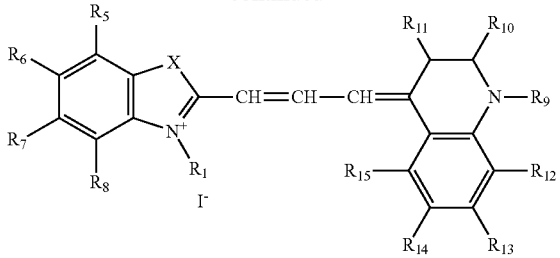

The reaction is generally promoted by the addition of a base, which deprotonates the acidic methyl group to form a nucleophilic methylene group, which displaces the leaving group of the second quaternized heterocycle to form the compound.

Likewise, compounds of Formula 1B or 2B may be prepared by following the general procedures known for compounds of similar core structures (Ishchenko 2009). These compounds are typically prepared by condensing a quaternized heterocyle bearing a 2- or 4-methyl group with an aryl aldehyde, arylvinyl aldehyde or arylpolyvinyl aldehyde in the presence of a basic catalyst as shown by the example below (Scheme 3):

Scheme 3

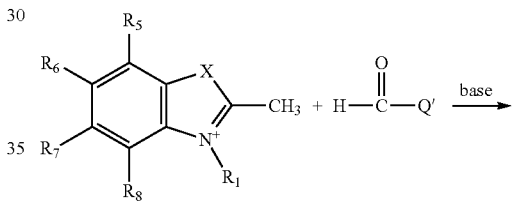

The $G_1$ or V moiety may be incorporated into a compound of the invention at any stage of the compound synthesis process. In some cases, the moiety is incorporated into one of the quaternized heterocycle starting materials or the aldehyde starting material mentioned above. In some other cases, the moiety is incorporated into the compound after the core structure has been assembled. More commonly, an intermediate compound having a readily displaceable substituent at a desired position is first prepared, followed by the displacement of the substituent by a nucleophile comprising $G_1$ or V moiety (Scheme 4).

Scheme 4
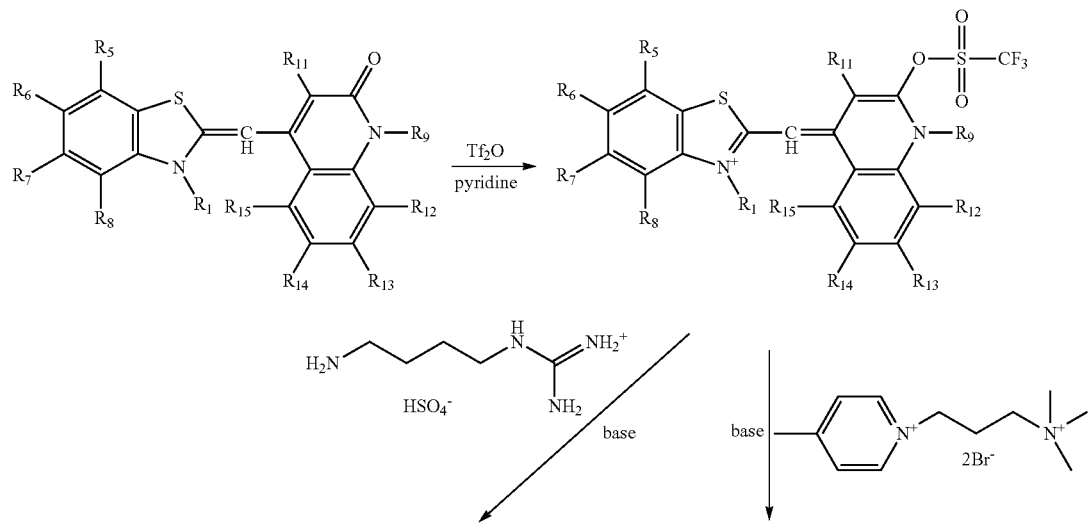
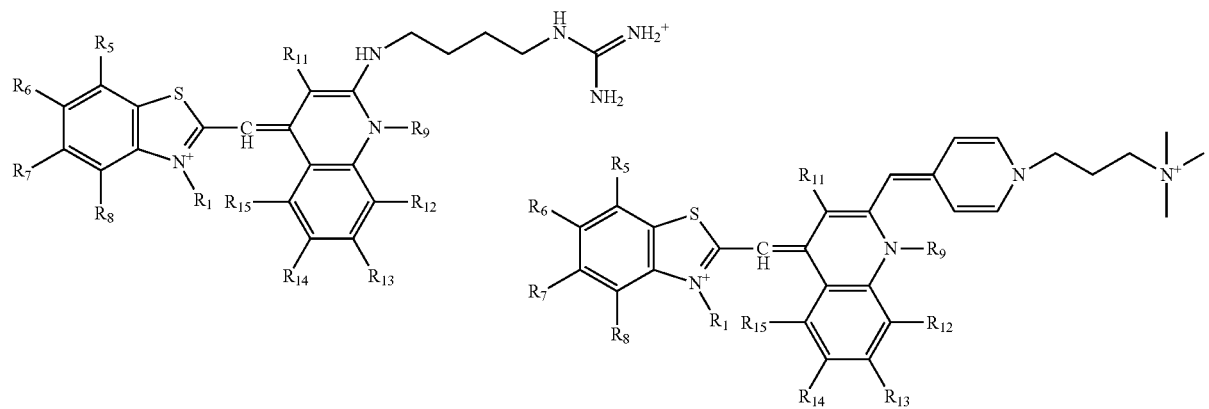

In some cases, the displaceable substituent may be displaced by a nucleophile comprising a precursor $G_1$ or V, followed by conversion of the precursor $G_1$ or V to its final form (Scheme 5):

oligonucleotide (such as a PCR primer or an oligonucleotide probe) via standard phosphoramidite chemistry on an oligo synthesizer.

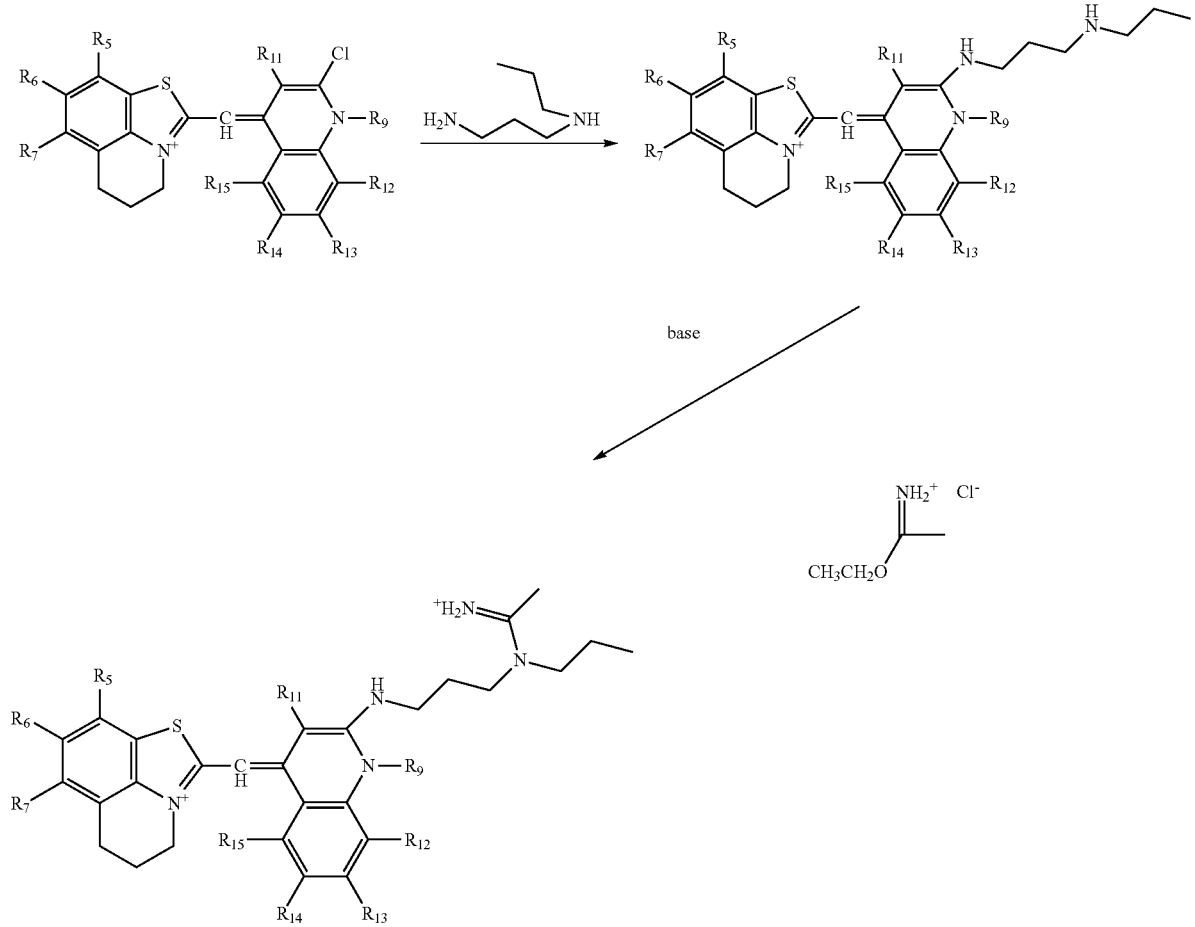

Scheme 5

Some of the compounds according to the invention may comprise a reactive group or a reactive group precursor that can be readily converted to a reactive group in situ using one of many known activating or coupling agents. In general, to prepare a compound comprising a reactive group according to the invention, a precursor reactive group is incorporated into one of the quaternized heterocycle or the aldehyde starting materials mentioned above, or is introduced into a intermediate during the synthesis, followed by conversion of the precursor reactive group into the final reactive group at the last step of the synthesis. Various methods of introducing a reactive group into a nucleic acid binding dye have been further described in U.S. Pat. No. 5,863,753. Compounds of the invention comprising a reactive group can be covalently conjugated to another substrate molecule comprising a suitable functional group. For example, a compound of the invention comprising an activated ester group, such as a succinimidyl ester, can be conjugated to an oligonucleotide comprising an amine group via an amide bond. As another example, a compound of the invention comprising a phosphoramidite can be readily attached to the 5'-end of an To further illustrate the methods for preparing the dyes of the invention, detailed procedures for preparing specific compounds are given in the Example section.

Methods

The compounds described herein can be used for the detection of a target analyte, including but not limited to target nucleic acids and target cells. In some embodiments of the invention, the compounds allow for improved detection of a target analyte by improving the sensitivity, the detection limit, range of linear detection, or range of dynamic response of the compounds to the concentration of a target analyte.

In one embodiment, the present invention provides a method of using the compounds for detecting the presence or absence of a nucleic acid. The method typically comprises the steps of (a) providing at least one compound disclosed herein; (b) in a reaction mixture, allowing said at least one compound to interact with nucleic acids contained within a sample under conditions such that the at least one compound-nucleic acid complexes are formed; and (c) detecting an optical signal in said reaction mixture, said optical signal being indicative of the presence of said nucleic acid.

Figure 4A:
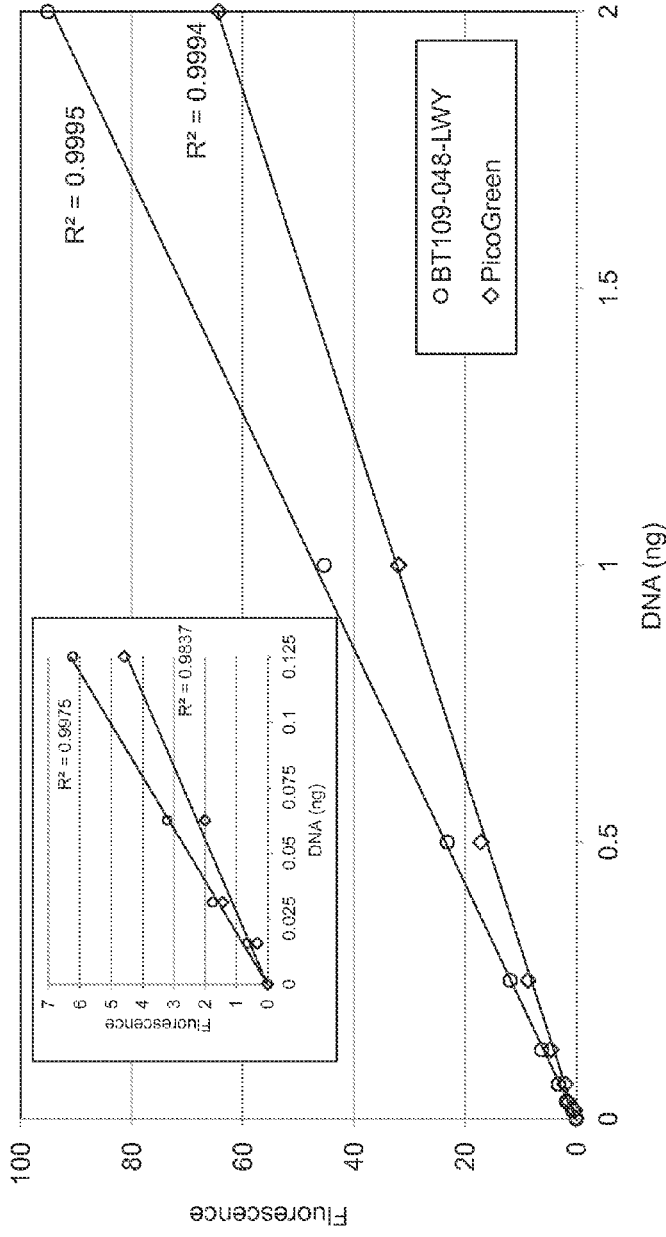
FIG. 4A shows the linearity of fluorescence for compound 7 at 0.5 uM concentration for DNA amounts ranging from 0.015-2 ng compared to PicoGreen dye. Compound 7 can be used to quantitate double-stranded DNA in solution with higher sensitivity and broader linear range compared to PicoGreen. See Example 2 for experimental details.
Figure 4B:
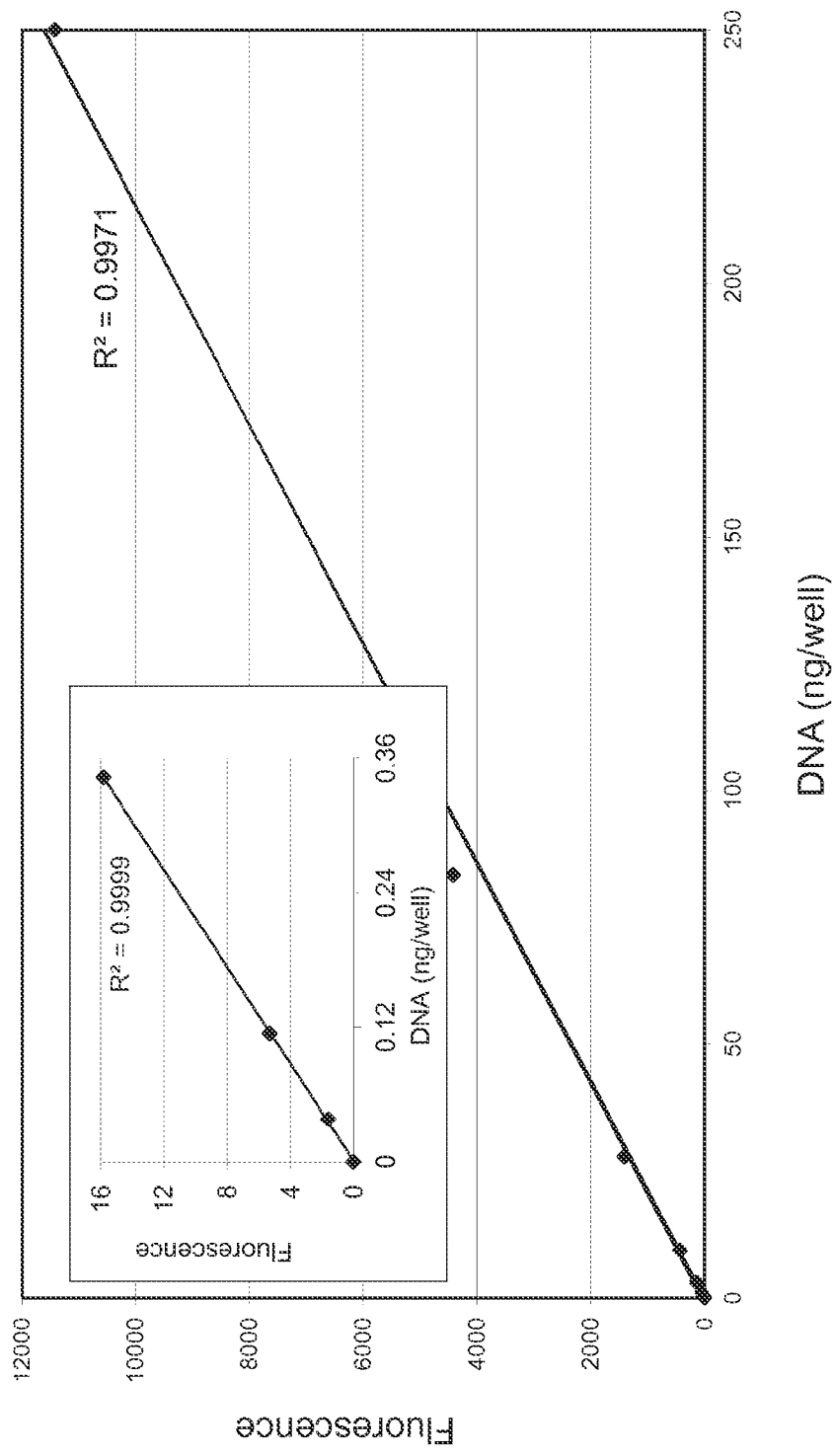
FIG. 4B shows the linearity of fluorescence for compound 5 at 1 uM concentration for DNA amounts ranging from 0.05-250 ng. See Example 2 for experimental details.

The methods of nucleic acid detection can be associated with a variety of practical applications. According to one embodiment, the method is associated with routine quantification of nucleic acid in solution (FIGS. 4A and 4B). Examples of such application include quantifying yields of purified DNA fragments for subcloning or for use as transcription templates, quantifying yields from cDNA library production, quantifying DNA amplification products or DNA input for PCR, detecting DNA contamination in protein drug preparation produced from recombinant organisms, and quantifying forensic DNA samples extracted from various biological samples. The detection of nucleic acid in solution may be performed on a variety of fluorescence-based detection systems, including but not limited to microplate readers, hand-held portable meters, bench-top spectrofluorometers, or instruments that employ microfluidic chips.

In another embodiment, the present invention provides a method for performing a nucleic acid amplification reaction. The method typically comprises (a) conducting a nucleic acid amplification reaction in the presence of at least one compound disclosed herein, which reaction results in an increase in optical signal that is indicative of the presence of amplified nucleic acids; (b) detecting said optical signal. In one aspect, the increase in optical signal is proportional to increase in the amount of amplified nucleic acids resulted from said amplification. As used herein, nucleic acid amplification reaction encompasses PCR, quantitative polymerase chain reaction (qPCR), isothermal nucleic acid amplification, nucleic acid sequencing, ligase chain polymerase chain reaction (LCR-PCR), reverse transcription PCR reaction (RT-PCR), reverse transcription, and nucleic acid ligation.

Figure 8:
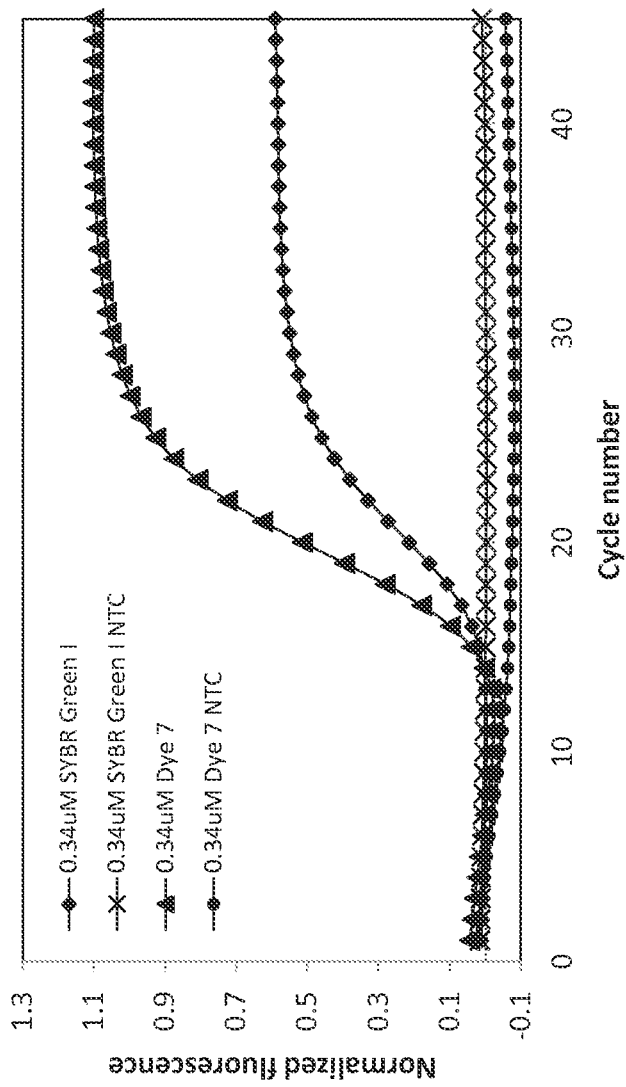
FIG. 8 shows that compound 7 can be used in real time PCR experiments to monitor amplification of target plasmid DNA. See Example 6 for experimental details.
Figure 9:
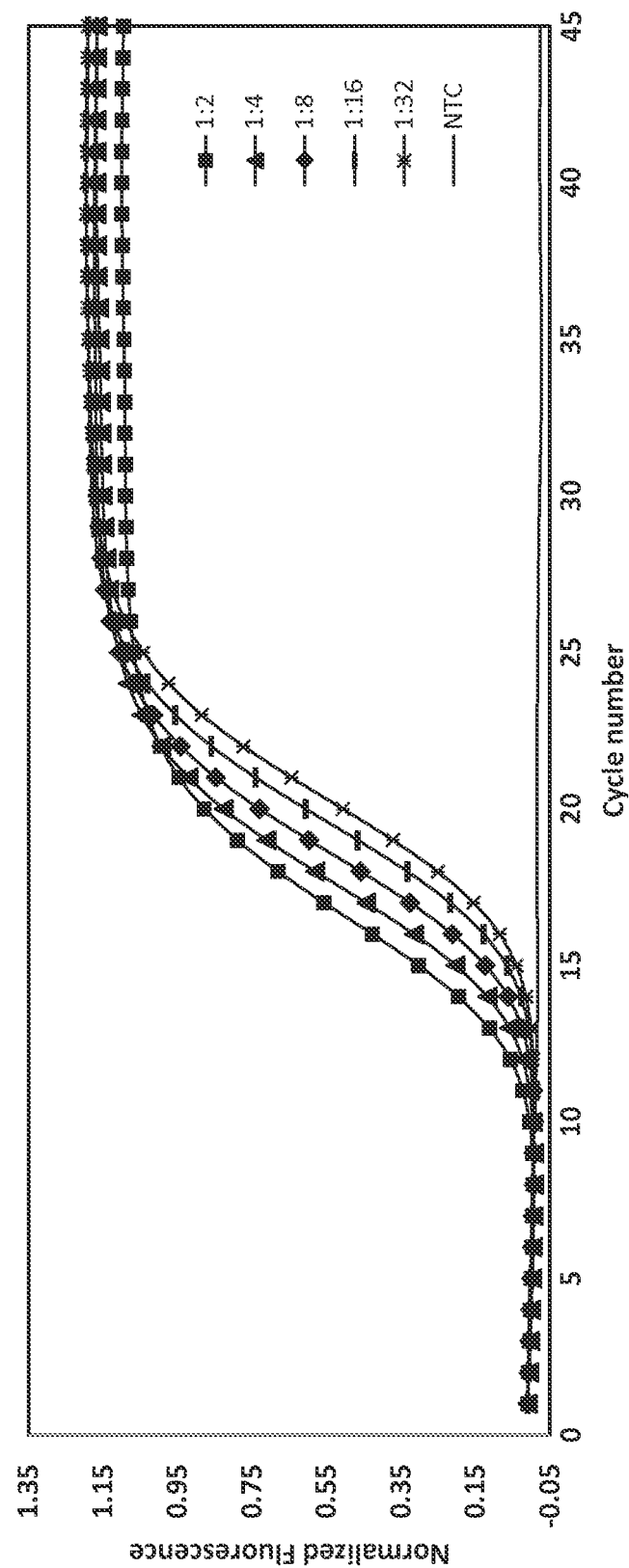
FIG. 9 shows that compound 7 can be used in real time PCR experiments to monitor amplification of target cDNA. See Example 7 for experimental details.

In one embodiment, the subject compounds are used in a real-time polymerase chain reaction (qPCR), wherein the nucleic acid detection agent of the invention detects the amplified PCR products in real-time as the polymerization reaction proceeds (FIGS. 8 and 9). Real-time PCR using a nucleic acid detection agent of the invention may offer a number of benefits. Because compounds of the invention is highly sensitive in detecting nucleic acid, the number of cycle time required for detecting a target nucleic acid (i.e., Ct value) may be reduced and the end-point fluorescence signal is high (FIG. 8).

Figure 10:
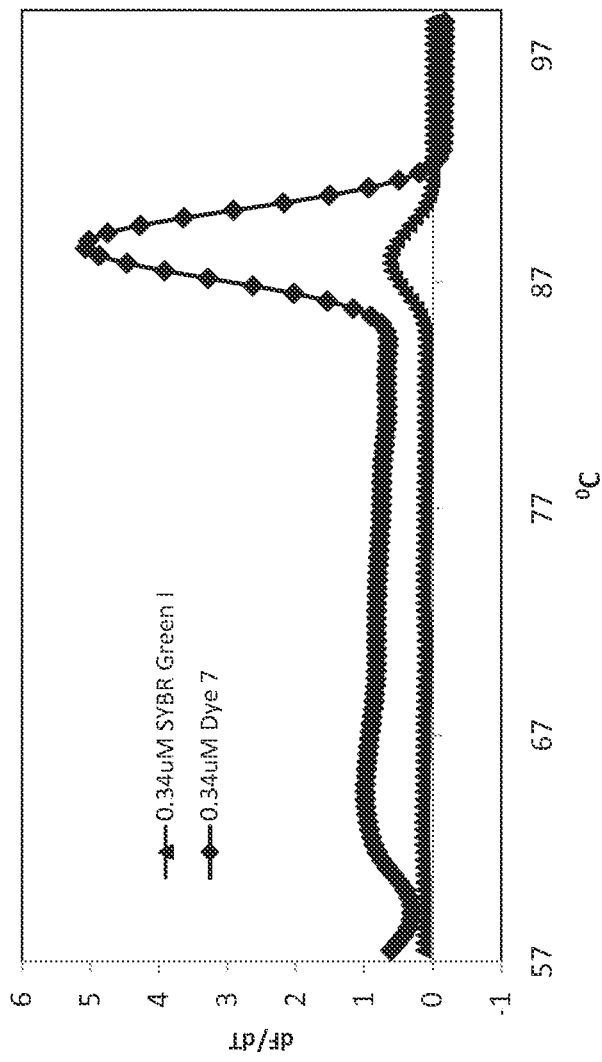
FIG. 10 that compound 7 can be used to perform post-real time PCR melt curve analysis to allow for determination of specific amplification of a target amplicon. See Example 10 for experimental details.

In yet another embodiment, the subject compounds can be used in a DNA melt curve analysis (e.g. as shown in FIG. 10), a technique commonly used to analyze the product of a DNA amplification reaction. The DNA melt curve analysis can be performed on the same reaction mixture used in the nucleic acid amplification reaction. In some embodiments of the invention, no components are added or removed from the reaction mixture between the nucleic acid amplification reaction and the melt curve analysis.

DNA melt curve analysis can reveal the number of DNA species or purity of an amplification reaction, and thus is often used as a more convenient alternative to gel electrophoresis to confirm the specificity of PCR. According to one embodiment, the nucleic acid detection is associated with high resolution melt curve analysis (HRM). Compared to regular DNA melt curve analysis, HRM can yield more information on the amplified DNA product, including the capability for point mutation detection (SNP), zygosity testing and epigenetics analysis. Like regular DNA melt curve analysis, HRM is a post-PCR product analysis method. In HRM, a target nucleic acid is first amplified by PCR in the presence of a DNA binding dye and then the PCR product-dye complex is slowly melted as the fluorescence change is monitored to generate a standard DNA melt curve. The procedure is repeated with additional target nucleic acid(s) to generate additional melt curve(s). The additional melt curve(s) are compared with the standard curve to yield minor differences that may be indicative of mutation site(s) in the target nucleic acid sequences (U.S. Pat. Nos. 7,387,887; 7,456,281; and 7,582,429).

As used herein, the term "$T_m$" can be used in reference to the melting temperature. The melting temperature can be the temperature at which one half of a population of double-stranded polynucleotides or nucleobase oligomers (e.g., hybridization complexes), in homoduplexes or heteroduplexes, become dissociated into single strands. The prediction of a $T_m$ of a duplex polynucleotide can take into account the base sequence as well as other factors including structural and sequence characteristics and nature of the oligomeric linkages.

A $T_m$ can be determined from a melting curve. In some instances, a duplex nucleic acid molecule is heated in a controlled temperature program, and the state of association/dissociation of the two single strands in the duplex is monitored and plotted until reaching a temperature where the two strands are completely dissociated. The $T_m$ can be determined from this melting curve. Alternatively, $T_m$ can be determined by an annealing curve, where a duplex nucleic acid molecule is heated to a temperature where the two strands are completely dissociated. The temperature can then be lowered in a controlled temperature program, and the state of association/dissociation of the two single strands in the duplex is monitored and plotted until reaching a temperature where the two strands are completely annealed. The $T_m$ can be determined from this annealing curve. These methods of determining the melting temperature can be combined or varied. The invention is not limited to any particular method for the determination of $T_m$. Exemplary methods for the experimental determination of $T_m$ are described in a variety of sources, e.g., Liew et al., "Genotyping of Single-Nucleotide Polymorphism by High-Resolution Melting of Small Amplicons," Clinical Chemistry 50(7):1156-1164 (2004); Reed and Wittwer, "Sensitivity and Specificity of Single-Nucleotide Polymorphism Scanning by High-Resolution Melting Analysis," Clinical Chemistry 50(10):1748-1754 (2004); Zhou et al., "Closed-Tube Genotyping with Unlabeled Oligonucleotide Probes and a Saturating DNA Dye," Clinical Chemistry 50(8):1328-1335 (2004); and Zhou et al., "High-resolution DNA melting curve analysis to establish HLA genotypic identity," Tissue Antigens 64:156-164 (2004). Melting/annealing curve analysis instrumentation is commercially available from a variety of manufacturers.

Figure 5:
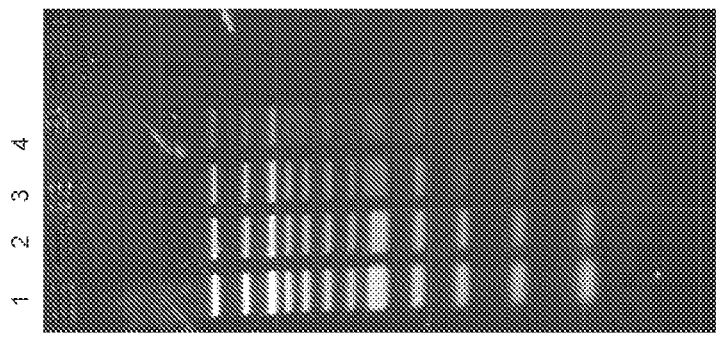
FIG. 5 shows that compound 6 can be used as a gel stain to detect dsDNA in agarose gels following gel electrophoresis. The lanes from left to right were loaded with 1 kb DNA ladder (Biotium) in amounts of 200, 100, 50 and 25 ng, respectively. See Example 3 for experimental details.

According to another embodiment, the nucleic acid detection is associated with detection of nucleic acid immobilized in a gel, such as an agarose gel or polyacrylamide gel (FIG. 5). In such a method, a nucleic acid sample is first separated by gel electrophoresis. The gel containing the separated sample can then be incubated in a staining solution comprising the nucleic acid detection agent of the invention for a time sufficient for effecting the staining (typically, 5-60 minutes). The gel can optionally be destained and then viewed or imaged using optical setting compatible with the spectral property of the nucleic acid dye. Alternatively, the dye may be pre-embedded in the gel matrix to form so-called precast gels, which can be used to electrophoretically separate nucleic acids and permit nucleic acid visualization either during or subsequent to electrophoresis without a separate staining step. Still alternatively, the dye may be added to the loading buffer so that nucleic acid can be detected either during or subsequent to gel electrophoresis.

In yet another embodiment of the invention, a method of quantitating the number of cells is provided (FIGS. 7A and 7B), the method comprising: (a) incubating a sample comprising cells or thought to comprise cells in a buffer comprising a compound of the invention for a time sufficient for the compound to bind to the nucleic acids of the cells; (b) detecting the fluorescence of the sample. Herein the principle of cell number quantitation is based on the fact that the amount of nucleic acids in cells is relatively similar among cells and thus the number of cells can be indirectly determined by measuring the amount of nucleic acids. In some embodiments, the cells may be live cells, either in a suspension or adhered to a surface, and the compound is generally one that can readily cross cell membranes. In some embodiments, the cells may be fixed and optionally permeabilized. The concentration is generally from about 0.5 µM to about 50 µM, more generally from about 5 µM to about 20 µM. In some cases, it is about 10 µM. The incubation time is generally from about 5 minutes to about 2 hours, more generally from about 15 minutes to about 1 hour. In some cases, fluorescence can be directly measured following the incubation without a wash step.

In one embodiment, the present invention provides a method of nucleic acid detection comprising the steps of (a) providing a mixture of at least two nucleic acid binding dyes that complement one another in at least one of the following aspects of dye performance: compatibility with various instruments, range of analyte detection, and compatibility with various detection formats; (b) in a reaction mixture, allowing said at least two complementary dyes to interact with nucleic acids contained within a sample under conditions such that the at least two complementary dye-nucleic acid complexes are formed; and (c) detecting an optical signal in said reaction mixture, said optical signal being indicative of the presence of said nucleic acid.

Current commercial nucleic acid detection reagents or kits typically use only a single nucleic acid dye species for the detection. Depending on the specific applications or detection formats, different dyes may have to be used for optimal compatibility. Although this is unavoidable in most cases, it is still desirable to have a single dye formulation that can accommodate more than one application or detection platform, or sometimes to broaden the detection range, thus providing convenience and/or save manufacturing cost. For example, qPCR master mixes and HRM master mixes are both used in nucleic acid amplification reactions, but their detection formats, which result in different requirements on the nucleic acid dyes used. For qPCR, fluorescence detection is carried out during the amplification process, whereas for HRM the detection is made only after the completion of the amplification process but during the melting of the dye-DNA complex. qPCR master mixes are designed to detect the amount of a target DNA sequence while HRM master mixes are primarily for detecting point mutation. Because the sensitivity of qPCR is typically measured by how early a fluorescent signal is produced (i.e., the Ct value) during the amplification process, a nucleic acid dye with high fluorescence quantum yield and relatively high DNA binding affinity is used in order to detect the smallest amount of DNA product possible during the early phase of PCR. Since the final fluorescence signal intensity has no effect in determining the Ct value, the dye concentration for qPCR is kept relatively low to ensure PCR efficiency. Opposite to qPCR, HRM typically employs a relatively high dye concentration in order to avoid so-called dye redistribution problem during the dye-DNA complex melting (U.S. Pat. Nos. 7,387,887; 7,456,281; and 7,582,429). This high dye concentration requirement precludes some of the common qPCR dyes (such as SYBR Green I) from being used in HRM application because the relatively high DNA binding affinity coupled with the high concentration of a qPCR dye can severely inhibit PCR, a necessary step proceeding HRM (Mao, Leung et al. 2007). For this reason, HRM typically employs relatively low affinity DNA binding dyes, which in general are not optimal for qPCR. Thus, qPCR master mixes and HRM master mixes are typically specifically formulated for each of their uses despite the fact that they are both subject to the same nucleic acid amplification process in their procedures. It is, therefore, highly desirable to have a single master mix useful for both qPCR and HRM.

The method of nucleic acid detection using a mixture of at least two complementary nucleic acid dyes according to the invention overcome the limited compatibility problems of qPCR master mixes and HRM master mixes described above and has other additional applications and advantages, compared to reagents using only a single dye species. Herein the term "mixture of complementary dyes" refers to a group of at least two nucleic acid binding dye species where each nucleic acid dye species offers complementary physicochemical property or properties to the others such that collectively the group of dyes has improved performance relative to any member of the dye group, Preferably, the mixture of complementary dyes comprises two dyes (i.e., two dye species). The aspects of improved performance include, but are not limited to, dynamic range of analyte detection, sensitivity, compatibility with various detection formats and compatibility with various instruments. In general, to be a complementary dye, at least one physicochemical property of the dye is substantially different from that of another member dye in the group such that the presence of the dye in the group or dye mixture contributes to detectable improvement in nucleic acid detection. The physicochemical properties may include DNA binding affinity, sequence selectivity, absorption wavelength and emission wavelength. As an example, a nucleic acid dye of relatively low binding affinity generally has a broad linear detection range and is responsive toward nucleic acid at high concentration but may show poor sensitivity to nucleic acid at very low concentration. On the other hand, a nucleic acid dye of relatively high binding affinity may be sensitive to nucleic acid at very low concentration but is unresponsive toward nucleic acid at high concentration due to saturation binding. Use of a nucleic acid reagent comprising both dyes in a suitable ratio may possess the benefits of both dyes without their disadvantages. In general, to maximize the advantages and minimize the disadvantages of the two dyes in the dye mixture, the ratio of the higher affinity dye to the lower affinity is ≤1/2, preferably ≤1/10, more preferably from about 1/100, 1/75, 1/50, 1/40, 1/30 to about 1/20. As another example, dyes of different sequence selectivity, such as a GC-selective dye and a AT-selective dye, may be mixed to form a nucleic acid detection reagent that responds to the amount of nucleic acid in a manner less dependent on nucleic acid sequence variation. AT-selective dyes include, but are not limited to, acridine homodimers such as bis-(6-chloro-2-methoxy-9-acridinyl)spermine, intercalators such as ACMA (9-amino-6-chloro-2-methoxyacridine), minor groove binders such as DAPI (4',6-diamidino-2-phenylindole), and Hoechst dyes (Hoechst 33342, 33258); and other dyes such as stilbamidine. GC-selective dyes include, but are not limited to, dyes such as chromomycin A3, or 7-aminoactinomycin D. In still another example, nucleic acid dyes of different wavelengths may be mixed for improved instrument compatibility. Traditional fluorescence-based instruments are equipped with various lasers as the excitation sources. However, many modern instruments employ the much less expensive and more reliable LEDs as the excitation sources. For example, the 488 nm argon laser, a widely used excitation source for many green fluorescent dyes, has been replaced with the 470 nm LED light. Most of the popular green fluorescent dyes, including the popular nucleic acid dyes (such as SYBR Green I, EvaGreen, PicoGreen, BRYT Green and SYTO9), have absorption maxima centered within the 490 nm to about 500 nm range, which makes the 488 nm excitation efficient but the 470 nm excitation relatively inefficient. Thus, to avoid large variation in the results of detection due to different instruments, it would be desirable to use a mixture of nucleic acid dyes comprising both a 477 nm-excitable dye and a 488 nm-excitable dye with both dyes emitting in the green optical channel.

In one embodiment, the invention provides a method of nucleic acid amplification comprising the steps of: (a) conducting a nucleic acid amplification reaction in the presence of a mixture of at least two complementary nucleic acid binding dyes (species), which reaction results in an increase in optical signal that is indicative of the presence of amplified nucleic acids; (b) detecting said optical signal as the amplification reaction proceeds. In one aspect, the increase in optical signal is proportional to increase in the amount of amplified nucleic acids resulted from said amplification. In a preferred embodiment, the mixture of dyes is a mixture of two dyes, wherein one of the dyes is a nucleic acid dye suitable for qPCR and the other dye is a nucleic acid dye suitable for HRM. Preferably, the concentration ratio of [qPCR dye]/[HRM dye] is ≤1/2, preferably ≤1/10, more preferably from about 1/100 to about 1/20. Suitable qPCR dyes include, but are not limited to, EvaGreen, SYBR Green I, BRYT Green and dyes from the invention. In a preferred embodiment, qPCR dyes are Dyes 5-13 of Table 1. Suitable HRM dyes include, but are not limited to, EvaGreen, LCGreen, LCGreen Plus, ResoLight and dyes from the present invention.

In one embodiment, the invention provides a PCR analysis method comprising the steps of: (a) amplifying a first target nucleic acid in the presence of a mixture of at least two complementary nucleic acid binding dyes (i.e., dye species); (b) monitoring the fluorescence of the DNA-dye complexes as the complexes are being melted, thereby generating a standard DNA melt curve; (c) repeating the amplifying in step (a) and monitoring in step (c) with at least one additional target nucleic acid, thus generating at least one additional DNA melt curve; and (d) comparing each additional melt curve with the standard melt curve and plotting each additional melt curve as a difference from the standard melt curve across the curves. Preferably, the mixture of dyes is a mixture of two dyes, wherein one of the dyes is a nucleic acid dye suitable for qPCR and the other dye is a nucleic acid dye suitable for HRM. Preferably, the concentration ratio of [qPCR dye]/[HRM dye] is ≤1/2, preferably ≤1/10, more preferably from about 1/100 to about 1/20. Suitable qPCR dyes include, but are not limited to, EvaGreen, SYBR Green I, BRYT Green and dyes from the invention. In a preferred embodiment, qPCR dyes are Dyes 5-13 of Table 1. Suitable HRM dyes include, but are not limited to, EvaGreen, LCGreen, LCGreen Plus, ResoLight and dyes from the present invention.

Figure 13:
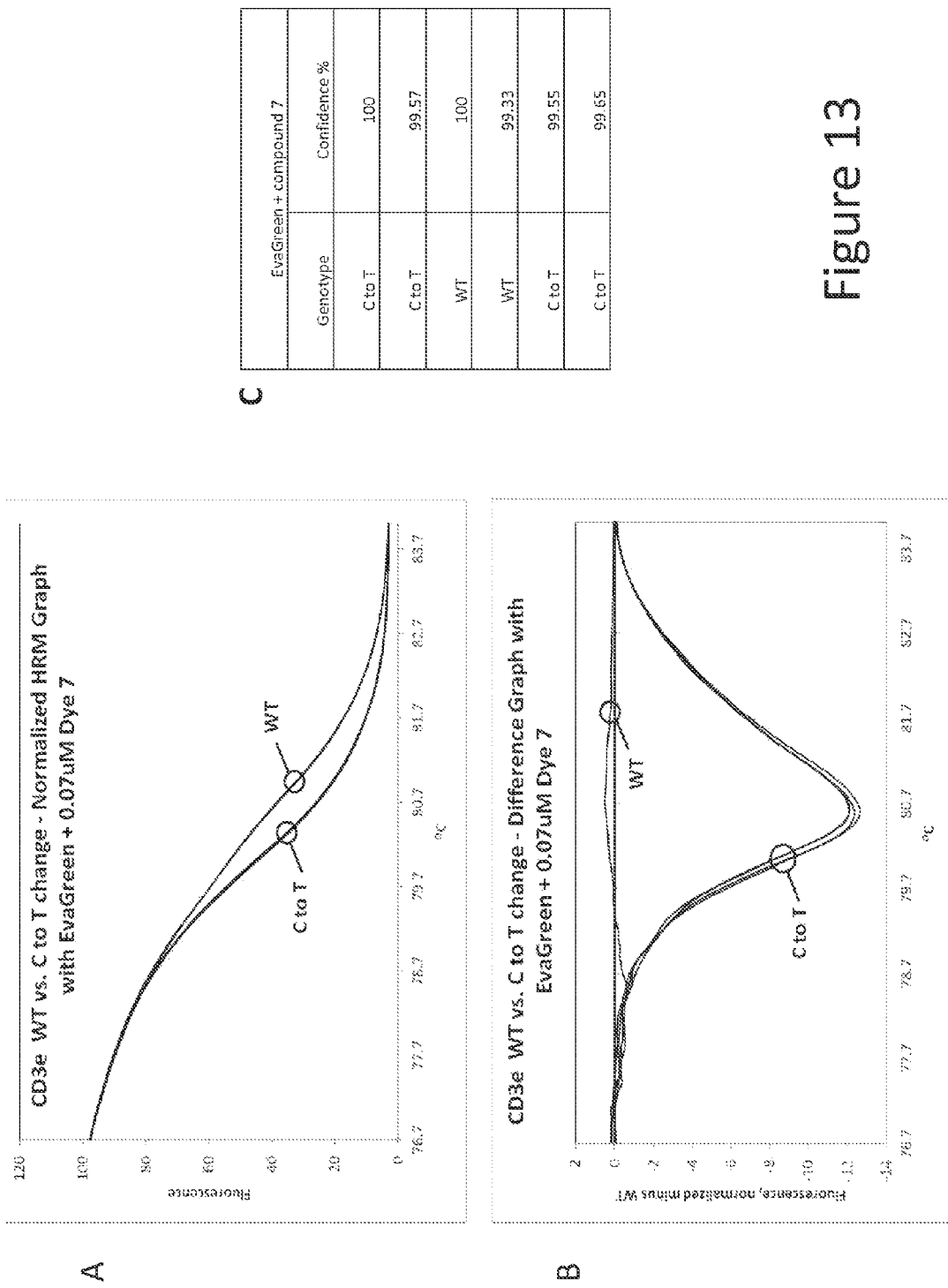
FIG. 13 show normalized graphs (13A) and difference graphs (13B) from the HRM analysis of PCR products generated from template plasmids containing either a WT copy of CD3e or a version with a single base pair change with EvaGreen dye and 0.07 µM compound 7. The genotype calls of the HRM software are also shown (13C).
Figure 14:
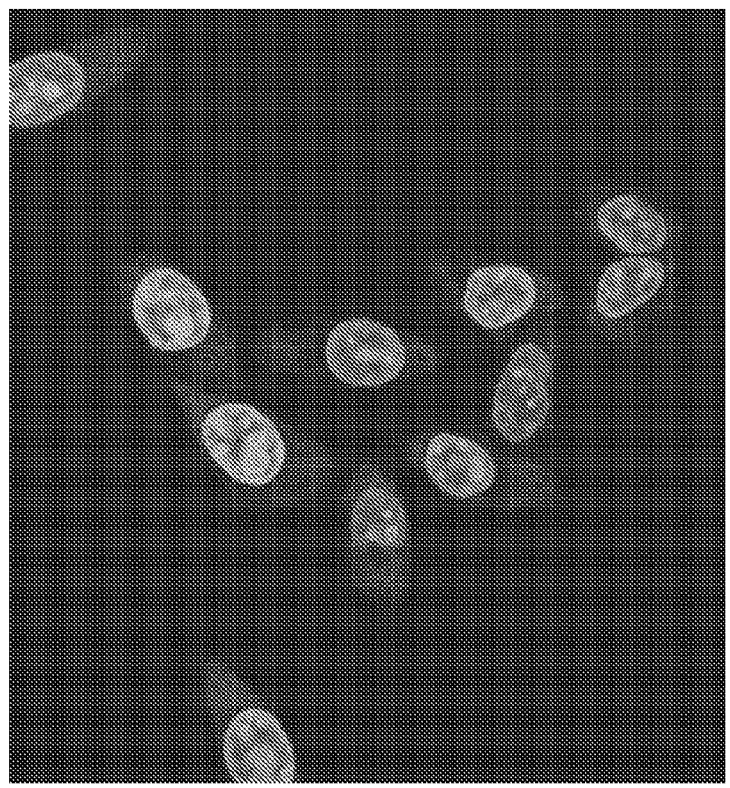
FIG. 14 shows the staining of fixed cells with compound 36.

FIGS. 13 and 14 demonstrate the benefits of using a mixture of two complementary nucleic acid binding dyes for qPCR and HRM. FIG. 13 shows that adding a very small amount of Dye 7 (a qPCR dye) to a EvaGreen dye-based HRM master mix improved the Ct value in qPCR application. FIG. 14 shows that the same master mix are also suitable for HRM application, with even better confidence calling than the HRM master mix comprising only EvaGreen dye.

The target nucleic acid that can be analyzed by one or more of the subject methods encompasses any reaction samples suspected to contain the target sequence. It is not intended to be limited as regards to the source of the reaction sample or the manner in which it is made. Generally, the test sample can be biological and/or environmental samples. Biological samples may be derived from human, other animals, or plants, body fluid, solid tissue samples, tissue cultures or cells derived therefrom and the progeny thereof, sections or smears prepared from any of these sources, or any other samples suspected to contain the target nucleic acids. Preferred biological samples are body fluids including but not limited to blood, urine, spinal fluid, cerebrospinal fluid, sinovial fluid, ammoniac fluid, semen, and saliva. Other types of biological sample may include food products and ingredients such as vegetables, dairy items, meat, meat by-products, and waste. Environmental samples are derived from environmental material including but not limited to soil, water, sewage, cosmetic, agricultural and industrial samples.

Systems

The invention provides for systems that can be used to detect target analytes, such as nucleic acids. The system can include at least one detector (e.g., a spectrometer, etc.) that detects a signal that is indicative of a target analyte. For example, the system can include a detector for measuring an optical signal, such as fluorescence. In addition, the system can include at least one thermal modulator (e.g., a thermal cycling device, etc.) operably connected to a container or solid support to modulate temperature of a sample. The thermal modulator can be used for performing nucleic acid amplification methods, melting curve analysis, and/or hybridization assays.

Detectors can be structured to detect detectable signals produced, e.g., in or proximal to another component of the given assay system (e.g., in container, on a solid support, etc.). Suitable signal detectors that are optionally utilized, or adapted for use, herein detect, e.g., fluorescence, phosphorescence, radioactivity, absorbance, refractive index, luminescence, mass, or the like. Detectors optionally monitor one or a plurality of signals from upstream and/or downstream of the performance of, e.g., a given assay step. For example, detectors optionally monitor a plurality of optical signals, which correspond to real-time events. Example detectors or sensors include photomultiplier tubes, CCD arrays, optical sensors, temperature sensors, pressure sensors, pH sensors, conductivity sensors, scanning detectors, or the like. More specific exemplary detectors that are optionally utilized in performing the methods of the invention include, e.g., resonance light scattering detectors, emission spectroscopes, fluorescence spectroscopes, phosphorescence spectroscopes, luminescence spectroscopes, spectrophotometers, photometers, and the like. Detectors are also described in, e.g., Skoog et al., *Principles of Instrumental Analysis*, 5$^{th}$ Ed., Harcourt Brace College Publishers (1998) and Currell, *Analytical Instrumentation: Performance Characteristics and Quality*, John Wiley & Sons, Inc. (2000), both of which are incorporated by reference.

The systems of the invention can include controllers that are operably connected to one or more components (e.g., detectors, thermal modulators, fluid transfer components, etc.) of the system to control operation of the components.

More specifically, controllers can be included either as separate or integral system components that are utilized, e.g., to receive data from detectors, to effect and/or regulate temperature in the containers, to effect and/or regulate fluid flow to or from selected containers, or the like. Controllers and/or other system components is/are optionally coupled to an appropriately programmed processor, computer, digital device, or other information appliance (e.g., including an analog to digital or digital to analog converter as needed), which can function to instruct the operation of these instruments in accordance with preprogrammed or user input instructions, receive data and information from these instruments, and interpret, manipulate and report this information to the user. Controllers are available from various commercial sources.

Any controller or computer optionally includes a monitor, which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user.

The computer can include appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

In some embodiments, the invention provides integrated systems for performing quantitative PCR and for making $T_m$ determinations. The systems can include instrumentation and tools for interpreting and analyzing collected data, especially including tools for determining quantity of amplified nucleic acids and for deriving $T_m$. These tools can include algorithms and/or the ability to electronically store information (e.g., collected fluorescence data, predetermined $T_m$ correlations, etc). Each part of an integrated system can be functionally interconnected, and in some cases, physically connected. In some embodiments, the integrated system is automated, where there is no requirement for any manipulation of the sample or instrumentation by an operator following initiation of the qPCR or $T_m$ analysis.

A system of the invention can include instrumentation. For example, the invention can include a detector such as a fluorescence detector (e.g., a fluorescence spectrophotometer). A detector or detectors can be used in conjunction with the invention, e.g., to monitor/measure the emission from a tight emitting moiety, such as a nucleic acid dye. A detector can be in the form of a multiwell plate reader to facilitate the high-throughput capacity of the assays described herein.

In some embodiments, the integrated system includes a thermal cycling device, or thermocycler, for the purpose of controlling the temperature of the $T_m$ melting analysis or for modulating the temperature for performing nucleic acid amplification. In some embodiments, the thermal cycling device and the detector are an integrated instrument, where the thermal cycling and emission detection (e.g., fluorescence detection) are performed in the same device.

A detector, e.g., a fluorescence spectrophotometer, can be connected to a computer for controlling the spectrophotometer operational parameters (e.g., wavelength of the excitation and/or wavelength of the detected emission) and/or for storage of data collected from the detector (e.g., fluorescence measurements during a melting curve analysis). The computer may also be operably connected to the thermal cycling device to control the temperature, timing, and/or rate of temperature change in the system. The integrated computer can also contain the "correlation module" where the data collected from the detector is analyzed and where the $T_m$ of the target hybridization complex and/or the concentration of amplified or target nucleic acid is determined. In some embodiments, the correlation module comprises a computer program that calculates the $T_m$ or the concentration of nucleic acid based on the fluorescence readings from the detector, and in some cases, optionally derives sequence and/or genotype information of an unknown sample based on the $T_m$ and/or qPCR result. In some embodiments, the correlation module compares the $T_m$ of the unknown sample with a database (or table) of $T_m$ values for known sequences and/or genotypes to make a correlation between the $T_m$ of the unknown sample and the sequence or genotype of the unknown sample.

In some aspects, a system of the invention for the determination of a $T_m$ of a hybridization complex and/or for performing qPCR comprises a reagent composition, a thermal control device for regulating the temperature reaction over a range of temperatures, and a detector for measuring the signal from the melting reaction over the range of temperatures. In some cases, the system also includes a correlation module that is operably coupled to the detector and receives signal measurements, where the correlation module correlates the signal intensity with the concentration of the target analyte or the melting temperature of the target analyte.

Kits

The present invention provides a kit for detecting and/or quantifying nucleic acid or cell number in a sample, the kit comprising a compound as described herein and an instruction manual. In some embodiments the kit can also comprise any of the following: a buffer, a set of nucleic acid standards with known concentrations for generating a standard curve, a test sample, a detergent for facilitating the dye reagent's entrance into cells. Two or more of the kit components may be packaged within the same container.

The present invention also provides for amplification reagent mixture comprising a compound of the present invention, which may be a single compound of the invention or a mixture with a complementary dye; dNTPs; polymerase; PCR buffer and a technical manual. The PCR buffer may optionally comprise one or more enzyme stabilizers, one or more agents for optimizing the PCR performance and a reference dye, such as ROX, for instrument calibration.

Any DNA and/or RNA polymerases can be included in the amplification reagent mixture. The polymerases can be natural or recombinant such as Taq polymerase, Pfu polymerase, T7 DNA polymerase, Klenow fragment of *E. coli* DNA polymerase, Tma DNA polymerase, exo-Tli DNA polymerase, exo-KOD DNA polymerase, exo-JDF-3 DNA polymerase, exo-PGB-D DNA polymerase, U1Tma (N-truncated) *Thermatoga martima* DNA polymerase, Sequenase, and/or RNA polymerases such as reverse transcriptase.

Polymerases capable of strand-displacement can also be included in a nucleic acid amplification reaction.

The examples below are for the purpose of illustrating the practice of the invention. They shall not be construed as being a limitation on the scope of the invention or claims.

EXAMPLES

Example 1: Measurement of Absorption and Emission Spectra of Nucleic Acid Binding Dyes All absorption spectra were measured on a Beckman Coulter DU-800 spectrophotometer at room temperature. All fluorescence spectra were measured on a Hitachi F-4500 fluorescence spectrophotometer at room temperature. To record the complete emission profiles, excitation wavelengths were set 30 nm shorter than the absorption maxima of the dyes. The dsDNA used was calf thymus dsDNA from Sigma. When dsDNA was present in the dye solutions, spectra were recorded after the dyes had been incubated with the DNA for at least 10 minutes.

Figure 3:
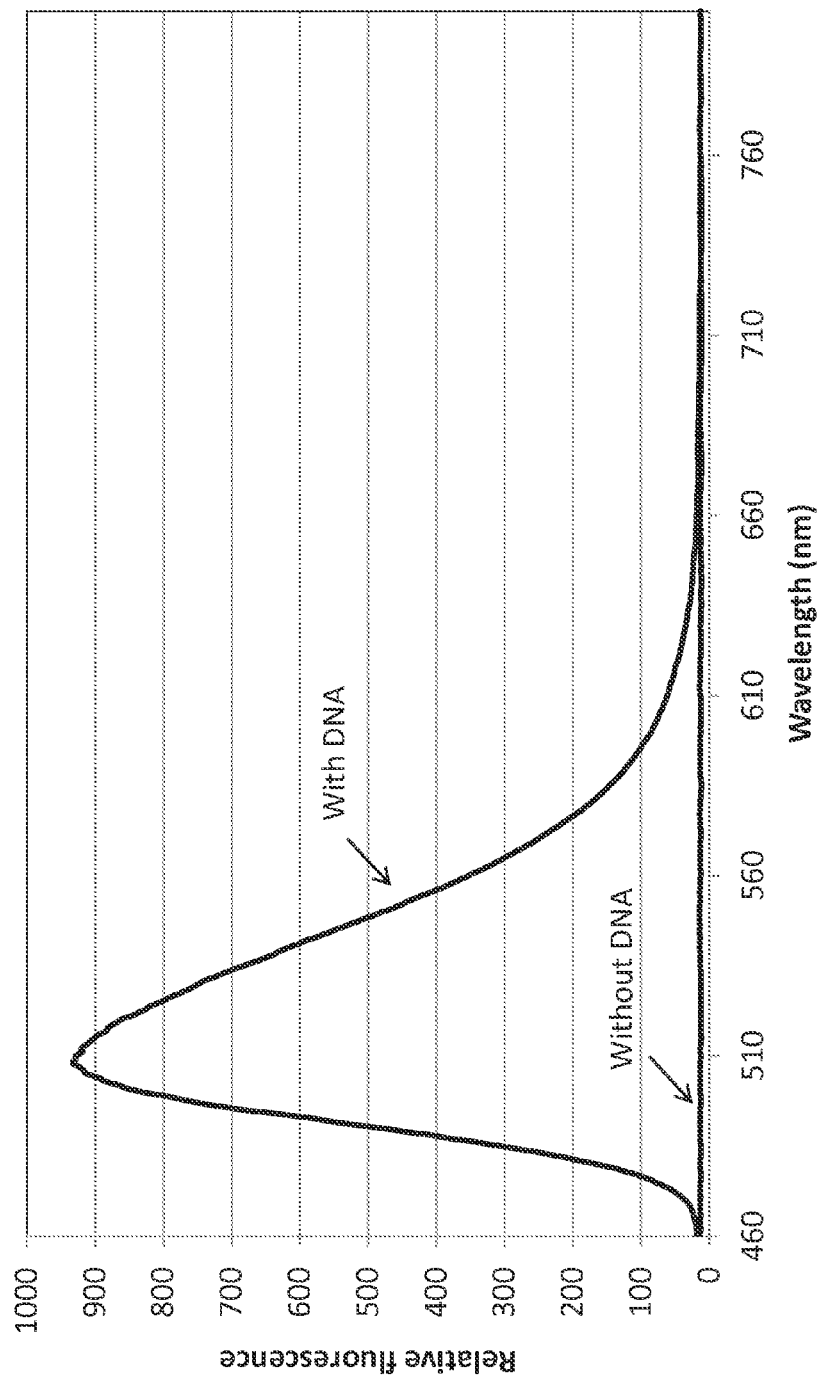
FIG. 3 shows the fluorescence spectra of compound 5 (1 mM) with and without the presence of DNA (30 mg/mL) in 10 mM pH 7.4 Tris. See Example 1 for experimental details.

The absorption and emission maxima of compound 5 are at ~470 nm and ~520 nm, respectively, making the compound optimally compatible with 470 nm LED-based fluorescence instruments. The spectra of compound 32 show that relatively long wavelength fluorescent dyes may be prepared by having a substituted vinyl group (V) according to the invention. FIG. 3 shows that compound 5 is essentially nonfluorescent in the absence of DNA but becomes highly fluorescent upon DNA binding.

Example 2: DNA Quantitation compounds 5, 7 and related compounds according to the invention can be used to quantitate double-stranded DNA in solution with high sensitivity and accuracy over a wide range of DNA concentrations, as shown in FIGS. 4 and 5. FIG. 4 shows the linearity of fluorescence for compound 7 and PicoGreen at 0.5 µM dye concentration for DNA amounts ranging from 0.015-2 ng. The linearity for PicoGreen is lower than that of compound 7 at lower DNA concentrations (FIG. 4 inset). Moreover, by having a higher slope for the titration curve, compound 7 is more sensitive than PicoGreen. At 1 mM dye concentration, compound 5 fluorescence is linear from 0.04-250 ng (FIG. 5).

The data shown in FIG. 4A was obtained under the following conditions: compound 7 at 0.5 µM was prepared in TE buffer (10 mM Tris, 1 mM EDTA, pH 7.5), and pipetted into wells of black 96-well plates at 200 µL per well. Two-fold dilutions of calf thymus DNA were prepared in TE buffer starting at 0.2 ng/uL, and 10 µL of each DNA dilution was added per 96 well to obtain a standard curve of 2 ng to 0.015 ng per well. The plates were incubated for five minutes at room temperature, protected from light, then read at 468 nm excitation and 507 nm emission using a Molecular Devices Gemini XS fluorescent plate reader. Triplicate samples were averaged and background fluorescence (no DNA) was subtracted. Fluorescence values were plotted against the DNA amount (ng/well). The inset graph shows the lower range of the DNA titration. The $R^2$ values for linear regression are shown next to each curve. The data shown in FIG. 4B were obtained under similar condition except that compound 5 at 1 uM was used and serial DNA dilutions were from 250 ng to 0.04 ng.

Example 3: Nucleic Acid Gel Staining

The data in FIG. 3 were obtained under the following conditions: 1% agarose/TBE gels were prepared following standard molecular biology protocols. 1 kb DNA ladder (Biotium) was separated by electrophoresis in 1×TBE buffer, and gel was stained in 1 uM compound 6. The total amount of samples loaded in the lanes from 1 to 4 are: 200, 100, 50 and 25 ng, respectively. The gel was imaged using a UVP GelDoc-It system equipped with the FirstLight UV transilluminator and green emission filter using VisionWorks LS software.

Example 4: Staining Live and Fixed Cells with Dyes 5, 7 and 8

The images in the top panel of FIG. 6 were obtained under the following conditions: live HeLa cells were incubated with 10 uM compound 7, compound 8, or Dye 5 for 30 minutes at 37 C in a $CO_2$ incubator. The images in the bottom panel of FIG. 6 were obtained under the following conditions: HeLa cells were formaldehyde-fixed, permeabilized, and blocked according to standard immunofluorescence staining protocols. Cell were stained with 10 µM compound 7, 8 or 5 in PBS/5% BSA for 30 minutes, then washed with PBS buffer and imaged. Live and fixed cells were imaged using an Olympus epifluorescence microscope equipped with a FITC filter set, Retiga 2000R Fast 1394 camera (QImaging), and Image-Pro Express software (Media Cybernetics).

Example 5: Cell Number Quantitation

Figure 7A:
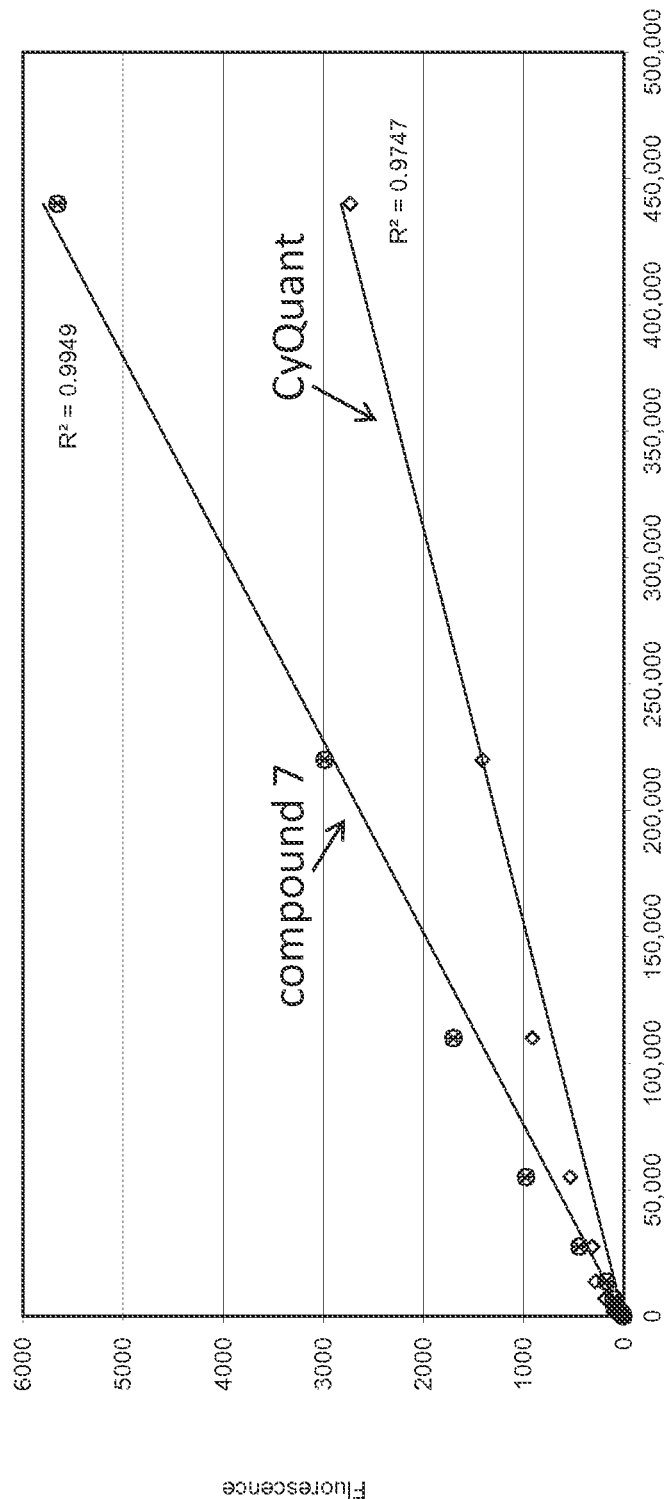
FIGS. 7A and 7B show that fluorescence staining of cell nuclei in cultured cells using compound 5 and compound 7 can be used to quantitate cell numbers in cell suspensions (FIG. 7A), or in adherent cell cultures (FIG. 7B). See Example 5 for experimental details.
Figure 7B:
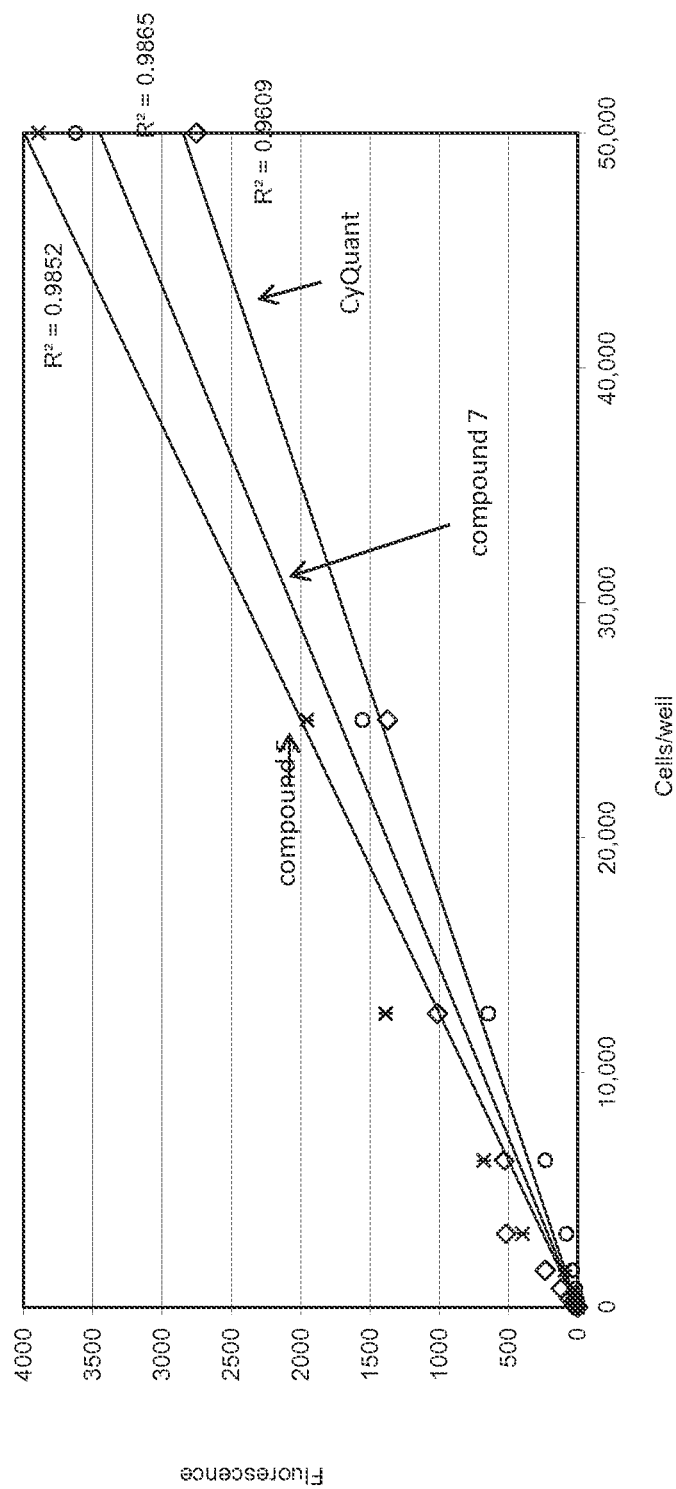

Fluorescence staining of cell nuclei in cultured cells using compounds 5 and 7 can be used to quantitate cell numbers in cell suspensions, as shown in FIG. 7A, or in adherent cell cultures, as shown in FIG. 7B.

The data in FIG. 7A were obtained under the following conditions: compound 5 or 7 at 20 uM in Hank's Balanced Salt Solution (HBSS) was pipetted into optical bottom black 96 well tissue culture plates at 50 µL per well. Two-fold serial dilutions of Jurkat cells in suspension culture were prepared in Hank's Balanced Salt Solution (HBSS) and pipetted into black 96 well plates at 50 µL per well to obtain a dilution curve of 440,000 to 860 cells per well, and a final dye concentration of 10 uM. Plates were incubated for 30 minutes at 37° C. in a 5% $CO_2$ incubator, and fluorescence was read at 468/507 nm in a Molecular Devices Gemini XS fluorescent plate reader. Triplicate samples were averaged and background fluorescence (no cells) was subtracted. Fluorescence values were plotted against the DNA amount (ng/well). The $R^2$ values for linear regression are shown next to each curve. For comparison, cell numbers were quantitated using the CyQUANT NF Cell Proliferation Assay Kit (Life Technologies) according to the kit manual.

The data in FIG. 7B was obtained under the following conditions: adherent HeLa cells were seeded at densities ranging between 50,000 and 100 cells per well in optical bottom black 96 well tissue culture plates and allowed to adhere overnight at 37° C. in a 5% $CO_2$ incubator. On the day after seeding, the cells were washed with HBSS and incubated in HBSS containing Dye 5 or Dye 7 at 10 uM for 30 minutes at 37° C. Fluorescence was read at 468/507 nm in a Molecular Devices Gemini XS fluorescent plate reader. Triplicate samples were averaged and background fluorescence (no cells) was subtracted. Fluorescence values were plotted against the DNA amount (ng/well). The $R^2$ values for linear regression are shown next to each curve. For comparison, cell numbers were quantitated using the CyQUANT NF Cell Proliferation Assay Kit (Life Technologies according to the kit manual.

Example 6: Real-Time PCR with Plasmid DNA

Compound 7 and related dyes can be used in real time PCR experiments to monitor amplification of target plasmid DNA. In FIG. 8, $5\times10^5$ copies of linearized GAPDH-containing plasmid DNA or water (non-template controls, NTC) were added to PCR reaction mixes containing 0.34 uM of either SYBR Green I (lines with solid diamonds (DNA) or "x's" (water)) or Compound 7 (lines with triangles (DNA) or circles (water)) and real time PCR was performed. Compound 7 allowed for efficient amplification of target amplicon, a region of GAPDH from plasmid DNA, with an early Ct value and high endpoint fluorescent signal.

The data in FIG. 8 were collected under the following conditions: PCR reactions consisted of a final concentration of 50 mM Tris-HCl (pH 8.6), 3 mM $MgCl_2$, 50 µg/ml non-acetylated BSA (Sigma), 200 µM dNTPs (New England BioLabs), 500 nM GAPDH Forward primer (5'-GAAGGT-GAAGGTCGGAGTC-3'), 500 nM GAPDH Reverse primer (5'-GAAGATGGTGATGGGATTTC-3') (Integrated DNA Technologies), 1 U Hot-Start Cheetah Taq (Biotium, Inc.) and either 0.34 uM SYBR Green I (Life Technologies) or 0.34 uM compound 7. One microliter of $5\times10^5$ copies linearized pCMV-SPORT6 GAPDH plasmid (Open Biosystems) was added to each 20 ul reaction. Real time PCR was performed using the RotorGeneQ with the following cycling conditions: 95° C. for 2 minutes, followed by 45 cycles of 95° C. for 5 seconds and 60° C. for 30 seconds, with data acquisition during the elongation stage on the green channel.

Example 7: Real-Time PCR with cDNA

Compound 7 and related dyes can be used in real time PCR experiments to monitor amplification of target cDNA. In FIG. 9, serial dilutions of total cDNA generated from Jurkat cell purified mRNA were added to PCR reaction mixes containing 0.34 uM compound 7 and real time PCR was performed. Compound 7 allowed for efficient amplification of the target amplicon, a region from GAPDH cDNA, from each of the serial dilutions.

The data in FIG. 9 were collected under the following conditions: mRNA was purified from $4\times10^6$ Jurkat cells using Qiagen's RNeasy Kit and cDNA was then generated using oligo-dT primers and the ProtoScript First Strand cDNA Synthesis Kit (New England BioLabs). Serial 1:2 dilutions of the cDNA in water were prepared and added to PCR reactions consisting of a final concentration of 25 mM Tris-HCl (pH 8.6), 5 mM KCl, 10 mM $(NH_4)_2SO_4$, 2 mM $MgCl_2$, 2.5% glycerol, 5% DMSO, 200 uM dNTPs (New England BioLabs), 0.01% Tween-20, non-acetylated BSA (Sigma), 500 nM GAPDH Forward primer (5'-GAAGGT-GAAGGTCGGAGTC-3'), 500 nM GAPDH Reverse primer (5'-GAAGATGGTGATGGGATTTC-3') (Integrated DNA Technologies), 1 U Taq polymerase (Syzygy) modified using a HotStart Polymerase Modification Kit (Biotium, Inc.) and 0.34 uM compound 7. One microliter cDNA was added to each 20 ul reaction. Real time PCR was performed using the RotorGeneQ as described for FIG. 8.

Example 8: Post-PCR DNA Melt Curve Analysis

Compound 7 and related dyes were used to perform post-real time PCR melt curve analysis. In FIG. 9, a fragment of GAPDH from plasmid DNA that was amplified using real time PCR (as described in FIG. 8) was subjected to melt curve analysis. The plot of the negative derivative of fluorescence relative to temperature is shown and melt peaks are seen at approximately 88° C. for reactions that contained template and SYBR Green I (line with squares) or compound 7 (line with diamonds). No melt peaks were observed for non-template control reactions (straight line or line with "x's").

The data in FIG. 9 were collected under the following conditions: Real time PCR was performed as described for FIG. 8 on the RotorGeneQ and subsequent melt curve analysis was performed in increments of 0.3° C. from 57° C. to 99° C. with a 5 second hold on each step. Data was acquired on the green channel.

Example 9: Use of Nucleic Acid Dyes in Combination to Improve the Performance of a qPCR or HRM Master Mix Use of two or more nucleic acid binding dyes that are complementary to one another in one or more aspects of physicochemical properties can improve the performance of a master mix for real-time PCR and/or melt curve analysis, including high-resolution melt curve analysis (HRM).

A. Real-Time PCR Improvement

Figure 11:
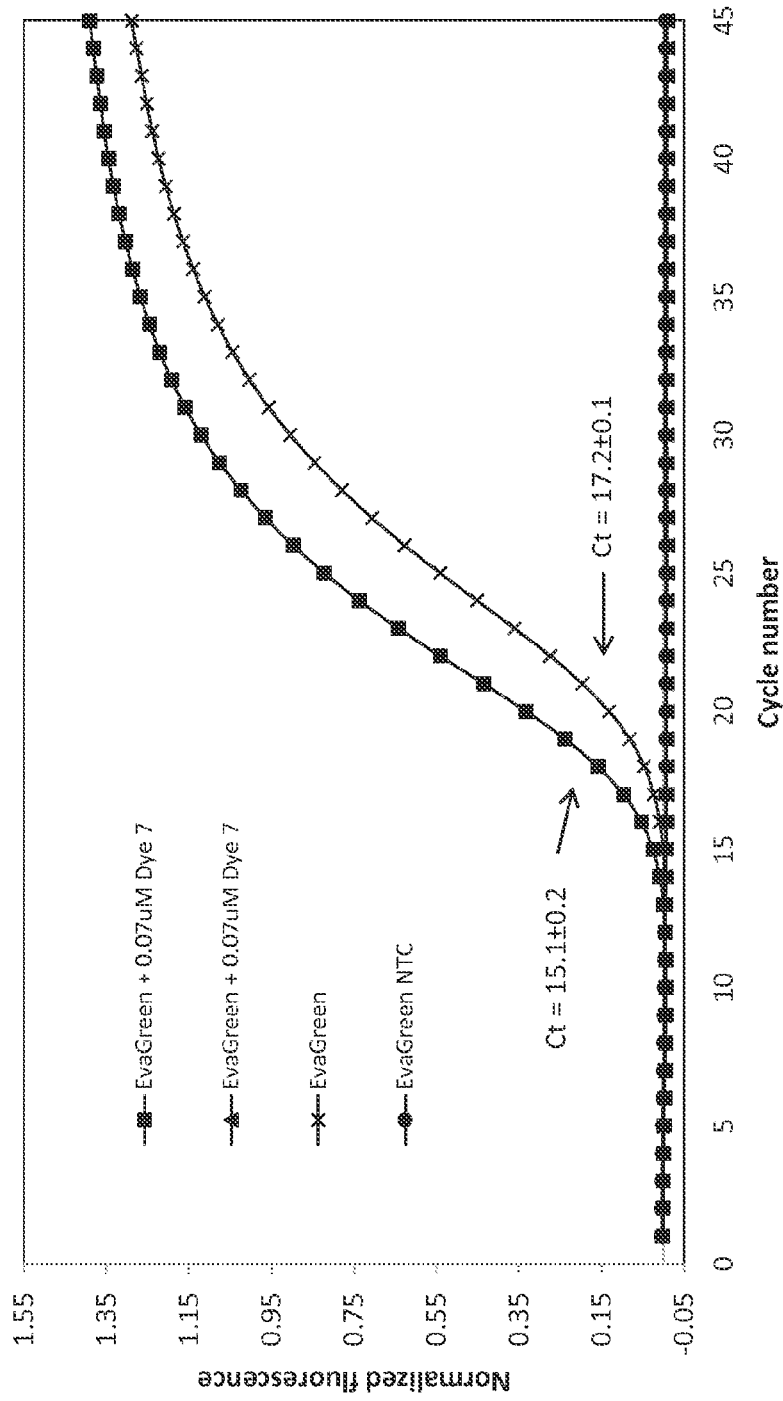
FIG. 11 shows that compound 7 and EvaGreen dye can be used in combination in a master mix to render the master mix optimal for qPCR applications. See Example 9 for experimental details.

The addition of a small amount of compound 7 to existing real time PCR Master Mixes was used to boost the intensity of fluorescent signal resulting in observation of lower threshold values in real time PCR experiments. In FIG. 11, $1\times10^6$ copies of linearized GAPDH-containing plasmid DNA or water (non-template controls, NTC) were added to PCR reaction mixes containing EvaGreen dye at 1.25 uM (lines with "x's" (DNA) or circles (water)) or EvaGreen dye with 0.07 uM Dye 7 (lines with squares (DNA) or triangles (water)) and real time PCR was performed. The addition of compound 7 to a real time PCR Master Mix containing another primary DNA binding dye allowed for efficient amplification of the target amplicon, a region of GAPDH from plasmid DNA, with an early Ct value and high endpoint fluorescent signal (FIG. 11). Duplicate experiments yielded average Ct values of 17.5±0.1 and 15.1±0.2 for the amplifications using EvaGreen dye alone and combination of EvaGreen dye and compound 7, respectively.

The data in FIG. 11 were collected under the following conditions: PCR reactions consisted of a final concentration of 25 mM Tris-HCl (pH 8.6), 10 mM $(NH_4)_2SO_4$, 2 mM $MgCl_2$, 1.25% glycerol, 5% DMSO, 1× EvaGreen dye (Biotium, Inc.), 0.015% Tween-20, 11 ug/ml non-acetylated BSA (Sigma), 200 uM dNTPs (New England BioLabs), 500 nM GAPDH Forward primer (5'-GAAGGTGAAGGTCG-GAGTC-3'), 500 nM GAPDH Reverse primer (5'-GAAGATGGTGATGGGATTTC-3') (Integrated DNA Technologies), 1 U Hot-Start Cheetah Taq (Biotium, Inc.) and 0.07 uM compound 7. One microliter of $1\times10^6$ copies linearized pCMV-SPORT6 GAPDH plasmid (Open Biosystems) was added to each 20 ul reaction. Real time PCR was performed using the RotorGeneQ with the following cycling conditions: 95° C. for 2 minutes, followed by 45 cycles of 95° C. for 5 seconds and 60° C. for 30 seconds, with data acquisition during the elongation stage on the green channel.

B. Improvement of High-Resolution Melt Curve Analysis (HRM)

Figure 12:
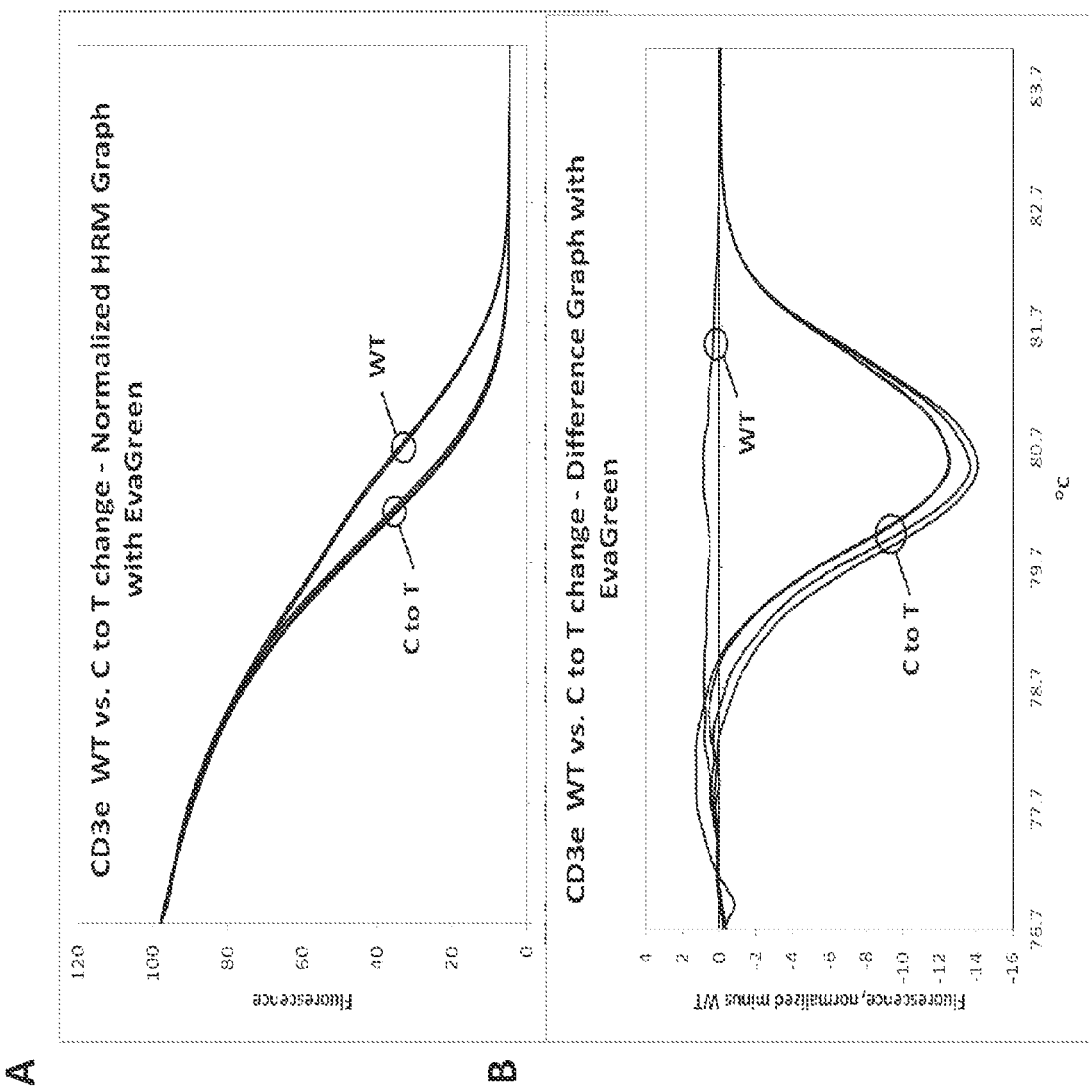
FIG. 12 show normalized graphs (12A) and difference graphs (12B) from the HRM analysis of PCR products generated from template plasmids containing either a WT copy of CD3e or a version with a single base pair change with EvaGreen dye. The genotype calls of the HRM software are also shown (12C).

"Spiking" EvaGreen Master Mix with compound 7 improves HRM analysis resolution. The addition of a small amount of compound 7 to existing real time HRM Master Mixes can improve the resolution of the melting curves leading to higher confidence calls by HRM software. FIGS. 12 and 13 show normalized graphs (12A, 13A) and difference graphs (12B, 13B) from the HRM analysis of PCR products generated from template plasmids containing either a WT copy of CD3e or a version with a single base pair change. The genotype calls of the HRM software are also shown (12C, 13C).

The data in FIGS. 12 and 13 were collected under the following conditions: PCR reactions were performed as in FIG. 10 with 500 nM CD3e Forward primer (5'-GAGA-TACCACCATGCAGTCG-3') and 500 uM CD3e Reverse primer (5'-GGGCATGTCAATATTACTGTGG-3'). To each reaction, one microliter of approximately 1×10$^6$ copies/µl pME-human CD3e-6× His-HA was added, either with a wild type (WT) sequence or with a single nucleotide change (C to T) at base 54 from the start codon of the CD3e sequence. HRM analysis was performed on the RotorGeneQ immediately following template amplification from a temperature range of 76.5-86.5° C. ramping 0.1° C. every two seconds after initial 90 second pre-melt conditioning.

Example 10: Preparation of Compound 50a and Compound 50b

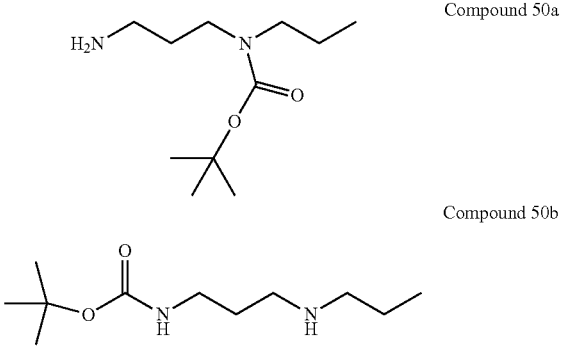

Compound 50a

Compound 50b

To a solution of N-propyl-1,3-propanediamine (2 g, 17.2 mmol) in DMSO (60 mL) at 0° C. was added dropwise a solution of di-tert-butyl dicarbonate (3.74 g, 17.2 mmol) in DMSO (60 mL). After the addition was completed, the mixture was allowed to warm up to room temperature slowly and then kept stirring at room temperature for 4 hrs. The solution was concentrated in vacuo and the residue was partitioned between EtOAc (100 mL) and phosphate buffer pH-5 (100 mL). The aqueous buffer was extracted with EtOAc (100 mL) and then neutralized to pH=7 with 1N NaOH. The aqueous solution was extracted with EtOAc (4×100 mL). The combined EtOAc layers was dried with anhydrous Na$_2$SO$_4$. The solvent was removed in vacuo and the residue was purified by column chromatography on silica gel to give Compound 50a (0.45 g) and Compound 50b (0.6 g) as colorless oil.

Example 11: Preparation of Compound 51

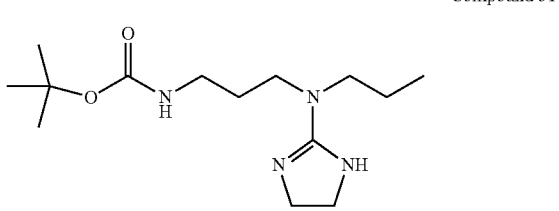

Compound 51

A mixture of Compound 50b (0.1 g, 0.46 mmol), 2-methylthio-2-imidazoline hydriodide (0.14 g, 0.56 mmol) and N,N-diisopropylethylamine (0.3 mL, 1.7 mmol) in EtOH (5 mL) was heated at 50° C. for 4 hrs. The mixture was concentrated to dryness in vacuo and the residue was purified by column chromatography on silica gel to give Compound 51 as white solid (90 mg).

Example 12: Preparation of Compound 52

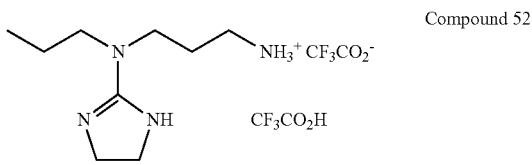

Compound 52

To a solution of Compound 51 (50 mg, 0.18 mmol) in CH$_2$Cl$_2$ (5 mL) at 0° C. was added TEA (1 mL). The mixture was stirred at 0° C. for 1 hr and then concentrated to dryness in vacuo. Et$_2$O (5 mL) was added to the residue and the suspension was stirred at room temperature overnight. The white precipitate (48 mg) was collected by centrifugation.

Example 13: Preparation of Compound 53

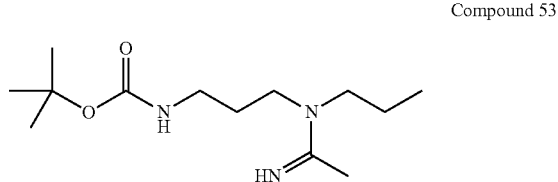 [SMILES: CCCN(CCCNC(=O)OC(C)(C)C)C(C)=N]

Compound 53

A mixture of Compound 50a (0.1 g, 0.46 mmol), ethyl acetimidate hydrochloride (68 mg, 0.56 mmol) and N,N-diisopropylethylamine (0.3 mL, 1.7 mmol) in EtOH (5 mL) was heated at 90° C. overnight. The mixture was concentrated to dryness in vacuo and the residue was purified by column chromatography on silica get to give Compound 53 as white solid (75 mg).

Example 14: Preparation of Compound 54

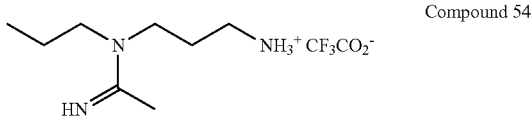

Compound 54

Compound 54 (72 mg) was prepared from Compound 53 (70 mg, 0.27 mmol) according to the procedure Example 12.

Example 15: Preparation of Compound 55

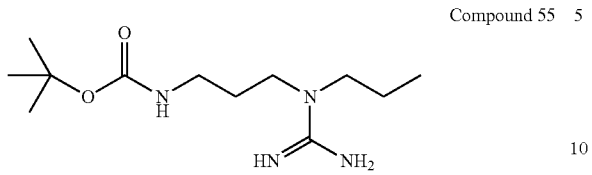
Compound 55

A mixture of Compound 50b (0.1 g, 0.46 mmol), S-methylisothiourea hemisulfate salt (80 mg, 0.56 mmol) and N,N-diisopropylethylamine (0.3 mL, 1.7 mmol) EtOH (5 mL) was heated at 50° C. overnight. The mixture was concentrated to dryness in vacuo and the residue was purified by column chromatography on silica get to give Compound 55 as white solid (85 mg).

Example 16: Preparation of Compound 56

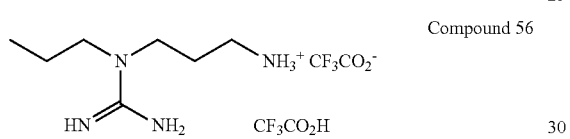
Compound 56

Compound 56 (75 mg) was prepared from Compound 55 (80 mg, 0.31 mmol) according to the procedure of Example 12.

Example 17: Preparation of Compound 57

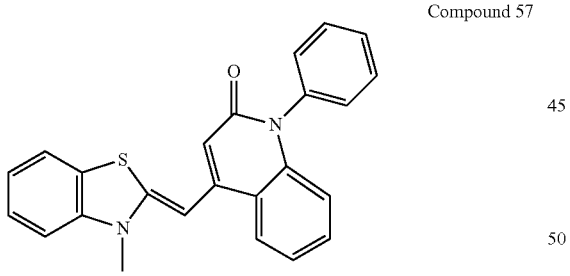
Compound 57

To a mixture of 3-methyl-2-methylthiobenzothiazolium tosylate (5 g, 13.6 mmol), 1,2-dihydro-4-methyl-1-phenyl-2-quinolone (prepared according to U.S. Pat. No. 5,658,751) (3 g, 11.3 mmol) and N,N-diisopropylethylamine (7.8 mL, 45 mmol) in $CH_2Cl_2$ (100 mL) at 0° C. was added trimethysilyl trifluoromethanesulfonate (10.3 mL, 57 mmol) dropwise. After the addition was completed, the solution was refluxed for 1 hr and then cooled down to 0° C. Water (110 mL) was added dropwise and the mixture was stirred at 0° C. for 1 hr. The aqueous layer was extracted with $CH_2Cl_2$ (2×50 mL) and the combined organic layers was dried with anhydrous $Na_2SO_4$. The solvent was removed and the residue was dried to a constant weight (3 g) and used without further purification.

Example 18: Preparation of Compound 58

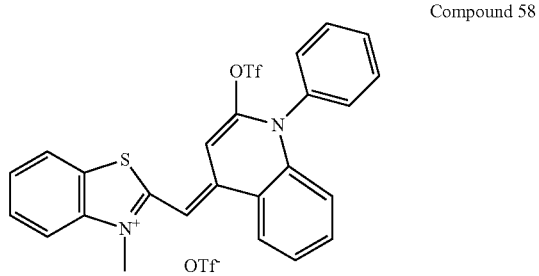 [SMILES: C[n+]1c(/C=C2\C=C(OS(=O)(=O)C(F)(F)F)N(c3ccccc3)c3ccccc32)sc2ccccc21]
Compound 58

To a solution of Compound 57 (2 g, 5.2 mmol) in $CH_2Cl_2$ (50 mL) at 0° C. was added trifluoromethanesulfonic anhydride (0.93 mL, 5.5 mmol) dropwise. The mixture was kept stirring at 0° C. for 2 hrs and then concentrated to dryness in vacuo. The residue was dried to a constant weight to give an orange solid (3.4 g), which was used for the next step without further purification.

Example 19: Preparation of Compound 59

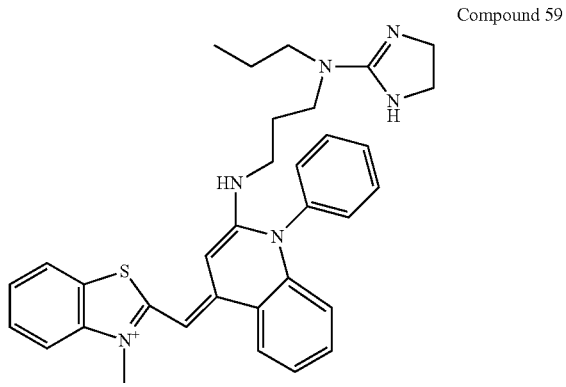
Compound 59

A mixture of Compound 58 (50 mg, 0.08 mmol) and Compound 52 (34 mg, 0.082 mmol) and N,N-diisopropylethylamine (72 µL, 0.42 mmol) in 1,2-dichloroethane (3 mL) was heated at 30° C. overnight. After cooling down to room temperature, the yellow precipitate (55 mg) was collected by suction filtration and dried to a constant weight.

Example 20: Preparation of Compound 60

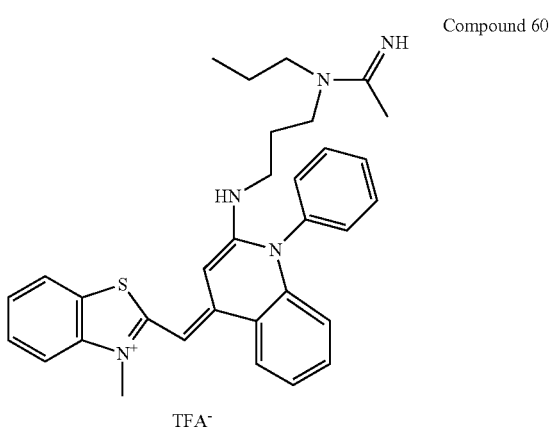 [SMILES: CCCN(CCCNC1=C/C(=C\c2sc3ccccc3[n+]2C)c2ccccc2N1c1ccccc1)C(C)=N]
Compound 60

A mixture of Compound 58 (50 mg, 0.08 mmol) and Compound 54 (22 mg, 0.082 mmol) and N,N-diisopropylethylamine (72 µL, 0.42 mmol) in 1,2-dichloroethane (3 mL) was heated at 30° C. overnight. After cooling down to room temperature, the yellow precipitate (35 mg) was collected by suction filtration and dried to a constant weight.

Example 21: Preparation of Compound 5 of Table 1

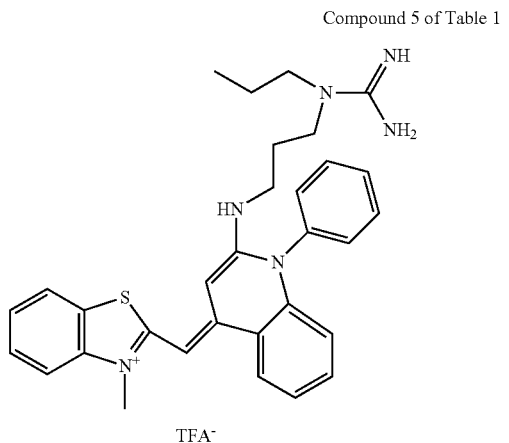 [SMILES: CCCN(CCCNC1=C/C(=C\c2sc3ccccc3[n+]2C)c2ccccc2N1c1ccccc1)C(=N)N]

Compound 5 of Table 1

TFA⁻

A mixture of Compound 58 (50 mg, 0.08 mmol) and Compound 56 (32 mg, 0.082 mmol) and N,N-diisopropylethylamine (72 µL, 0.42 mmol) in 1,2-dichloroethane (3 mL) was heated at 30° C. overnight. After cooling down to room temperature, the yellow precipitate (45 mg) was collected by suction filtration and dried to a constant weight.

Example 22: Preparation of Compound 7 of Table 1

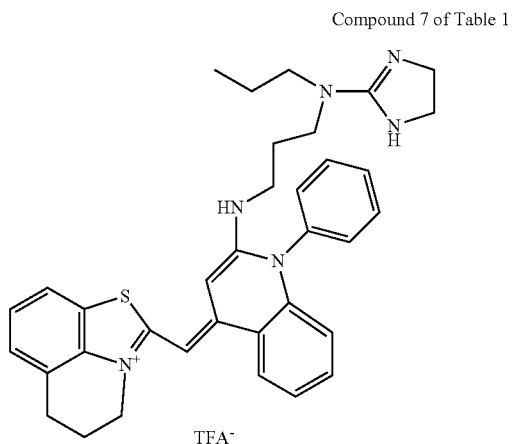 [SMILES: CCCN(CCCNC1=C/C(=C\c2sc3cccc4c3[n+]2CCC4)c2ccccc2N1c1ccccc1)C1=NCCN1]

Compound 7 of Table 1

TFA⁻

A mixture of 2-chloro-4-((5,6-dihydrothiazolo[5,4,3-ij]quinolin-2(4H)-ylidene)methyl)-1-phenyl]quinolinium chloride (prepared according to US patent application No. 20100233710) (35 mg, 0.08 mmol) and Compound 52 (34 mg, 0.082 mmol) and N,N-diisopropylethylamine (72 µL, 0.42 mmol) in 1,2-dichloroethane (3 mL) was heated at 30° C. overnight. After cooling down to room temperature, the yellow precipitate (40 mg) was collected by suction filtration and dried to a constant weight.

Example 23: Preparation of Compound 6 of Table 1

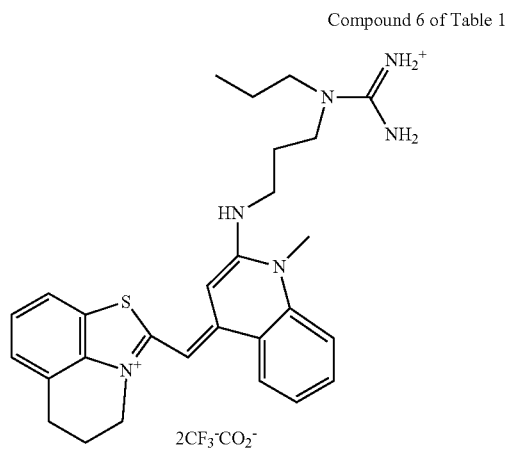 [SMILES: CCCN(CCCNC1=C/C(=C\c2sc3cccc4c3[n+]2CCC4)c2ccccc2N1C)C(N)=[NH2+]]

Compound 6 of Table 1

2CF₃CO₂⁻

A mixture of 2-chloro-4-((5,6-dihydrothiazolo[5,4,3-ij]quinolin-2(4H)-ylidene)methyl)-1-methyl]quinolinium chloride (prepared according to US patent application #: 20100233710) (30 mg, 0.08 mmol) and Compound No. 7 (32 mg, 0.082 mmol) and diisopropylethylamine (72 µL, 0.42 mmol) in 1,2-dichloroethane (3 mL) was heated at 30° C. overnight. After cooling down to room temperature, the yellow precipitate (31 mg) was collected by suction filtration and dried to a constant weight.

Example 24: Preparation of Compound 61

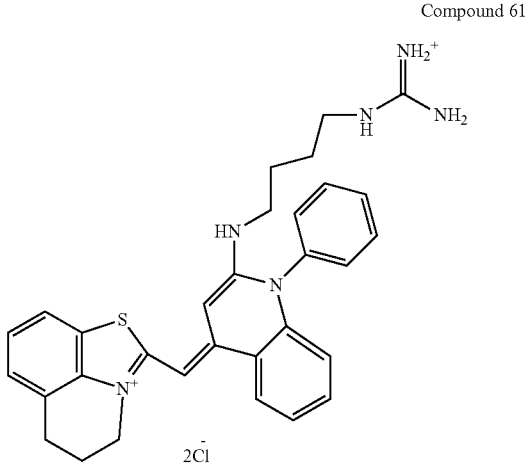 [SMILES: NC(=[NH2+])NCCCCNC1=C/C(=C\c2sc3cccc4c3[n+]2CCC4)c2ccccc2N1c1ccccc1]

Compound 61

2Cl⁻

A mixture of 2-chloro-4-((5,6-dihydrothiazolo[5,4,3-ij]quinolin-2(4H)-ylidene)methyl)-1-phenyl]quinolinium chloride (0.3 g, 0.65 mmol) and agmatine sulfate salt (0.44 g, 1.9 mmol) and N,N-diisopropylethylamine (1.1 mL, 6.5 mmol) in 1,2-dichloroethane (30 mL) was heated at 50° C. overnight. After cooling down to room temperature, the yellow precipitate (0.3 g) was collected by suction filtration and dried to a constant weight.

Example 25: Preparation of Compound 62

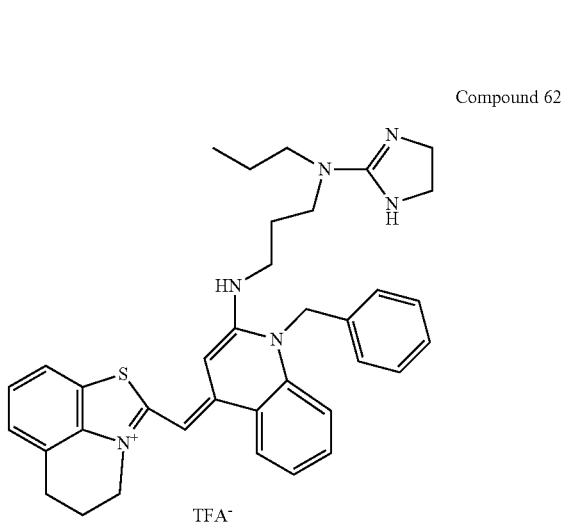 [SMILES: CCCN(CCCNC1=C/C(=C\c2sc3cccc4c3[n+]2CCC4)c2ccccc2N1Cc1ccccc1)C1=NCCN1]

Compound 62

A mixture of 2-chloro-4-((5,6-dihydrothiazolo[5,4,3-ij]quinolin-2(4H)-ylidene)methyl)-1-benzyl]quinolinium chloride (prepared according to US patent application #: 20100233710) (36 mg, 0.08 mmol) and Compound No. 3 (34 mg, 0.082 mmol) and diisopropylethylamine (72 μL, 0.42 mmol) in 1,2-dichloroethane (3 mL) was heated at 30° C. overnight. After cooling down to room temperature, the yellow precipitate (33 mg) was collected by suction filtration and dried to a constant weight.

Example 26: Preparation of Compound 63

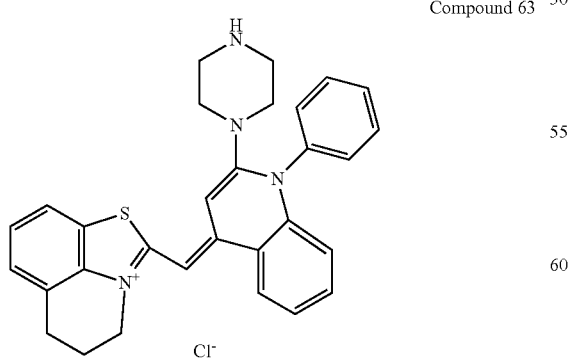

Compound 63

A mixture of 2-chloro-4-((5,6-dihydrothiazolo[5,4,3-ij]quinolin-2(4H)-ylidene)methyl)-1-phenyl]quinolinium chloride (0.1 g, 0.21 mmol) and piperazine (0.17 mL, 2.1 mmol) in 1,2-dichloroethane (15 mL) was heated at 90° C. overnight. After cooling down to room temperature, the orange precipitate (60 mg) was collected by suction filtration and dried to a constant weight.

Example 27: Preparation of Compound 24 of Table 1

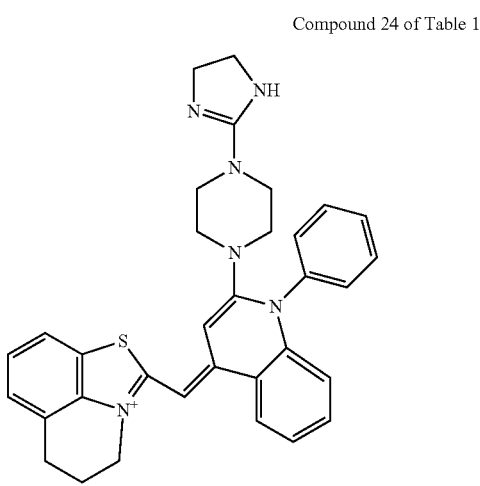 [SMILES: C1=C(N2CCN(C3=NCCN3)CC2)N(c2ccccc2)c2ccccc2/C1=C/c1sc2cccc3c2[n+]1CCC3]

Compound 24 of Table 1

A mixture of Compound 63 (50 mg, 0.1 mmol), 2-methylthio-2-imidazoline hydriodide (71 mg, 0.3 mmol) and N,N-diisopropylethylamine (85 μL, 0.5 mmol) in EtOH (5 mL) was heated at 50° C. overnight. The orange precipitate (25 mg) was collected by suction filtration.

Example 28: Preparation of Compound 64

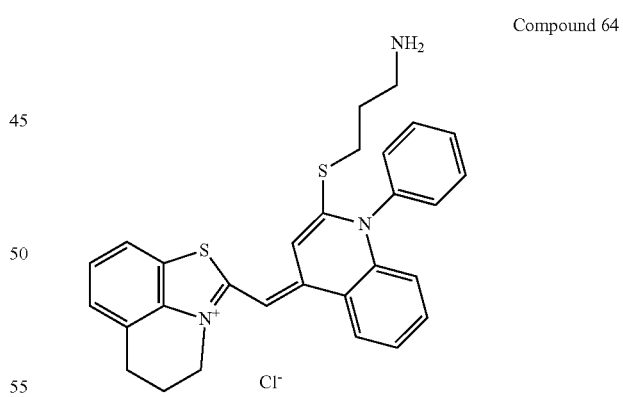

Compound 64

A mixture of 2-chloro-4-((5,6-dihydrothiazolo[5,4,3-ij]quinolin-2(4H)-ylidene)methyl)-1-phenyl]quinoliniumchloride (0.1 g, 0.21 mmol), 3-amino-1-propanethiol hydrochloride (25 mg, 0.27 mmol) and diisopropylethylamine (47 uL, 0.27 mmol) in $CH_2Cl_2$ (10 mL) under $N_2$ was stirred at room temperature overnight. The mixture was concentrated to 5 mL and the orange precipitate (60 mg) was collected by suction filtration and dried to a constant weight.

Example 29: Preparation of Compound 65

Compound 65

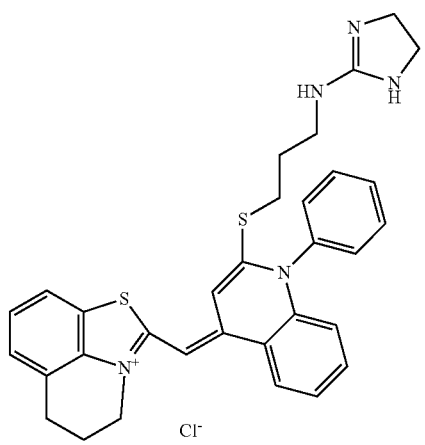

Compound 65 (21 mg) was prepared from Compound 64 (40 mg, 0.08 mmol), 2-methylthio-2-imidazoline hydriodide (56 mg, 0.23 mmol) and N,N-diisopropylethylamine according to the procedure of Example 27.

Example 30: Preparation of Compound 66

Compound 66

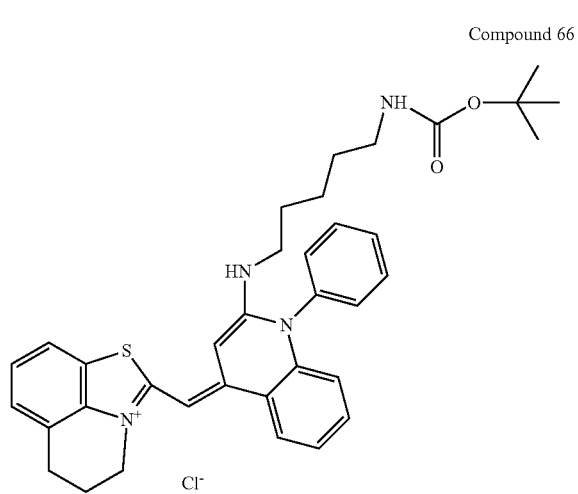 [SMILES: CC(C)(C)OC(=O)NCCCCCNC1=C/C(=C\c2sc3cccc4c3[n+]2CCC4)c2ccccc2N1c1ccccc1 ; [Cl-]]

A mixture of 2-chloro-4-((5,6-dihydrothiazolo[5,4,3-ij]quinolin-2(4H)-ylidene)methyl)-1-phenyl]quinolinium chloride (0.2 g, 0.4 mmol) and mono-tBOC-cadaverine (0.4 g, 2 mmol) in 1,2-dichloroethane (10 mL) was heated at 50° C. overnight. The volume of solvent was reduced in vacuo and the yellow precipitate (0.21 g) was collected by suction filtration.

Example 31: Preparation of Compound 67

Compound 67

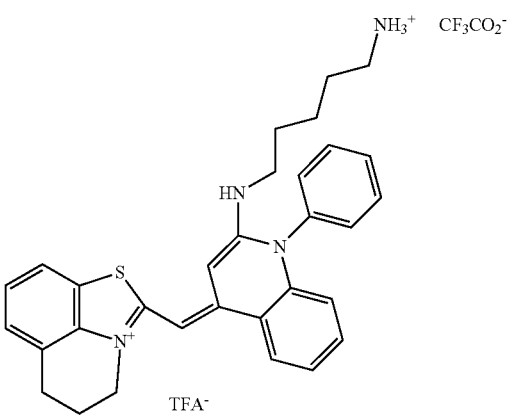

To a solution of Compound 66 (0.2 g, 0.31 mmol) in $CH_2Cl_2$ (10 mL) at 0° C. was added TFA (3 mL). The mixture was stirred at 0° C. for 1 hr and then concentrated to dryness in vacuo. $Et_2O$ (10 mL) was added to the residue and the suspension was stirred at room temperature overnight. The yellow precipitate (0.2 g) was collected by centrifugation.

Example 32: Preparation of Compound 68

Compound 68

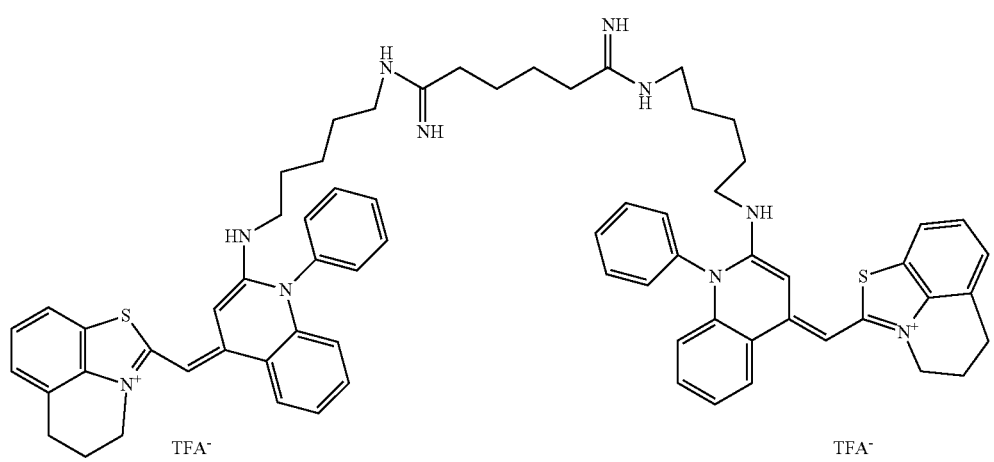

A mixture of Compound 67 (0.15 g, 0.21 mmol), dimethyl adipimidate dihydrochloride (23 mg, 0.1 mmol) and N,N-diisopropylethylamine (0.4 mL, 2.2 mmol) in EtOH (10 mL) was heated at 90° C. overnight. After cooling down to room temperature, the yellow precipitate (31 mg) was collected by suction filtration.

Example 33: Preparation of Compound 32 of Table 1

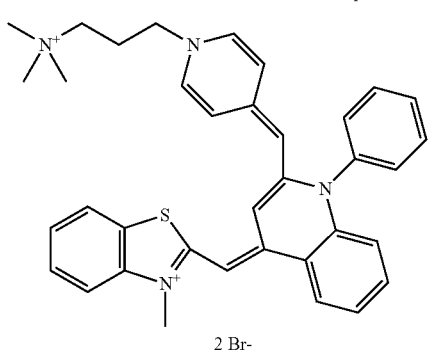

Compound 32 of Table 1

2 Br-

A mixture of Compound 58 (0.1 g, 0.15 mmol), 1-trimethylammonium-3-(4-methylpyridinium)-propane (0.2 g, 0.58 mmol) and N,N-diisopropylethylamine (0.2 mL, 1.1 mmol) in DMF (2 mL) was stirred at room temperature for 2 days. The solution was concentrated to dryness in vacuo and the residue was column chromatography on aluminum oxide to give a red solid (15 mg).

Example 34: Preparation of Compound 69

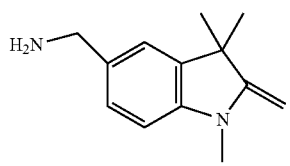

Compound 69

2,3,3-Trimethylindoline (5 g) and N-hydroxymethylphthamide (1 equivalent) were carefully mixed in 30 mL methanesulfonic acid. The mixture was stirred at room temperature overnight and then poured into water (200 mL). The solid was collected, briefly dried and then redissolved in methanol (200 mL). To the solution was added hydrazine (10 equivalents to the amount of starting 2,3,3-trimethylindoline). The resulting mixture was stirred at room temperature for 24 hours and suction filtered. The filtrate was evaporated and the remaining solid was purified on a silica get column using methanol/chloroform to give Compound 69 as a pinkish solid.

Example 35: Preparation of Compound 70

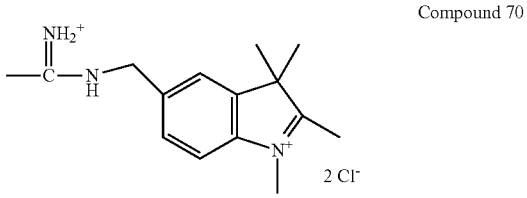 [SMILES: CC(=[NH2+])NCc1ccc2c(c1)C(C)(C)C(C)=[N+]2C]

Compound 70

2 Cl-

A mixture of Compound 69 (700 mg, 1.2 mmol), ethyl acetimidate hydrochloride (360 mg, 3 mmol) and N,N-diisopropylethylamine (1 mL, 6 mmol) in EtOH (20 mL) was heated at 90° C. overnight. After cooling down to room temperature, the solvent was evaporated to give a gummy solid, which was purified on a silica gel column using MeOH/CHCl$_3$ to give the neutral form of Compound 70. The neutral form of Compound 70 was redissolved in MeOH (5 mL). HCl (4 M in dioxane) (0.5 mL) was added, followed by addition of ether to precipitate out Compound 70 in the HCl salt form.

Example 36: Preparation of Compound 36 of Table 1

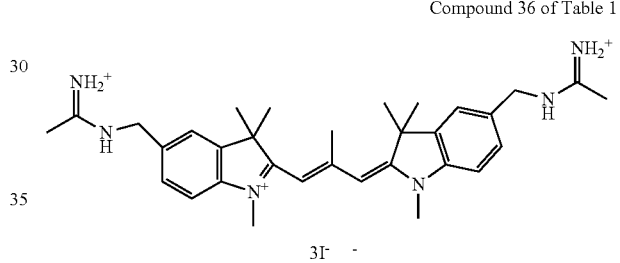

Compound 36 of Table 1

3I-

Compound 70 (200 mg) was dissolved in 5 mL pyridine, followed by the addition of 3 equivalents of triethyl orthoformate. The mixture was refluxed for 5 hours to form a dark red solution. The solution was added in small portions to a stirred solution of NaI (10 equivalents) in 30 mL water. The solid was collected and then redissolved in DMF (1 mL), followed by addition of the solution to 20 mL 1 N HCl containing 0.5 g NaI. The mixture was centrifuged to collect the solid at the bottom of the vial. The supernatant was decanted off and the solid was dried to the final product as a dark red powder.

Example 37: Preparation of Compound 71

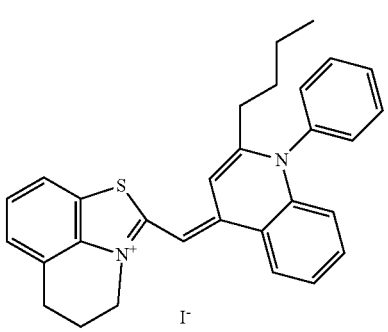

Compound 71

I-

To a solution of 1,2-dihydro-4-methyl-1-phenyl-2-quinolone (0.2 g, 1 mmol) in THF (15 mL) at −78° C. was added 2.5 M n-butyllithium in hexanes (1.5 mL, 3.75 mmol). The mixture was stirred at −78° C. for one hour and acetic acid (0.4 mL,) was added. The mixture was warmed up slowly to room temperature and kept stirring at room temperature for another 3 hrs. The mixture was evaporated to dryness in vacuo. The residue was re-dissolved in $CH_2Cl_2$ (20 mL), followed by the addition of 1-(methylthio)-7,8-dihydro-6H-thiazolo[5,4,3-ij]quinolin-9-ium tosylate (0.394 g, 1 mmol) (prepared according to US patent application No. 20100233710) and triethylamine (0.56 mL). The mixture was stirred at room temperature for 2 hrs and then concentrated to dryness in vacuo. The residue was dissolved in DMF (5 mL) and added dropwise to a solution of NaI (1.7 g) in water (90 mL). The precipitate was collected by suction filtration and dried to a constant weight (0.12 g).

Example 38: Preparation of Compound 72

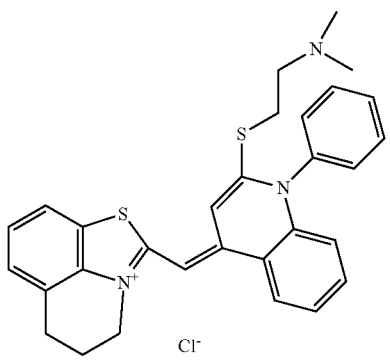

Compound 72

A mixture of 2-chloro-4-((5,6-dihydrothiazolo[5,4,3-ij]quinolin-2(4H)-ylidene)methyl)-1-methyl]quinolinium chloride (50 mg, 0.1 mmol), 2-dimethylaminoethanethiol hydrochloride (16 mg, 0.1 mmol) and N,N-diisopropylethylamine (20 uL, 0.1 mmol) in $CH_2Cl_2$ (5 mL) under $N_2$ was stirred at room temperature overnight. The orange precipitate (13 mg) was collected by centrifugation.

Example 39: Preparation of Compound 73

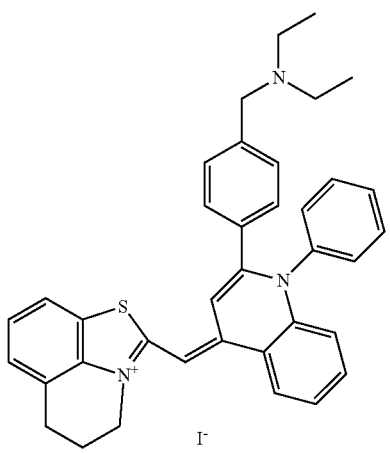

Compound 73

To 4'-bromobenzyldiethylamine (0.3 g, 1.23 mmol) in anhydrous THF (10 mL) at −78° C. under $N_2$ was added 2.5 M n-butyllithium in hexanes (0.5 mL, 1.23 mmol) and then followed by the addition of 1,2-dihydro-4-methyl-1-phenyl-2-quinolone (0.3 g, 1.25 mmol) in THF (10 mL). The mixture was stirred at −78° C. for 1 hour and HOAc (0.5 mL) was added. The mixture was stirred at room temperature for another hour and then concentrated to dryness in vacuo. The residue was dissolved in $CH_2Cl_2$ (10 mL) and then followed by the addition of 1-(methylthio)-7,8-dihydro-6H-thiazolo[5,4,3-ij]quinolin-9-ium tosylate (0.484 g, 1.23 mmol) and triethylamine (0.56 mL). The mixture was stirred at room temperature for 2 hrs and concentrated to dryness in vacuo. The residue was dissolved in MeOH (5 mL) and then added dropwise to a solution of NaI (2 g) in water (50 mL). The orange precipitate (42 mg) was collected by suction filtration and dried to a constant weight.

Example 40: Preparation of Compound 74

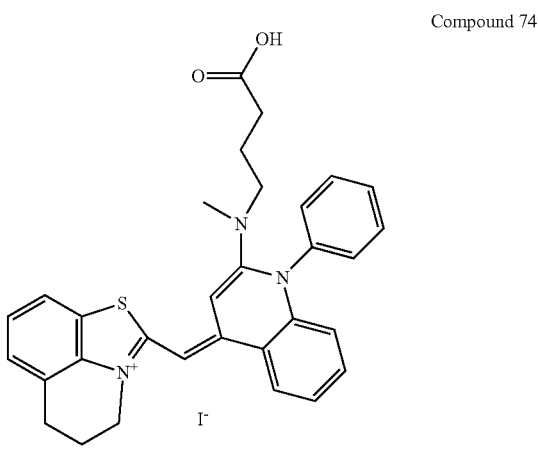 [SMILES: CN(CCCC(=O)O)C1=C/C(=C\c2sc3cccc4c3[n+]2CCC4)c2ccccc2N1c1ccccc1 ; [I-]]

Compound 74

A solution of 4-(methylamino)butyric acid hydrochloride (70 mg, 0.46 mmol), t-butyldimethylsilyl chloride (76 mg, 0.5 mmol) and triethylamine (0.35 mL, 2.3 mmol) in 1,2-dichloroethane (5 mL) was stirred at room temperature for 4 hrs. 2-chloro-4-((5,6-dihydrothiazolo[5,4,3-ij]quinolin-2(4H)-ylidene)methyl)-1-phenyl]quinolinium chloride (78 mg, 0.17 mmol) was added and the mixture was heated at 60° C. for 1 hr. The mixture was concentrated to dryness in vacuo. The residue was dissolved in DMF (4 mL) and added dropwise to a solution of NaI (0.6 g) and 57% HI (0.4 g) in water (50 mL). The orange precipitate (33 mg) was collected by suction filtration and dried to a constant weight.

Example 41: Preparation of Compound 75

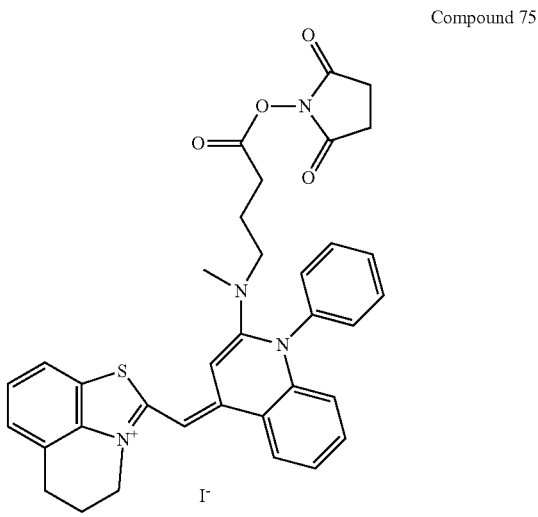 [SMILES: CN(CCCC(=O)ON1C(=O)CCC1=O)C1=C/C(=C\c2sc3cccc4c3[n+]2CCC4)c2ccccc2N1c1ccccc1 ; [I-]]

Compound 75

To a solution of Compound 74 (20 mg, 0.03 mmol) in DMF (0.5 mL) at room temperature was added triethylamine (22 uL, 0.15 mmol) and TSTU (10 mg, 0.03 mmol). The mixture was stirred at room temperature for 0.5 hr and then concentrated to dryness in vacuo. The residue was stirred as a suspension in EtOAc (2 mL) for 1 hr and the orange precipitate (18 mg) was collected by suction filtration.

Example 42: Preparation of Compound 76

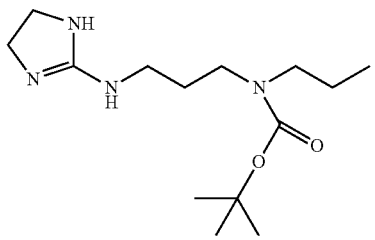

Compound 76

Compound No. 33 (85 mg) was prepared from Compound 50a (0.1 g, 0.46 mmol) and 2-methylthio-2-imidazoline hydriodide (0.14 g, 0.56 mmol) according to the procedure to synthesis Compound 51.

Example 43: Preparation of Compound 77

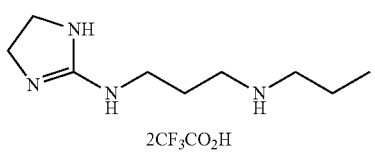

Compound 77

2CF$_3$CO$_2$H

Compound 77 (65 mg) was prepared from Compound 76 (70 mg, 0.25 mmol) according to the procedure to synthesize Compound 52.

Example 44: Preparation of Compound 78

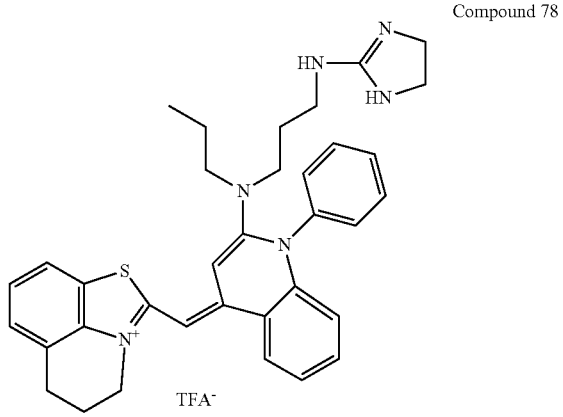 [SMILES: CCCN(CCCNC1=NCCN1)C1=C/C(=C\c2sc3cccc4c3[n+]2CCC4)c2ccccc2N1c1ccccc1]

Compound 78

TFA$^-$

Compound 78 (25 mg) was prepared from 2-chloro-4-((5,6-dihydrothiazolo[5,4,3-ij]quinolin-2(4H)-ylidene)methyl)-1-phenyl]quinolinium chloride (35 mg, 0.08 mmol) and Compound 77 (34 mg, 0.082 mmol) according to the procedure Example 22.

Example 45: Staining of Fixed Cells with Compound 36

Compound 36 and similar compounds of the invention can be used to stain the nuclei of fixed cells with good specificity. The high photostability and relatively long emission wavelength (~565 nm) make the dye a useful cell counterstain. HeLa cells were plated on an 8-chambered Lab-Tek cover glass at 4×10$^4$ cells per chamber and cultured overnight. The day after plating, the cells were fixed in 4% paraformaldehyde/PBS for 15 minutes at room temperature. The cells were rinsed in PBS and blocked in PBS containing 5% normal goat serum and 0.1% Triton X-100 for 30 minutes at room temperature. Cells were stained with 10 uM Dye 36 in blocking buffer for 10 minutes at room temperature and imaged in the same solution by confocal microscopy in the Cy3 channel of a Zeiss LSM 700 confocal microscope. The cellular image is shown in FIG. 14.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

CITED REFERENCES

Dragan, A. I., E. S. Bishop, et al. (2010). "Metal-enhanced PicoGreen fluorescence: application for double-stranded DNA quantification." Anal Biochem 396(1): 8-12.

Ishchenko, A. V. K. A. A. (2009). "Merocyanine dyes: synthesis, structure, properties and applications." Russ. Chem. Rev. 78(2).

Mao, F., W. Y. Leung, et al. (2007). "Characterization of EvaGreen and the implication of its physicochemical properties for qPCR applications." BMC Biotechnol 7: 76.

Moreda, W. F., Alexander (1997). "Novel Heterocyclic dyes as DNA markers, Part I. synthesis and characterization." Tetrahedron 53(37).

Schofield, G. G. (2004). "PicoGmeter, a custom-made fluorometer for the quantification of dsDNA by PicoGreen fluorescence." Biotechniques 37(5): 778-780, 782.

Singer, V. L., L. J. Jones, et al. (1997). "Characterization of PicoGreen reagent and development of a fluorescence-based solution assay for double-stranded DNA quantitation." Anal Biochem 249(2): 228-238.

Zipper, H., H. Brunner, et al. (2004). "Investigations on DNA intercalation and surface binding by SYBR Green I, its structure determination and methodological implications." Nucleic Acids Res 32(12): e103.

What is claimed is:
1. A composition comprising a compound selected from the group consisting of:
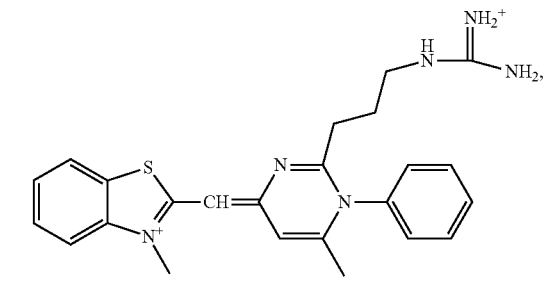
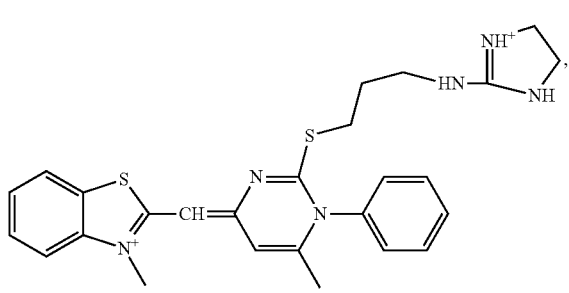
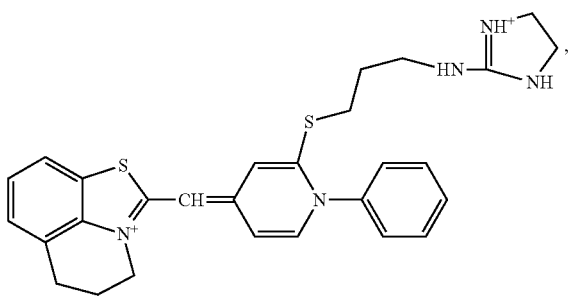
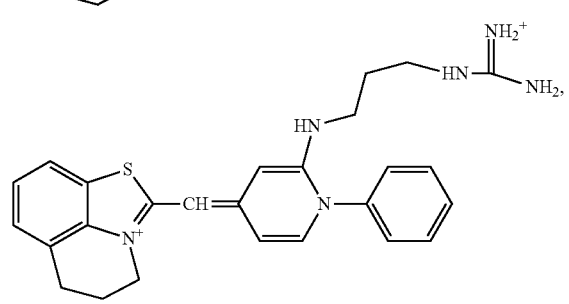
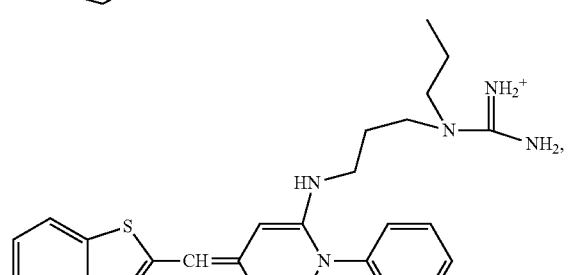
-continued
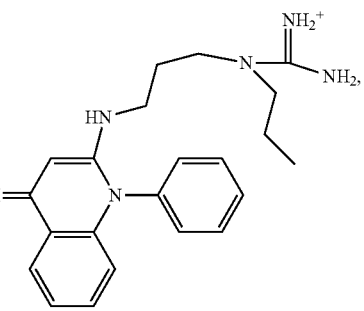
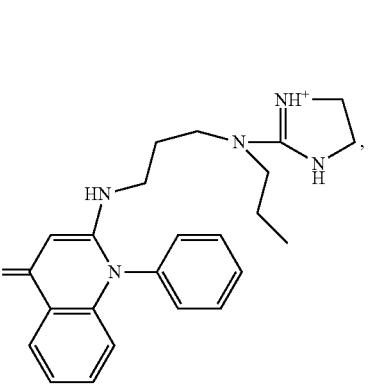
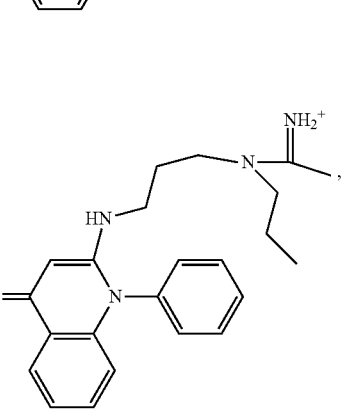
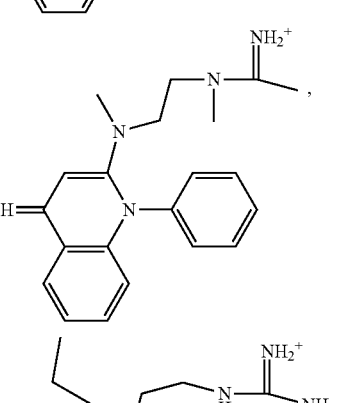
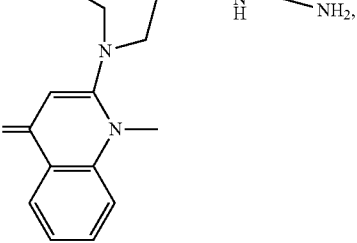

93
-continued
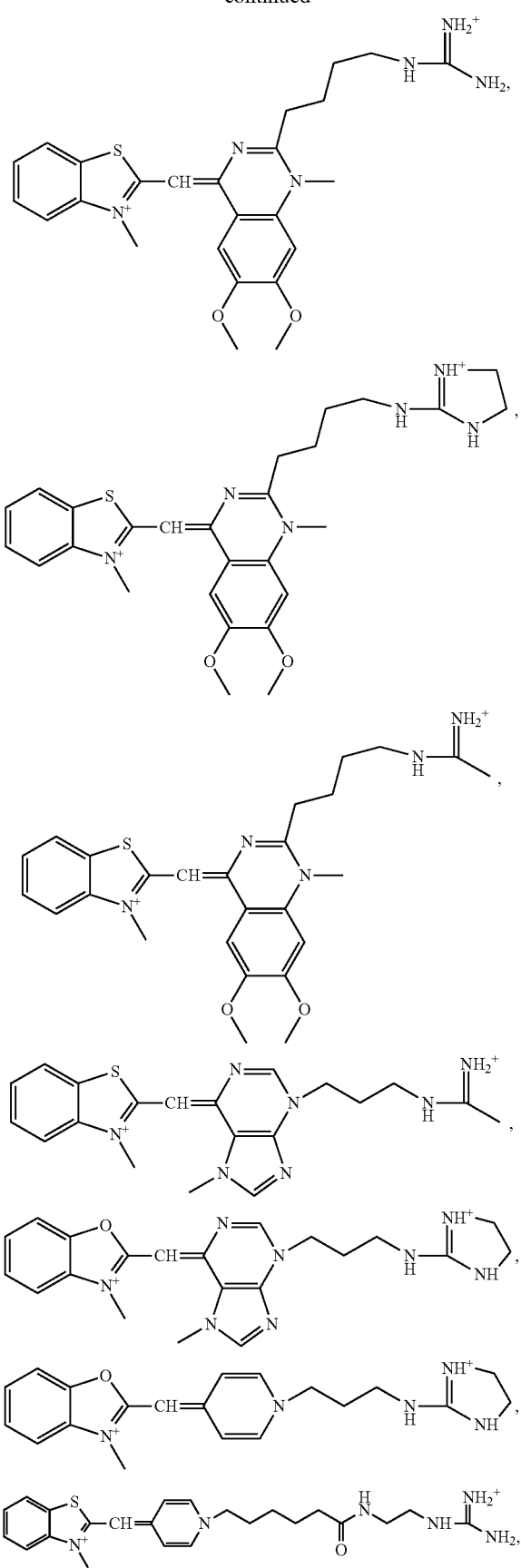
94
-continued
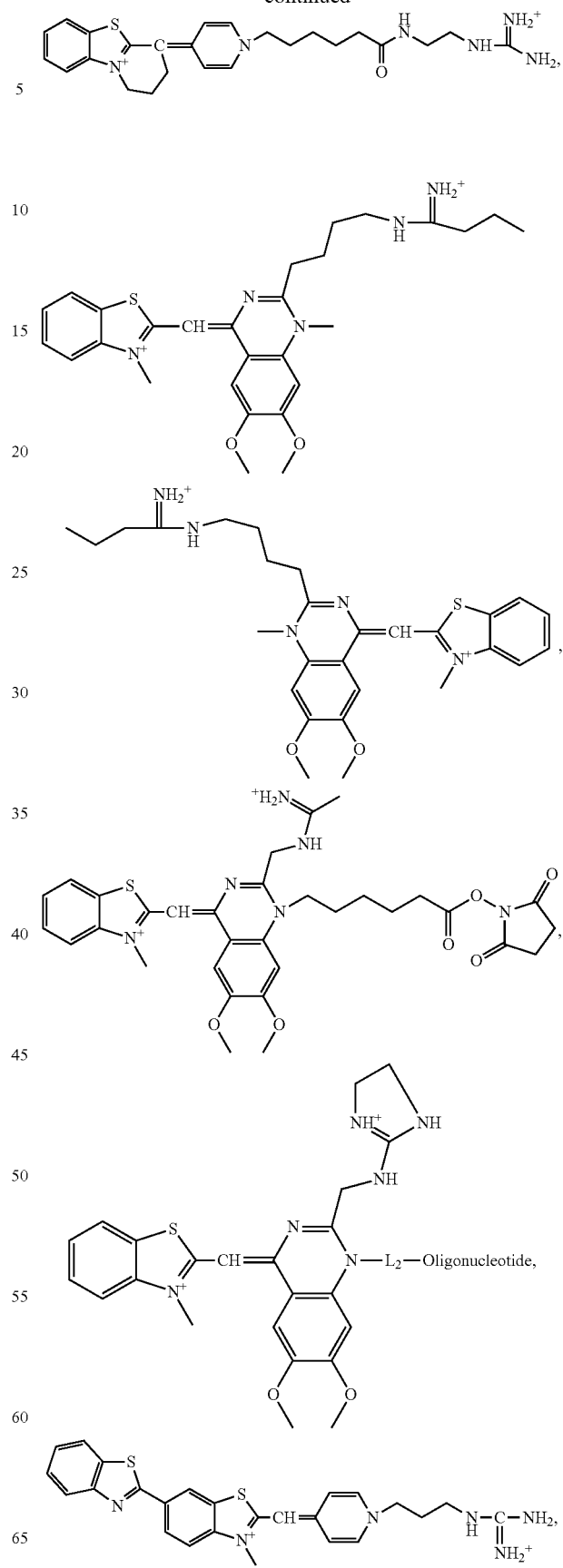

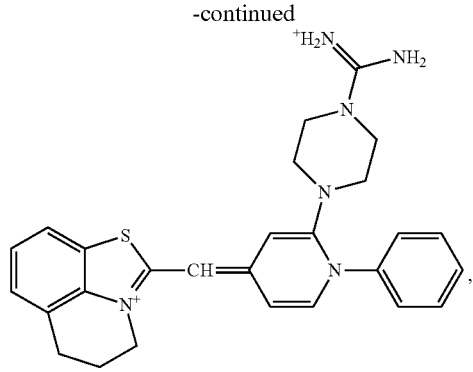
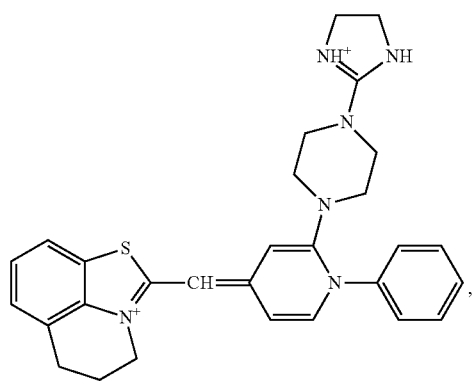
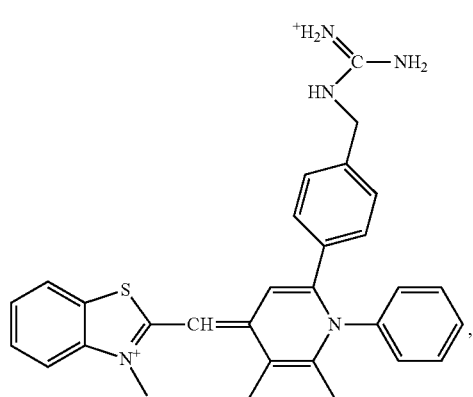
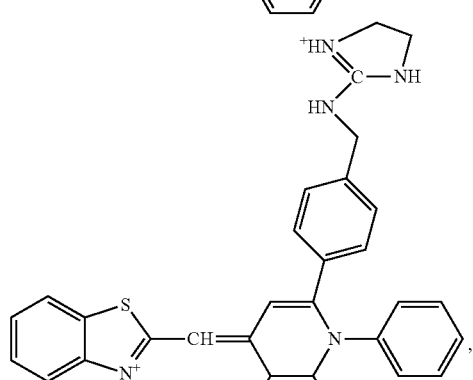
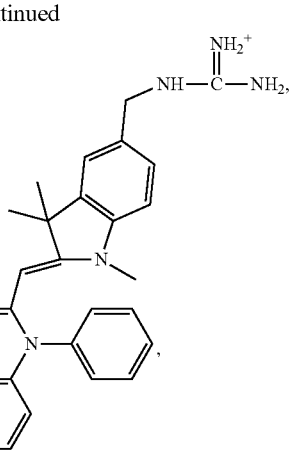
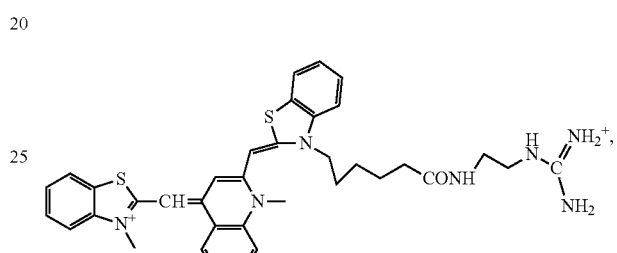
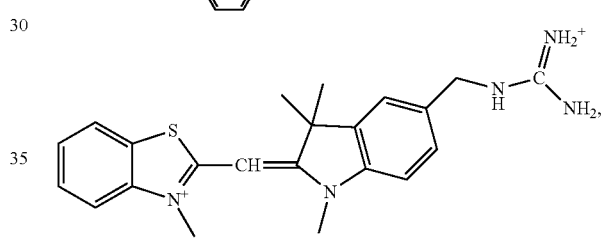
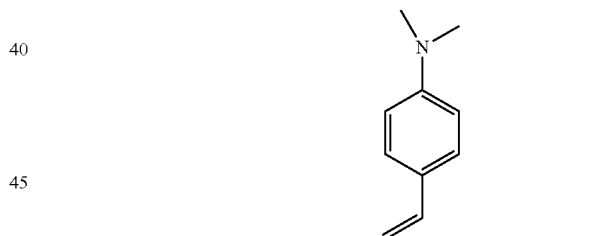
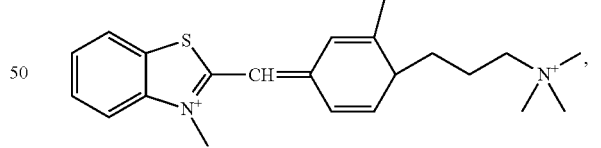
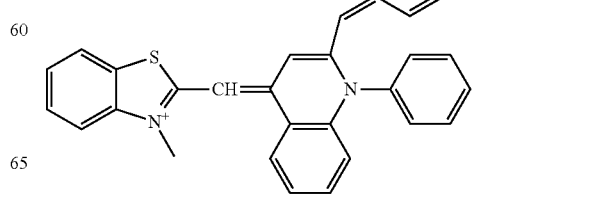

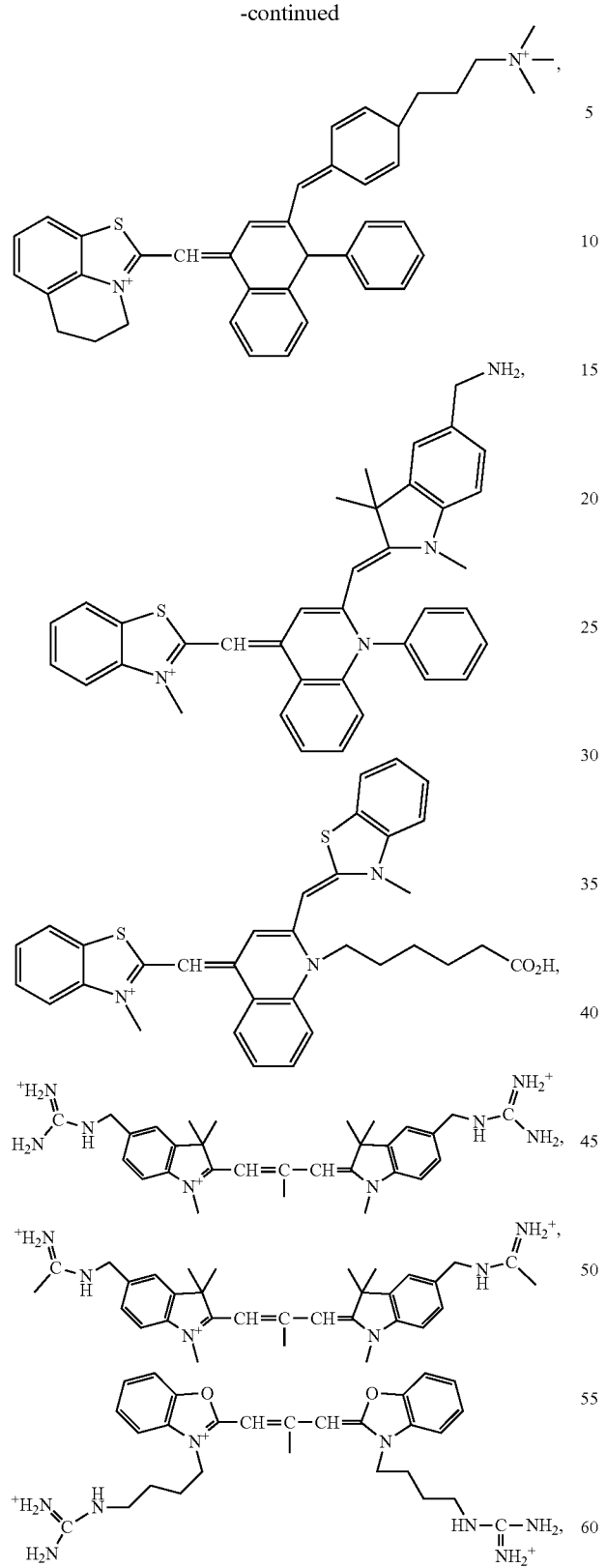
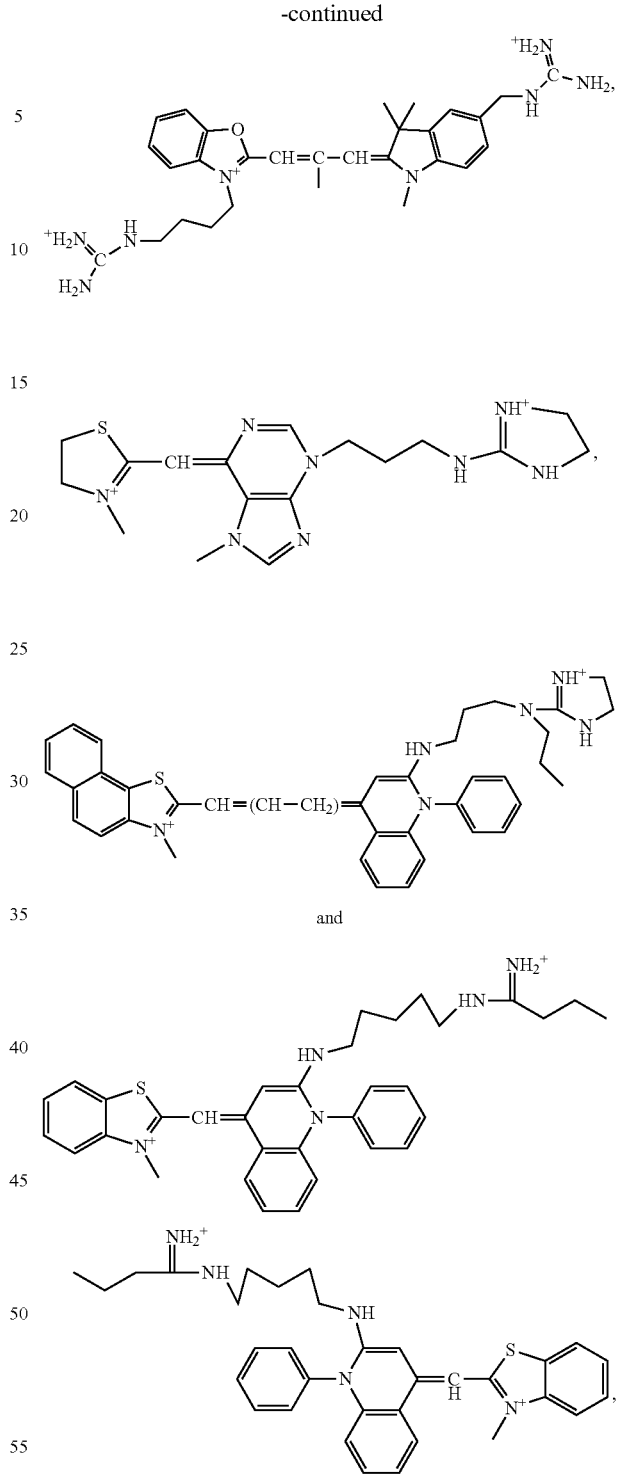
wherein $L_2$ is a linker moiety comprising 1-20 nonhydrogen atoms and the composition further comprises a counterion.
* * * * *

UNITED STATES PATENT AND TRADEMARK OFFICE
CERTIFICATE OF CORRECTION

PATENT NO. : 9,682,970 B2
APPLICATION NO. : 14/409325
DATED : June 20, 2017
INVENTOR(S) : Fei Mao et al.

Page 1 of 1

It is certified that error appears in the above-identified patent and that said Letters Patent is hereby corrected as shown below:

In the Claims

In Column 96, Lines 39-54 delete compound

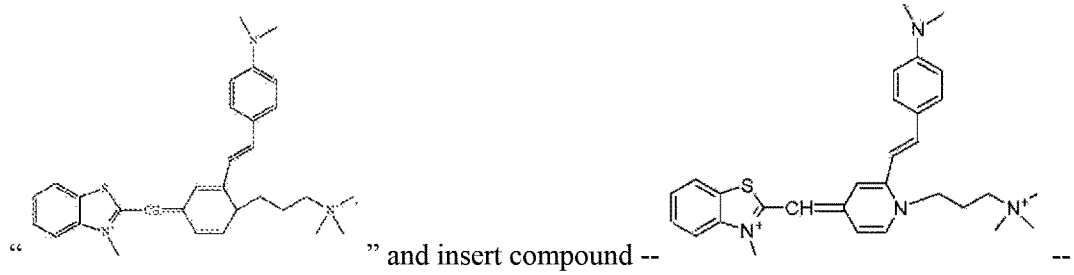

" and insert compound --                    --

In Column 97, Lines 1-14 delete compound

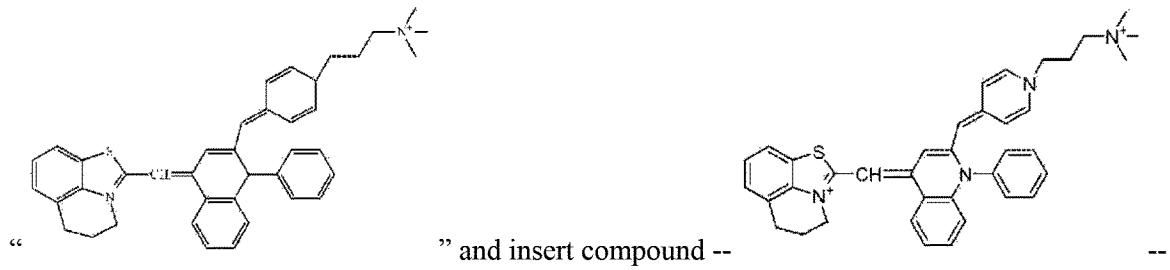

" and insert compound --                    --

Signed and Sealed this
Seventh Day of August, 2018

Andrei Iancu
*Director of the United States Patent and Trademark Office*